United States Patent
Garcia-Moreno et al.

(10) Patent No.: US 9,499,580 B2
(45) Date of Patent: Nov. 22, 2016

(54) METHOD FOR INCORPORATING INTERNAL POLAR AND IONIZABLE GROUPS IN PROTEINS

(75) Inventors: Bertrand E. Garcia-Moreno, Baltimore, MD (US); Daniel G. Isom, Durham, NC (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 13/513,259

(22) PCT Filed: Dec. 2, 2010

(86) PCT No.: PCT/US2010/058800
§ 371 (c)(1),
(2), (4) Date: Jun. 28, 2012

(87) PCT Pub. No.: WO2011/069017
PCT Pub. Date: Jun. 9, 2011

(65) Prior Publication Data
US 2012/0258518 A1  Oct. 11, 2012

Related U.S. Application Data

(60) Provisional application No. 61/265,946, filed on Dec. 2, 2009.

(51) Int. Cl.
*C07K 1/107* (2006.01)
*C12N 9/22* (2006.01)
*C07K 14/31* (2006.01)
*G06F 19/16* (2011.01)

(52) U.S. Cl.
CPC .............. *C07K 1/107* (2013.01); *C07K 14/31* (2013.01); *C12N 9/22* (2013.01); *G06F 19/16* (2013.01)

(58) Field of Classification Search
CPC ................................. C07K 1/107; C12N 9/22
See application file for complete search history.

(56) References Cited

U.S. PATENT DOCUMENTS 6,385,546 B1  5/2002  Kahn et al.
2015/0099290 A1  4/2015  Garcia-Moreno et al.

FOREIGN PATENT DOCUMENTS

WO  2011069017 A1  6/2011

OTHER PUBLICATIONS

Chen et al., "Increasing the Thermostability of Staphylococcal Nuclease: Implications for the Origin of Protein Thermostability", J. Mol. Biol. (2000) 303:125-130. < doi:10.1006/jmbi.2000.4140 >.*

Isom et al., "High tolerance for ionizable residues in the hydrophobic interior of proteins", PNAS, Nov. 18, 2008, 105(46):17784-17788.*
Hollien et al., "A Thermodynamic Comparison of Mesophilic and Thermophilic Ribonucleases H", Biochemistry 1999, 38, 3831-3836.*
Dao-pin et al., "Structural and Thermodynamic Consequences of Burying a Charged Residue within the Hydrophobic Core of T4 Lysozyme", Biochemistry, 1991, 30:11521-11529.*
Karp et al., High apparent dielectric constant inside a protein reflects structural reorganization coupled to the ionization of an internal Asp. Biophys. J. 2007, vol. 92, No. 6, pp. 2041-2053.
Garcia-Moreno et al. Experimental measurement of the effective dielectric in the hydrophobic core of a protein. Biophys. Chem., 1997, vol. 64, No. 1-3, pp. 211-224.
Dwyer et al., High apparent dielectric constants in the interior of a protein reflect water penetration. Biophys. J., 2000, vol. 79, No. 3, pp. 1610-1620; p. 1611, para 5.
Harms et al., A buried lysine that titrates with a normal pKa; role of conformational flexibility at the protein-water interface as a determinant of pKa values, Protein Sci., 2008, vol. 17, No. 5, pp. 833-845-; abstract; p. 842, para 2.
Stites et al. In a staphylococcal nuclease mutant the side-chain of a lysine replacing valine 66 is fully buried in the hydrophobic core, J. Mol. Biol. 1991, vol. 221, No. 1, pp. 7-14.
Denisov et al., Stabilization of Internal Charges in a Protein: Water Penetration or Conformational Change Biophysical Journal, 2004, vol . 87, No. 6, pp. 3982-3994.
Byrne et al., Energetic contribution of side chain hydrogen bonding to the stability of staphylococcal nuclease., Biochemistry, 1995, vol. 34, No. 42, pp. 13949-13960.
European Search Report dated Jul. 16, 2014 from European Application No. 10835157.8-1453/2507631 PCT/US2010/058800.
Rastogi VK & Girvin ME (1999) Structural changes linked to proton translocation by subunit c of the ATPase synthase. *Nature* 402: 263-268.
Harms MJ, et al. (2009) The pKa values of acidic and basic residues buried at the same internal location in a protein are governed by different factors. *J Mol. Biol.* 389: 34-47.
Fitch CA, et al. (2002) Experimental pKa values of buried residues: analysis with continuum methods and role of Water penetration. *Biophysical Journal* 82: 3289-3304.

(Continued)

Primary Examiner — Suzanne M Noakes
(74) *Attorney, Agent, or Firm* — Ward and Smith, P.A.; Jeffrey W. Childers

(57) ABSTRACT

Internal polar and ionizable groups are essential for enzymatic catalysis, proton transport, redox reactions, and many other functional properties of proteins. To engineer novel enzymes or to modify the function of existing ones, and to build switches that can be used to modify the stability of proteins in response to changes in pH, it is necessary to introduce polar or ionizable groups or to modify the properties of existing ones. However, internal polar and ionizable groups usually destabilize proteins. The disclosure provides new methods that allow the introduction of polar and ionizable groups into the interior of proteins, as well as new methods for improving the accuracy of $pK_a$ of an internal amino acid of a protein, and methods for mapping the folding free energy landscape of a protein.

6 Claims, 22 Drawing Sheets

(56) References Cited

OTHER PUBLICATIONS

Ghosh N & Cui Q (2008) pKa of residue 66 in staphylococcal nuclease. I. Insights from QM/MM simulations with conventional sampling. *J Phys. Chem. B*. 112: 8387-8397.

Schutz CN & Warshel A (2001) What are the dielectric "constants" of proteins and how to validate electrostatic models? *Proteins: Structure, Function, and Genetics* 44: 400-417.

Zheng L, Mengen C, & Yang W (2008) Random walk in orthogonal space to achieve efficient free-energy simulation of complex systems. *Proc. Natl. Acad. Sci. USA* 105: 20227-20232.

Isom DG, et al. (2008) High tolerance for ionizable residues in the hydrophobic interior of proteins. *Proc. Natl. Acad. Sci. USA* 105: 17784-17788.

Thurlkill RL, Grimsley GR, Scholtz JM, & Pace CN (2006)Hydrogen Bonding Markedly Reduces the pK of Buried Carboxyl Groups in Proteins. *Journal of Molecular Biology* 362: 594-604.

Isom DG, et al. (2010) Charges in the hydrophobic interior of a protein. *Proc. Natl. Acad. Sci. USA* (in press).

Damjanovic A, Garcia-Moreno E. B, Lattman EE, & Garcia AE (2005) Molecular Dynamics Study of Water Penetration in Staphylococcal Nuclease. *Proteins: Structure Function and Bioinformatics* 60: 433-449.

Damjanovic A, et al. (2007) Role of flexibility and polarity as determinants of the hydration of internal cavities and pockets in proteins. *Biophysical Journal* 93: 2791-2804

Schlessman JL, et al, (2008) Crystallographic study of hydration of an internal cavity in engineered proteins with buried polar or ionizable groups. *Biophys. J.* 94: 3208-3216.

Ho M, Menetret J, Tsuruta H, & Allen KN (2009) The origin of the electrostatic perturbation in acetoacetate decarboxylase. *Nature* 459: 393-399.

Bone S & Pethig R (1982) Dielectric studies of the binding of water to lysozyme. *Journal of Molecular Biology* 157: 571-575.

Bone S & Pethig R ( 1985) Dielectric studies of protein hydration and hydration-induced flexibility. *Journal of Molecular Biology* 181: 323-326.

Gong H, Hocky G, & Freed KF (2008) Influence of nonlinear electrostatics on transfer energies between liquid phases: charge burial is far less expensive than Born Model. *Proc. Natl. Acad. Sci. USA* 105: 11146-11151.

Nguyen DM, Reynald RL, Gittis AG, & Lattman EE (2004) X-ray and thermodynamic studies of staphylococcal nuclease variants 192E and 192K: Insights into polarity of the protein interior. *J Mol. Biol.*: 565-574.

Karp DA, Stahley MR, & Garcia-Moreno E. B (2010) Conformational consequences of ionization of Lys, Asp, and Glu buried at position 66 in staphylococcal nuclease. *Biochemistry* 49: 4138-4146.

Chimenti MS, Castaneda CA, Majumdar A, & Garcia-Moreno E. B (2010) Structural origins of high apparent dielectric constants experienced by ionizable groups in the hydrophobic core of a protein. *J. Mol. Biol.* (in press).

Zheng Z & Sosnick TR (2010) Protein vivisection reveals elusive intermediates in folding. *J. Mol. Biol.* 397: 777-788.

Pey AL, et al. (2010) Modulation of buried ionizable groups in proteins with engineered surface charge. *J. Am. Chem. Soc.* 132: 1218-1219.

Simonson T & Perahia D (1995) Internal and Interfacial Dielectric Properties of Cytochrome c from Molecular Dynamics in Aqueous Solution. *Proceedings of the National Academy of Sciences of the United States of America* 92: 1082-1086.

Smith PE, Brunne RM, Mark AE, & Van Gunsteren WF (1993) Dielectric properties of trypsin inhibitor and lysozyme calculated from molecular dynamics simulations. *Journal of Physical Chemistry* 97: 2009-2014.

Simonson T & Brooks III CL (1996) Charge screening and the dielectric constant of proteins: Insights from molecular dynamics. *Journal of the American Chemical Society* 118:8452-8458.

Varadarajan R, Zewert TE, Gray HB & Boxer SG (1989) Effects of Buried Ionizable Amino Acids on the Reduction Potential of Recombinant Myoglobin. *Science* 243: 69-72.

Varadajaran R, Lambright DG, Boxer SG (1989) Electrostatic Interactions in Wild-Type and Mutant Recombinant Human Myoglobins. *Biochemistry* 28: 3771-3781.

Shortle D & Meeker A (1986) Mutant forms of staphylococcal nuclease with altered patterns of guanidine hydrochloride and urea denaturation. *Proteins: Structure, Function, and Genetics* 1: 81-89.

Whitten ST & Garcia-Moreno E. B (2000) pH dependence of stability of staphylococcal nuclease: Evidence of substantial electrostatic interactions in the denatured state. *Biochemistry* 39: 14292-14304.

Castaneda CA, et al. (2009) Molecular determinants of the pKa values of Asp and Glu residues in staphylococcal nuclease. *Proteins: Struct. Funct. Bioinf.* 77: 570-588.

Ihee, H. et al. Visualizing reaction pathways in photoactive yellow protein from nanoseconds to seconds. Proc. Natl. Acad. Sci. USA 102, 7145-7150 (2005).

Lanyi, J. K. Proton transfers in the bacteriorhodopsin photocycle. BBA Bioenergetics 1757, 1012-1018 (2006).

Pisliakov, A. V., Sharma, P. K., Chu, Z. T., Haranczyk, M. & Warshel, A. Electrostatic basis for the unidirectionality of the primary proton transfer in cytochrome c oxidase. Proc. Natl. Acad. Sci. USA 105, 7726-7731 (2008).

Chen, V. B. et al. MolProbity: all-atom structure validation for macromolecular crystallography. Acta Crystallogr. D 66, 12-21 (2010).

Chimenti, M. S., Castañeda, C. A., Majumdar, A. & García-Moreno E., B. Structural Origins of High Apparent Dielectric Constants Experienced by Ionizable Groups in the Hydrophobic Core of a Protein. J. Mol. Biol. 405, 361-377 (2011).

McCoy, A. J., Grosse-Kunstleve, R. W., Storoni, L. C. & Read, R. J. Likelihood-enhanced fast translation functions. Acta Crystallogr. D 61, 458-464 (2005).

Emsley, P. & Cowtan, K. Coot?: model-building tools for molecular graphics. Acta Crystallogr. D 60, 2126-2132 (2004).

Vaguine, A. A., Richelle, J. & Wodak, S. J. Sfcheck: a unified set of procedures for evaluating the quality of macromolecular structure-factor data and their agreement with the atomic model. Acta Crystallogr. D 55, 191-205 (1999).

Laskowski, R. A., MacArthur, M. W., Moss, D. S. & Thornton, J. M. Procheck: a program to check the stereochemical qualaity of protein structures. J. Appl. Crystallogr. 26, 283-291 (1993).

Sosnick, T. R. & Barrick, D. The folding of single domain proteins—have we reached a consensus? Curr. Opin. Struc. Biol. 21, 12-24 (2011).

Baldwin, R. L. The Search for Folding Intermediates and the Mechanism of Protein Folding.Annu. Rev. Biophys. 37, 1-21 (2008).

Chiti, F. et al. Mutational analysis of the propensity for amyloid formation by a globular protein. EMBO J. 19, 1441-1449 (2000).

Smith, D. P., Jones, S., Serpell, L. C., Sunde, M. & Radford, S. E. A Systematic Investigation into the Effect of Protein Destabilisation on Beta 2-Microglobulin Amyloid Formation. J. Mol. Biol. 330, 943-954 (2003).

Neudecker, P. et al. Structure of an Intermediate State in Protein Folding and Aggregation. Science 336,362-366 (2012).

Dul, J. L., Davis, D. P., Williamson, E. K., Stevens, F. J. & Argon, Y. Hsp70 and Antifibrillogenic Peptides Promote Degradation and Inhibit Intracellular Aggregation of Amyloidogenic Light Chains. J. Cell Biol. 152, 705-716 (2001).

Westerheide, S. D. & Morimoto, R. I. Heat Shock Response Modulators as Therapeutic Tools for Diseases of Protein Conformation. J. Biol. Chem. 280, 33097-33100 (2005).

Anfinsen, C.B. Principles that govern folding of protein chains. Science 181: 223-230 (1973).

Bailey, S. The CCP4 suite—programs for protein crystallography. Acta Crystallogr. D 50: 760-763 (1994).

Bouvignies, G. et al. Solution structure of a minor and transiently formed state of a T4 lysozyme mutant. Nature 477: 111-114 (2011).

Cannon, B. Thermodynamic consequences of substitution of internal positions in proteins with polar and ionizable residues. Johns Hopkins University, Ph.D. Thesis, (2008).

(56) References Cited

OTHER PUBLICATIONS

Delaglio, F. et al. NMRPipe: A multidimensional spectral processing system based on UNIX pipes. J. Biomol. NMR 6, 277-293 (1995).

Englander, S.W. Protein Folding Intermediates and Pathways Studied by Hydrogen Exchange. Annu. Rev. Bioph. Biom. 29: 213-238 (2000).

Goddard, T. and Kneller, D. Sparky 3. University of California, San Francisco.

Grzesiek, S., Anglister, J. and Bax, A. Correlation of Backbone Amide and Aliphatic Side-Chain Resonances in 13C/15N-Enriched Proteins by Isotropic Mixing of 13C Magnetization. J. Magn. Reson. B 101: 114-119 (1993).

Higgins, H.G. and Sharp, P.M. Fast and sensitive multiple sequence alignments on a microcomputer. CABIOS, 5:151-153 (1989).

Higgins, D.G., Bleasby, A.J., and Fuchs, R. Clustal V: improved software for multiple sequence alignment. Comput. Appl. Biosci. 8:189-191 (1992).

Grzesiek, S. & Bax, A. Correlating backbone amide and side chain resonances in larger proteins by multiple relayed triple resonance NMR. J. Am. Chem. Soc. 114, 6291-6293 (1992).

Painter, J. and Merritt, E.A. TLSMD web server for the generation of multi-group TLS models. J. Appl. Crystallogr. 39: 109-111 (2006).

Perutz, M.F. Stereochemistry of Cooperative Effects in Haemoglobin: Haem-Haem Interaction and the Problem of Allostery. Nature 228: 726-734 (1970).

Shortle, D., Meeker, A.K. and Freire, E. Stability mutants of staphylococcal nuclease: large compensating enthalpy-entropy changes for the reversible denaturation reaction. Biochemistry 27: 4761-4768 (1988).

Takayama Y., Castañeda C.A., Chimenti M., García-Moreno B., Iwahara J. Direct evidence for deprotonation of a lysine side chain buried in the hydrophobic core of a protein. J. Am. Chem. Soc. 130:6714-6715 (2008).

Von Ballmoos, C., Wiedenmann, A., and Dimroth, P. Essentials for ATP Synthesis by F1F0 ATP Synthases. Annu. Rev. Biochem. 78: 649-672 (2009).

Wiley, D.C. and Skehel, J.J. The Structure and Function of the Hemagglutinin Membrane Glycoprotein of Influenza Virus. Annu. Rev. Biochem. 56: 365-394 (1987).

Wittekind, M. and Mueller, L. HNCACB, a High-Sensitivity 3D NMR Experiment to Correlate Amide-Proton and Nitrogen Resonances with the Alpha- and Beta-Carbon Resonances in Proteins. J. Magn. Reson. B 101: 201-205 (1993).

Yamazaki, T., Yoshida, M., and Nagayama, K. Complete assignments of magnetic resonances of ribonuclease H from *Escherichia coli* by double- and triple-resonance 2D and 3D NMR spectroscopies. Biochemistry 32: 5656-5669 (1993).

Chimenti, M.S. et al. Structural reorganization triggered by charging of Lys Residues in the hydrophobic interior of a protein. Structure. vol. 20, Issue 6, Jun. 6, 2012, pp. 1071-1085.

Isom, D. et al. Large shifts in pKa values of lysine residues buried inside a protein. PNAS. 108(13), pp. 5260-5265, 2011.

Harms, M. et al. Arginine residues at internal positions in a protein are always charged. PNAS 108(47), pp. 18954-18959, 2011.

Hansen, D. F., Vallurupalli, P. & Kay, L. E. Using relaxation dispersion NMR spectroscopy to determine structures of excited, invisible protein states. J. Biomol. NMR 41, 113-120 (2008).

Bizzarri et al. Green fluorescent protein based pH indicators for in vivo use: a review. Analytical and Bioanalytical Chemistry, 393:1107-1122, 2009.

Rose, G. D., Fleming, P. J., Banavar, J. R. & Maritan, A. A backbone-based theory of protein folding. Proc. Natl. Acad. Sci. USA 103, 16623-16633 (2006).

Bai, Y., Sosnick, T., Mayne, L. & Englander, S. Protein folding intermediates: native-state hydrogen exchange. Science 269, 192-197 (1995).

\* cited by examiner

METHOD FOR INCORPORATING INTERNAL POLAR AND IONIZABLE GROUPS IN PROTEINS

FIELD OF THE DISCLOSURE

The disclosure relates generally to the field of protein engineering of novel enzymes and in modulating the activity of existing enzymes. More particularly, the disclosure relates to the stability and conformation of proteins, methods for the introduction of polar and ionizable amino acid groups into the interior of proteins, methods for determining the $pK_a$ of an internal amino acid of a protein, and methods for mapping the folding free energy landscape of a protein.

BACKGROUND OF THE DISCLOSURE

Under physiological conditions, proteins (polymer chains of peptide-linked amino acids) normally do not exist as extended linear polymer chains. A combination of molecular forces, including hydrogen bonding, hydrophilic and hydrophobic interactions, promote thermodynamically more stable secondary structures that can be highly organized (helices, beta pleated sheets, etc.). These structures can combine to form higher order structures with critical biological functions. Natural proteins are peptide-linked polymers containing 20 different amino acids, each with a different side-chain. The details of the folding into higher order structures are dependent on the type, frequency and primary sequence of the amino acids in the protein. Since each position in the polymer chain can be occupied by 20 different amino acids, the thermodynamic rules that describe the details of protein folding can be complex. For example, it is not yet possible to design a synthetic protein with a substrate-specific enzymatic site that is predicted by the primary amino acid sequence. More complete discussions of the structure and function of proteins are found in Dickerson et al. "The Structure and Action of Proteins" Harper and Row, New York, 1970 and Lehninger "Biochemistry" Worth, New York, 1970, pp. 109-146.

Some basic rules of protein folding have been discovered. In general, the side chains of the 20 L-amino acids commonly found in natural proteins can be placed in two categories: hydrophobic/non-polar and hydrophilic/polar, each playing separate roles in protein conformation. In the standard "oil drop" model for protein folding, the amino acids with more hydrophobic side chains (Val, Leu, Phe, Met, Ile) are sequestered to the inside of the protein structure, away from the aqueous environment. Frequently, these hydrophobic side chains form "pockets" that bind molecules of biological significance. On the other hand, hydrophilic amino acids (e.g. Lys, Arg, Asp, Glu) are most frequently distributed on the outer surface of natural proteins, providing overall protein solubility and establishing a superstructure for the internalized hydrophobic domains. Internal polar and ionizable groups are essential for enzymatic catalysis, proton transport, redox reactions, and many other functional properties of proteins. To engineer novel enzymes or to modify the function of existing ones, and to build switches that can be used to modify the stability of proteins in response to changes in pH, it is necessary to introduce polar or ionizable groups or to modify the properties of existing ones in the protein's interior region. Internal polar and ionizable amino acid groups however, usually destabilize proteins.

In computational biology, protein $pK_a$ calculations are used to estimate the $pK_a$ values of amino acids as they exist within proteins. These calculations complement the $pK_a$ values reported for amino acids in their free state, and are used frequently within the fields of molecular modeling, structural bioinformatics, and computational biology. $pK_a$ values of amino acid side chains play an important role in defining the pH-dependent characteristics of a protein. The pH-dependence of the activity displayed by enzymes and the pH-dependence of protein stability, for example, are properties that are determined by the $pK_a$ values of amino acid side chains. The $pK_a$ values of an amino acid side chain in solution is typically inferred from the $pK_a$ values of model compounds (i.e. compounds that are similar to the side chains of amino acids).

When a protein folds, the titratable amino acids in the protein are transferred from a solution-like environment to an environment determined by the 3-dimensional structure of the protein. For example, in an unfolded protein an aspartic acid typically is in an environment which exposes the titratable side chain to water. When the protein folds the aspartic acid may be buried deep in the protein interior with no exposure to solvent. In the folded protein the aspartic acid will be closer to other titratable groups in the protein and will also interact with permanent charges (e.g. ions) and dipoles in the protein. All of these effects alter the $pK_a$ value of the amino acid side chain, and $pK_a$ calculation methods generally calculate the effect of the protein environment on the model $pK_a$ value of an amino acid side chain. Typically the effects of the protein environment on the amino acid $pK_a$ value are divided into pH-independent effects and pH-dependent effects. The pH-independent effects (desolvation, interactions with permanent charges and dipoles) are added to the model $pK_a$ value to give the intrinsic $pK_a$ value. The pH-dependent effects cannot be added in the same straightforward way and have to be accounted for using Boltzmann summation, Tanford-Roxby iterations or other methods.

The interplay of the intrinsic $pK_a$ values of a system with the electrostatic interaction energies between titratable groups can produce quite spectacular effects such as non-Henderson-Hasselbalch titration curves and even back-titration effects. $pK_a$Tool provides an easy interactive and instructive way of playing around with these effects. Several software packages and webserver are available for the calculation of protein $pK_a$ values. Some methods are based on solutions to the Poisson-Boltzmann equation (PBE), often referred to as FDPB-based methods (FDPB is for "finite difference Poisson-Boltzmann"). The PBE is a modification of Poisson's equation that incorporates a description of the effect of solvent ions on the electrostatic field around a molecule. The H++ web server, the pKD webserver, MCCE and Karlsberg+ use the FDPB method to compute $pK_a$ values of amino acid side chains. FDPB-based methods calculate the change in the $pK_a$ value of an amino acid side chain when that side chain is moved from a hypothetical fully solvated state to its position in the protein. To perform such a calculation, one needs theoretical methods that can calculate the effect of the protein interior on a $pK_a$ value, and knowledge of the $pK_a$ values of amino acid side chains in their fully solvated states. A set of empirical rules relating the protein structure to the $pK_a$ values of ionizable residues have been developed by Li, Robertson, and Jensen. These rules form the basis for the web-accessible program called PROPKA for rapid predictions of $pK_a$ values.

Molecular dynamics methods of calculating $pK_a$ values involve computationally measuring the free energy difference between the protonated and deprotonated forms of the molecule. This free energy difference is measured using methods such as free-energy perturbation, thermodynamic integration and the Bennett acceptance ratio. Molecular dynamics is typically a much more computationally expensive way to predict $pK_a$'s than using the Poisson-Boltzmann equation. Currently used molecular force fields do not take polarizability into account, which could be an important property for protonation energies.

The pH value where the titratable group is half-protonated is equal to the $pK_a$ if the titration curve follows the Henderson-Hasselbalch equation. Most $pK_a$ calculation methods silently assume that all titration curves are Henderson-Hasselbalch shaped, and $pK_a$ values in $pK_a$ calculation programs are therefore often determined in this way. Some software developed for protein $pK_a$ calculations include: AccelrysPKA Accelrys CHARMm based $pK_a$ calculation; H++ Poisson-Boltzmann based $pK_a$ calculations; MCCE Multi-Conformation Continuum Electrostatics; Karlsberg+ $pK_a$ computation with multiple pH adapted conformations; pKD server $pK_a$ calculations and $pK_a$ value re-design; and PROPKA Empirical calculation of $pK_a$ values.

SUMMARY OF THE DISCLOSURE

The loss of stability related to the introduction of internal ionizable amino acid groups in proteins has plagued efforts in the engineering of novel enzymes. Internal ionizable and polar groups usually destabilize the folded (e.g. native) forms of proteins. It has generally been believed that it is not possible to introduce ionizable groups into the cores of proteins. By substituting 25 internal residues in a protein with acidic or basic amino acids, one at a time, it has been found that it is indeed possible to introduce internal ionizable groups into the hydrophobic interior of a protein. This has been made possible by increasing the stability of the protein before introducing the polar and ionizable groups. In addition, internal ionizable groups can be used to modify dramatically the stability and conformation of proteins in response to changes in pH.

It has been found that the relationship between the high thermodynamic stability of a protein and the ability to introduce acidic or basic residues into the protein interior, as well as the ability to ionize these residues without destroying the protein, and the ability to manipulate the stability of the protein and to make the stability pH sensitive, provides the basis for making switches, proton pumps, and novel enzymatic active sites for proteins.

Thus, in one embodiment the disclosure provides methods for incorporating internal polar and ionizable groups inside of proteins, the method comprising the steps of: a) increasing the thermodynamic stability of the protein; and b) incorporating polar and ionizable groups for hydrophobic groups inside the protein, thereby incorporating the internal polar and ionizable groups inside of the protein.

In another embodiment, the disclosure provides methods for stabilizing polar and ionizable groups inside of proteins, the method comprising the steps of: a) increasing the thermodynamic stability of the protein; and b) substituting polar and ionizable groups for hydrophobic groups inside the protein, thereby stabilizing the polar and ionizable groups inside the protein.

In another embodiment, the disclosure provides methods for stabilizing positive and negative charges inside of proteins, the method comprising the steps of: a) increasing the thermodynamic stability of the protein; and b) substituting polar and ionizable groups for hydrophobic groups inside the protein, thereby stabilizing the positive and negative charges inside the protein.

In another embodiment, the disclosure provides methods for rationally modifying the thermodynamic stability of a protein as a function of pH, the method comprising the steps of: a) increasing the thermodynamic stability of the protein; and b) incorporating polar and ionizable groups for hydrophobic groups inside the protein, thereby rationally modifying the thermodynamic stability of the protein as a function of pH.

In another embodiment, the disclosure provides methods for engineering pH sensitive conformational switches in proteins, the method comprising the steps of: a) increasing the thermodynamic stability of the protein; and b) incorporating polar and ionizable groups for hydrophobic groups inside the protein, thereby engineering the pH sensitive conformational switch in the protein.

In another embodiment, the disclosure provides methods for creating novel enzymatic sites in proteins, the method comprising the steps of: a) increasing the thermodynamic stability of the protein; and b) incorporating polar and ionizable groups for hydrophobic groups inside the protein, thereby creating the novel enzymatic site in the protein.

In another embodiment, the disclosure provides methods for modulating the $pK_a$ of an internal amino acid of a protein, the method comprising the steps of: a) increasing the thermodynamic stability of the protein; and b) incorporating polar and ionizable groups for hydrophobic groups inside the protein, thereby modulating the $pK_a$ of the internal amino acid of the protein.

In another embodiment, the disclosure provides methods for mapping the folding free energy landscape of a protein, the method comprising the steps of a) increasing the thermodynamic stability of the protein; and b) incorporating polar and ionizable groups for hydrophobic groups inside the protein, thereby mapping the folding free energy landscape of the protein.

In another embodiment, the disclosure provides methods for mapping the folding free energy landscape of a protein by using an internal ionizable amino acid to stabilize partially unfolded states, the method comprising the steps of: a) increasing the thermodynamic stability of the protein; b) incorporating polar and ionizable groups for hydrophobic groups inside the protein; c) hydrating the polar and ionizable groups to provide a hydrated modified protein; d) partially folding the hydrated modified protein to provide a partially folded hydrated modified protein; d) measuring the free energy distance between the partially folded state of the hydrated modified protein and the fully folded state of the protein; and e) repeating steps a) to d) to provide a map of the folded free energy landscape of the protein.

In another embodiment, the disclosure provides methods for calculating the $pK_a$ of an internal amino acid of a protein by: a) substituting an internal amino acid of the protein with an ionizable amino acid to provide a modified protein; b) hydrating the ionizable amino acid of the modified protein of step a) to provide a hydrated modified protein; c) folding the hydrated modified protein of step b) to provide a folded hydrated modified protein; d) titrating the folded hydrated modified protein of step c) with an acid or base to experimentally determine the $pK_a$ value of the ionizable amino acid in the modified protein; e) correlating the experimentally determined $pK_a$ value of the ionizable amino acid in the modified protein of step d) with the partially folded hydrated modified protein of step c); and f) using the correlated data of step e) to improve the accuracy of the structure-based $pK_a$ calculation of an internal amino acid of a protein.

The disclosure provides methods for designing proteins that require internal charges for function, and that to ensure that the proteins are fully functional involves increasing the free energy distance between the ground state and fully active protein and the partially or fully unfolded and inactive proteins. By increasing the stability of the protein it is possible to engineer the motifs requiring internal polar or charged groups for function. We provide the first estimate of the amount of stability required to bury acidic and basic residues, and the first estimates of the magnitudes of pKa shifts that are possible simply through the act of burying the ionizable groups in a protein, without the need to further engineer the local microenvironment around the ionizable group. Simply by being internal the ionizable groups achieve pKa values compatible with the proton transfer reactions central to catalysis and other proton-activated biological processes. In addition, by starting with enough stability we preclude partial or local unfolding. Further, the stability of a protein can be made highly sensitive to pH in a way that decreases stability with increasing pH (with internal acidic residues) or that decreases stability with decreasing pH (with internal basic residues). Finally, it has been found that by burying ionizable groups in proteins it is possible to engineer switches sensitive to small changes in pH.

DETAILED DESCRIPTION OF THE DISCLOSURE

Figure 1A:
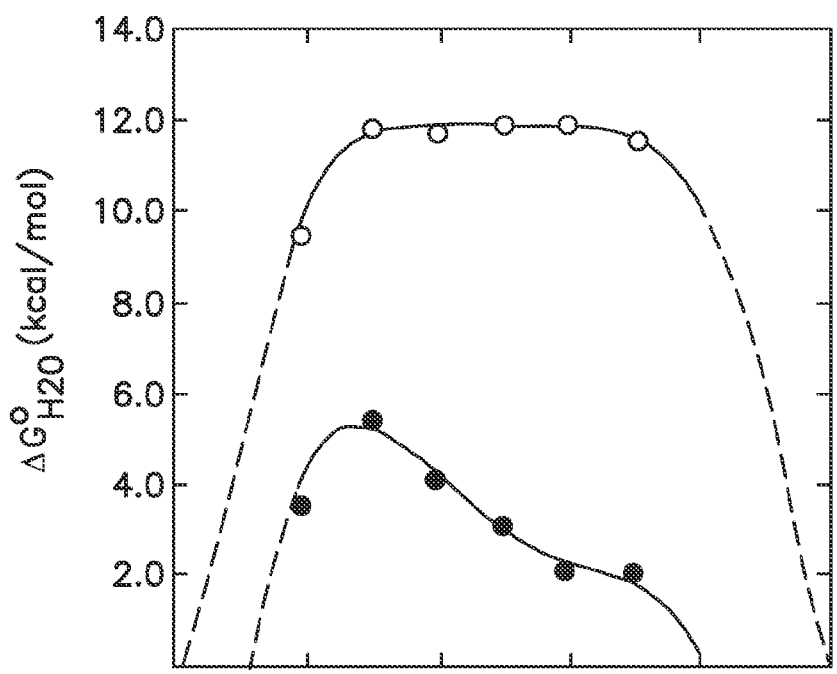
FIG. 1 shows the measurement of $pK_a$ values by analysis of pH dependence of thermodynamic stability, (a) Stability described in terms of Gibbs free energy ($\Delta G°_{H2O}$) of the background protein (○) and of a variant with Leu-25 substituted with Glu (•). All $\Delta G°_{H2O}$ were measured with GdnHCl denaturation monitored by Trp fluorescence as described previously[30]. The lines are meant to guide the eye (dashed line identifies the pH interval in which measurements of $\Delta G°_{H2O}$ are not accessible owing to acid or base unfolding), (b) Difference between the two curves in panel a (□), with reference to the left axis. The thin solid black curve represents the fit of equation 3 from Karp et al[16] to obtain the apparent $pK_a$ of Glu-25. The vertical arrows describe graphically the relationship between the $pK_a$ values in the native ($pK_a^N$) and unfolded ($pK_a^D$) states, and different regions of the $\Delta\Delta G°_{H2O}$ vs. pH curve. Also shown are H$^+$ titration curves for Glu-25 with $pK_a$ values of 4.7 (red) and 7.6 (blue) and the area between these two curves as a function of pH (green).

The disclosure is illustrated by the following exemplary embodiments, which are not to be construed in any way as imposing limitations on the scope thereof. On the contrary, various other embodiments, modifications, and equivalents thereof, which, after reading the description herein, may suggest themselves to those skilled in the art, may be made without departing from the spirit or the scope of the present disclosure. All publications, patents and patent applications disclosed herein are incorporated into this application by reference in their entirety.

In one embodiment the disclosure provides methods for incorporating internal polar and ionizable groups inside of proteins, the method comprising the steps of: a) increasing the thermodynamic stability of the protein; and b) incorporating polar and ionizable groups for hydrophobic groups inside the protein, thereby incorporating the internal polar and ionizable groups inside of the protein.

In one aspect the disclosure provides methods for incorporating internal polar and ionizable groups inside of proteins, wherein the thermodynamic stability of the protein is increased by about 3 to about 8 kcal/mol.

In another aspect the disclosure provides methods for incorporating internal polar and ionizable groups inside of proteins, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for incorporating internal polar and ionizable groups inside of proteins, wherein the protein is staphylococcal nuclease (SNase) or ribonuclease H (RNaseH).

In another aspect the disclosure provides methods for incorporating internal polar and ionizable groups inside of proteins, wherein the polar and ionizable amino acid of SNase is Lys-66, Glu-66 or Asp-66; and the hydrophobic amino acid of SNase is Val-66.

In another embodiment the disclosure provides methods for stabilizing polar and ionizable groups inside of proteins, the method comprising the steps of: a) increasing the thermodynamic stability of the protein; and b) substituting polar and ionizable groups for hydrophobic groups inside the protein, thereby stabilizing the polar and ionizable groups inside the protein.

In one aspect the disclosure provides methods for stabilizing polar and ionizable groups inside of proteins, wherein the thermodynamic stability of the protein is increased by about 3 to about 8 kcal/mol.

In another aspect the disclosure provides methods for stabilizing polar and ionizable groups inside of proteins, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for stabilizing polar and ionizable groups inside of proteins, wherein the protein is staphylococcal nuclease (SNase) or ribonuclease H (RNaseH).

In another aspect the disclosure provides methods for stabilizing polar and ionizable groups inside of proteins, wherein the polar and ionizable amino acid of SNase is Lys-66, Glu-66 or Asp-66; and the hydrophobic amino acid of SNase is Val-66.

In another embodiment the disclosure provides methods for stabilizing positive and negative charges inside of proteins, the method comprising the steps of a) increasing the thermodynamic stability of the protein; and b) substituting polar and ionizable groups for hydrophobic groups inside the protein, thereby stabilizing the positive and negative charges inside the protein.

In one aspect the disclosure provides methods for stabilizing positive and negative charges inside of proteins, wherein the thermodynamic stability of the protein is increased by about 3 to about 8 kcal/mol.

In another aspect the disclosure provides methods for stabilizing positive and negative charges inside of proteins, wherein the polar and ionizable groups are amino acids Mg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for stabilizing positive and negative charges inside of proteins, wherein the protein is staphylococcal nuclease (SNase) or ribonuclease H (RNaseH).

In another aspect the disclosure provides methods for stabilizing positive and negative charges inside of proteins, wherein the polar and ionizable amino acid of SNase is Lys-66, Glu-66 or Asp-66; and the hydrophobic amino acid of SNase is Val-66.

In another embodiment the disclosure provides methods for rationally modifying the thermodynamic stability of a protein as a function of pH, the method comprising the steps of: a) increasing the thermodynamic stability of the protein; and b) incorporating polar and ionizable groups for hydrophobic groups inside the protein, thereby rationally modifying the thermodynamic stability of the protein as a function of pH.

In one aspect the disclosure provides methods for rationally modifying the thermodynamic stability of a protein as a function of pH, wherein the thermodynamic stability of the protein is increased by about 3 to about 8 kcal/mol.

In another aspect the disclosure provides methods for rationally modifying the thermodynamic stability of a protein as a function of pH, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for rationally modifying the thermodynamic stability of a protein as a function of pH, wherein the protein is staphylococcal nuclease (SNase) or ribonuclease H (RNaseH).

In another aspect the disclosure provides methods for rationally modifying the thermodynamic stability of a protein as a function of pH, wherein the polar and ionizable amino acid of SNase is Lys-66, Glu-66 or Asp-66; and the hydrophobic amino acid of SNase is Val-66.

In another embodiment the disclosure provides methods for engineering pH sensitive conformational switches in proteins, the method comprising the steps of: a) increasing the thermodynamic stability of the protein; and b) incorporating polar and ionizable groups for hydrophobic groups inside the protein, thereby engineering the pH sensitive conformational switch in the protein.

In one aspect the disclosure provides methods for engineering pH sensitive conformational switches in proteins.

In another aspect the disclosure provides methods for engineering pH sensitive conformational switches in proteins, wherein the thermodynamic stability of the protein is increased by about 3 to about 8 kcal/mol.

In another aspect the disclosure provides methods for engineering pH sensitive conformational switches in proteins, wherein the polar and ionizable groups are amino acids Mg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for engineering pH sensitive conformational switches in proteins, wherein the protein is staphylococcal nuclease (SNase) or ribonuclease H (RNaseH).

In another aspect the disclosure provides methods for engineering pH sensitive conformational switches in proteins, wherein the polar and ionizable amino acid of SNase is Lys-66, Glu-66 or Asp-66; and the hydrophobic amino acid of SNase is Val-66.

In another embodiment the disclosure provides methods for creating novel enzymatic sites in proteins, the method comprising the steps of: a) increasing the thermodynamic stability of the protein; and b) incorporating polar and ionizable groups for hydrophobic groups inside the protein, thereby creating the novel enzymatic site in the protein.

In one aspect the disclosure provides methods for creating novel enzymatic sites in proteins, wherein the thermodynamic stability of the protein is increased by about 3 to about 8 kcal/mol.

In another aspect the disclosure provides methods for creating novel enzymatic sites in proteins, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for creating novel enzymatic sites in proteins, wherein the protein is staphylococcal nuclease (SNase) or ribonuclease H (RNaseH).

In another aspect the disclosure provides methods for creating novel enzymatic sites in proteins, wherein the polar and ionizable amino acid of SNase is Lys-66, Glu-66 or Asp-66; and the hydrophobic amino acid of SNase is Val-66.

In another embodiment the disclosure provides methods for modulating the $pK_a$ of an internal amino acid of a protein, the method comprising the steps of: a) increasing the thermodynamic stability of the protein; and b) incorporating polar and ionizable groups for hydrophobic groups inside the protein, thereby modulating the $pK_a$ of the internal amino acid of the protein.

In one aspect the disclosure provides methods for modulating the $pK_a$ of an internal amino acid of a protein, wherein the thermodynamic stability of the protein is increased by about 3 to about 8 kcal/mol.

In another aspect the disclosure provides methods for modulating the $pK_a$ of an internal amino acid of a protein, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for modulating the $pK_a$ of an internal amino acid of a protein, wherein the protein is staphylococcal nuclease (SNase) or ribonuclease H (RNaseH).

In another aspect the disclosure provides methods for modulating the $pK_a$ of an internal amino acid of a protein, wherein the polar and ionizable amino acid of SNase is Lys-66, Glu-66 or Asp-66; and the hydrophobic amino acid of SNase is Val-66.

In another embodiment the disclosure provides methods for mapping the folding free energy landscape of a protein, the method comprising the steps of: a) increasing the thermodynamic stability of the protein; and b) incorporating polar and ionizable groups for hydrophobic groups inside the protein, thereby mapping the folding free energy landscape of the protein.

In another embodiment the disclosure provides methods for mapping the folding free energy landscape of a protein, wherein the thermodynamic stability of the protein is increased by about 3 to about 8 kcal/mol.

In another aspect the disclosure provides methods for mapping the folding free energy landscape of a protein, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for mapping the folding free energy landscape of a protein, wherein the protein is staphylococcal nuclease (SNase) or ribonuclease H (RNaseH).

In another aspect the disclosure provides methods for mapping the folding free energy landscape of a protein, wherein the polar and ionizable amino acid of SNase is Lys-66, Glu-66 or Asp-66; and the hydrophobic amino acid of SNase is Val-66.

In another embodiment the disclosure provides methods for mapping the folding free energy landscape of a protein by using an internal ionizable amino acid to stabilize partially unfolded states, the method comprising the steps of: a) increasing the thermodynamic stability of the protein; b) incorporating polar and ionizable groups for hydrophobic groups inside the protein; c) hydrating the polar and ionizable groups to provide a hydrated modified protein; d) partially folding the hydrated modified protein to provide a partially folded hydrated modified protein; d) measuring the free energy distance between the partially folded state of the hydrated modified protein and the fully folded state of the protein; and e) repeating steps a) to d) to provide a map of the folded free energy landscape of the protein.

In one aspect the disclosure provides methods for mapping the folding free energy landscape of a protein by using an internal ionizable amino acid to stabilize partially unfolded states, wherein the thermodynamic stability of the protein is increased by about 3 to about 8 kcal/mol.

In another aspect the disclosure provides methods for mapping the folding free energy landscape of a protein by using an internal ionizable amino acid to stabilize partially unfolded states, wherein the polar and ionizable groups are amino acids Arg, His, Lys, Asp, Glu, Ser, Thr, Asn, Gln; Cys, Gly, or Pro; and the hydrophobic groups are amino acids Ala, Ile, Leu, Met, Phe, Trp, Tyr, or Val.

In another aspect the disclosure provides methods for mapping the folding free energy landscape of a protein by using an internal ionizable amino acid to stabilize partially unfolded states, wherein the protein is staphylococcal nuclease (SNase) or ribonuclease H (RNaseH).

In another aspect the disclosure provides methods for mapping the folding free energy landscape of a protein by using an internal ionizable amino acid to stabilize partially unfolded states, wherein the polar and ionizable amino acid of SNase is Lys-66, Glu-66 or Asp-66; and the hydrophobic amino acid of SNase is Val-66.

Charges in the Hydrophobic Interior of a Protein

Charges are inherently incompatible with hydrophobic environments. Presumably, for this reason, cores of folded proteins are comprised predominantly of clusters of hydrophobic side chains[1]. Ionizable groups are usually excluded from these internal hydrophobic environments and found instead at the protein surface, where they can interact with water[2]. Paradoxically, internal ionizable groups and internal charges in proteins play essential roles in fundamental biochemical processes involving proton ($H^+$) transport and electron ($e^-$) transfer[3-8]. This would appear to contradict the generally accepted notion that charges are incompatible with hydrophobic environments[9,10]. Here we show that charges are actually well tolerated in the hydrophobic interior of a protein, without the need for specialized structural adaptations to stabilize the charges, and without inducing conformational reorganization detectable with optical spectroscopy. This study involved measurement of the $pK_a$ values of Glu residues introduced with site-directed mutagenesis at 25 internal positions in a highly stable form of staphylococcal nuclease. 23 of the 25 Glu residues titrated with elevated $pK_a$ values, some even higher than 9, far above the normal $pK_a$ of 4.5 for Glu in water. The internal charges were tolerated because proteins behave inherently as a material with relatively high apparent polarizability. These results challenge conventional views of the architecture and electrostatic properties of proteins. They suggest a strategy for the design, and a pathway for the evolution of enzymes and other energy transducing proteins which emphasizes the enhancement of global stability over the tuning of local polarity and polarizability to stabilize internal charges.

The transfer of an ion from water into a less polar and polarizable environment, such as the hydrophobic interior of proteins, is energetically unfavorable. Internal charges usually destabilize the folded states of proteins, which is primarily why charged groups are largely excluded from the hydrophobic interior and found instead at the protein-water interface, where they can interact with bulk water[11]. Paradoxically, internal ionizable groups in proteins are essential for biological energy transduction. They are found in the active sites of enzymes[4,12], are necessary fore transfer and $H^+$ transport in proteins such as ATPase[7] and cytochrome c oxidase[6], for ion homeostasis[5,13], and for light-activated processes in proteins such as bacteriorhodopsin[8]. The structural adaptations necessary for proteins to tolerate internal ionizable groups, and the factors that stabilize internal charges, are poorly understood. This continues to limit our understanding of fundamental aspects of function and evolution of proteins, and has hindered our ability to manipulate and to design novel enzymes.

We have examined systematically the ability of a globular protein to tolerate charges at internal positions by substituting 25 internal positions in staphylococcal nuclease (SNase) with glutamic acid (Glu), one at a time. Crystal structures of variants of SNase with Glu, Asp, and Lys at the internal positions 66[14-17], 92[18] and 38[19] have confirmed that internal ionizable side chains engineered by substitution of internal hydrophobic amino acids with ionizable ones are, indeed, internal. Aware that substitution of internal hydrophobic positions with Glu is destabilizing, we performed the experiments using a highly stable form of SNase known as Δ+PHS, which has a stability of 11.8 kcal/mol at 298 K[16]. At pH 7, all the Glu-substituted variants were thermodynamically stable and their conformation monitored by far-UV CD at 222 nm and Trp fluorescence was comparable to that of the background protein[20] (Table 1).

TABLE 1

Apparent $pK_a$ values of Glu residues at 25 internal positions in SNase

| Position | $^a pK_a$ | $^b \epsilon_{app}$ | $^c \Delta G°_{ion}$ (kcal/mol) | $^d \Delta G°_{H2O}$ (kcal/mol) | $^e pH_{mid}$ FL | $^f pH_{mid}$ CD |
|---|---|---|---|---|---|---|
| V104E | 9.4 | 9.2 | 6.7 | 4.2 | 10.4 | 10.4 |
| L125E | 9.1 | 9.7 | 6.3 | 2.5 | 10.1 | 10.2 |
| I92E | 9.0 | 9.9 | 6.1 | 1.4 | 9.8 | 9.6 |
| L103E | 8.9 | 10.1 | 6.0 | 3.4 | 10.3 | 10.2 |
| L36E | 8.7 | 10.5 | 5.7 | 3.2 | 10.3 | 10.3 |
| V66E | 8.5 | 11.0 | 5.4 | 1.8 | 10.6 | 10.5 |
| V99E | 8.4 | 11.2 | 5.3 | 3.2 | 10.1 | 9.9 |
| V39E | 8.2 | 11.7 | 5.0 | 5.3 | 10.7 | 10.7 |
| A109E | 7.9 | 12.6 | 4.6 | 4.2 | 10.4 | 10.5 |
| V74E | 7.8 | 12.9 | 4.5 | 2.7 | 10.4 | 10.5 |
| A58E | 7.7 | 13.3 | 4.4 | 5.0 | 10.9 | 10.8 |
| T62E | 7.7 | 13.3 | 4.4 | 5.6 | 10.7 | 10.8 |
| N100E | 7.6 | 13.6 | 4.2 | 7.4 | 11.1 | 11.1 |
| L25E | 7.5 | 14.0 | 4.1 | 3.1 | 10.4 | 10.5 |
| F34E | 7.3 | 14.8 | 3.8 | 4.4 | 10.6 | 10.7 |
| I72E | 7.3 | 14.8 | 3.8 | 4.6 | 10.5 | 10.4 |
| V23E | 7.1 | 15.7 | 3.5 | 4.9 | 10.6 | 10.6 |
| Y91E | 7.1 | 15.7 | 3.5 | 3.7 | 10.6 | 10.6 |
| A132E | 7.0 | 16.2 | 3.4 | 3.7 | NA | 10.8 |
| L38E | 6.8 | 17.3 | 3.1 | 7.3 | 11.2 | 11.0 |
| T41E | 6.8 | 17.3 | 3.1 | 8.2 | 11.2 | 11.3 |
| A90E | 6.4 | 20.1 | 2.6 | 4.0 | 10.6 | 10.5 |
| L37E | 5.2 | 38.1 | 1.0 | 9.1 | 10.9 | 11.4 |
| G20E | 4.5 | 80.0 | 0.0 | 8.2 | 11.3 | 11.4 |
| N118E | 4.5 | 80.0 | 0.0 | 9.9 | 11.7 | 11.7 |

$^a$Apparent $pK_a$ values. Estimated error was 0.2 for all but Glu-37 and Glu-90, which have an estimated error of 0.5.
$^b$Apparent dielectric constant, calculated with equation 3 in Dwyer et al[14] using $\Delta G°_{ion}$.
$^c$Calculated as 1.36 * ($pK_a - pK_{a\,mod}$), assuming a $pK_{a\,mod}$ of 4.5. Estimated uncertainty, based on the uncertainty in apparent $pK_a$ is between 0.2 and 0.3 kcal/mol.
$^d$Thermodynamic stability of the protein at the apparent $pK_a$, measured by GdnHCl titration monitored by Trp fluorescence, as described previously[30]. Collectively, the experimental error of the reported free energies ranges from 0.1 and 0.4 kcal/mol.
$^e$Midpoint of the major base unfolding transition monitored by Trp fluorescence. In all cases, the experimental uncertainty is 0.1 pH units.
$^f$Midpoint of the major base unfolding transition monitored by CD. In all cases, the experimental uncertainty is 0.1 pH units.

Figure 1B:
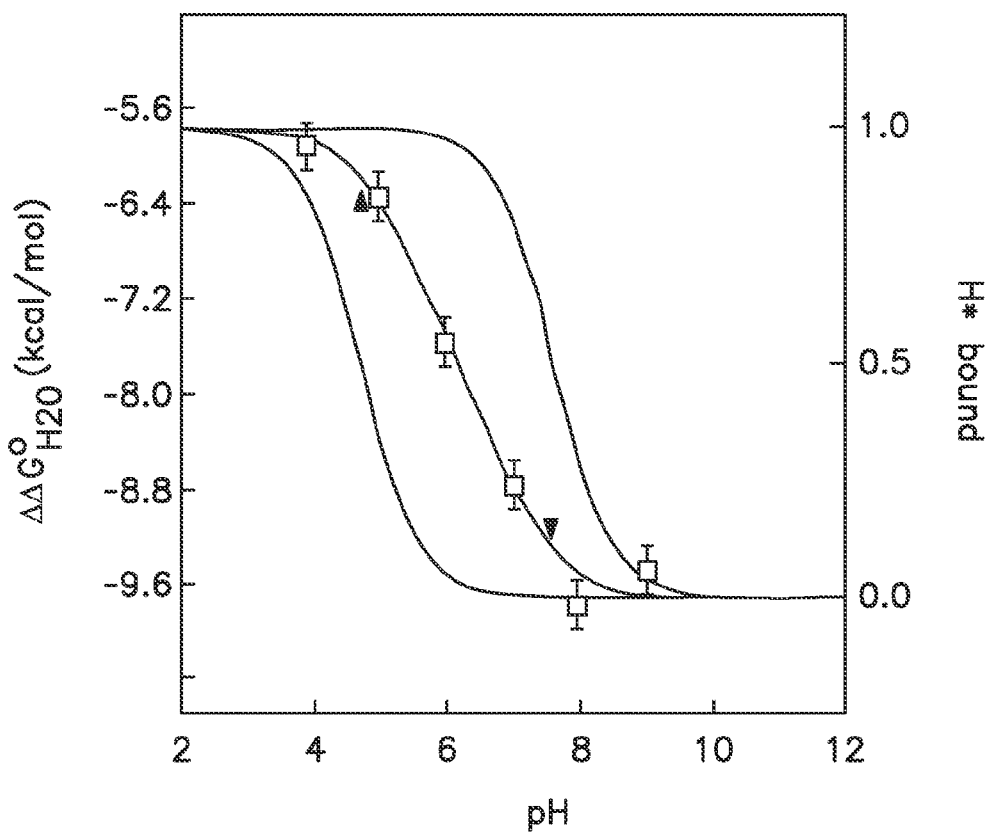

The apparent $pK_a$ values of the 25 Glu residues were obtained from the pH-dependence of the difference in thermodynamic stability ($\Delta\Delta G°_{H2O}$) between the background protein and the Glu-substituted proteins (FIG. 1)[14,17,19,21] (the $\Delta G°_{H2O}$ of each of the 25 variant proteins at each pH value is provided in Supporting Information). This was possible because the $pK_a$ values of internal Glu residues are highly perturbed. The red and blue curves in FIG. 1B correspond to H$^+$ titration of a representative internal Glu in the unfolded and native states of a protein, respectively. These curves were simulated using the $pK_a$ values obtained by analysis of the $\Delta\Delta G°_{H2O}$ vs. pH data shown in FIG. 1B. The midpoints of the H$^+$ titration curves in red and blue (FIG. 1B) represent the $pK_a$, they correspond to the regions with changing curvature in the $\Delta\Delta G°_{H2O}$ vs. pH curve (thin black in FIG. 1B). The area between these two titration curves, shown in green in FIG. 1B (with reference to the left axis) corresponds exactly to the $\Delta\Delta G°_{H2O}$ curve measured directly with chemical denaturation experiments (black curve and symbols in FIG. 1B). We refer to the $pK_a$ value obtained by analysis of $\Delta\Delta G°_{H2O}$ vs. pH data as the "apparent" $pK_a$ values because the analysis assumes that a single ionizable group with a highly perturbed $pK_a$ determines the $\Delta\Delta G°_{H2O}$ vs. pH curve. The validity of this assumption was tested earlier[14,16,39], and is supported by the known $pK_a$ values of all His, Asp and Glu residues in this protein[22,23].

The apparent $pK_a$ values of Glu residues at 23 of the 25 internal positions (FIG. 2A and Table 1) are higher than the normal $pK_a$ of 4.5 for Glu in water[23,24]. The direction of the shifts shows that the neutral state of the carboxylic groups is preferred over the charged one. This suggests that the dehydration experienced by the buried carboxylic side chains is not compensated completely by favorable interactions between the carboxylate moiety and polar groups or surface charges, or by polarization of their local microenvironments. As large as the measured shifts in $pK_a$ were, they are much smaller than would be expected if the protein interior behaved as a material with low dielectric constant near 2 or 4. Indeed, when the differences between the measured $pK_a$ values and the normal $pK_a$ of 4.5 for Glu in water were analyzed with a simple Born model (equation 3 in Dwyer et al.[14]) the apparent dielectric constants ($\epsilon_{app}$) reported by the internal carboxylic groups ranged from 9 to 38 (Table 1). These apparent dielectric constants should not be confused with the dielectric constant of the protein. They simply represent the values of the dielectric constant needed by a particular model (in this case, equation 3 in Dwyer et al.[14]) to reproduce the $pK_a$ values measured experimentally. The values of $\epsilon_{app}$ in Table 1 were calculated under the approximation that the shifts in $pK_a$ are governed solely by the dehydration of the buried charged groups and that the ionizable groups are buried infinitely far from bulk water. These $\epsilon_{app}$ are approximate and model dependent but they illustrate that the apparent polarizability reported by all internal Glu residues is very high. Even the lowest values of $\epsilon_{app}$ of 9.2, reported by Glu-104, already constitutes a high dielectric constant comparable to that of a highly polarizable material. Any other continuum dielectric model would yield equally high values of $\epsilon_{app}$.

Figure 2A:
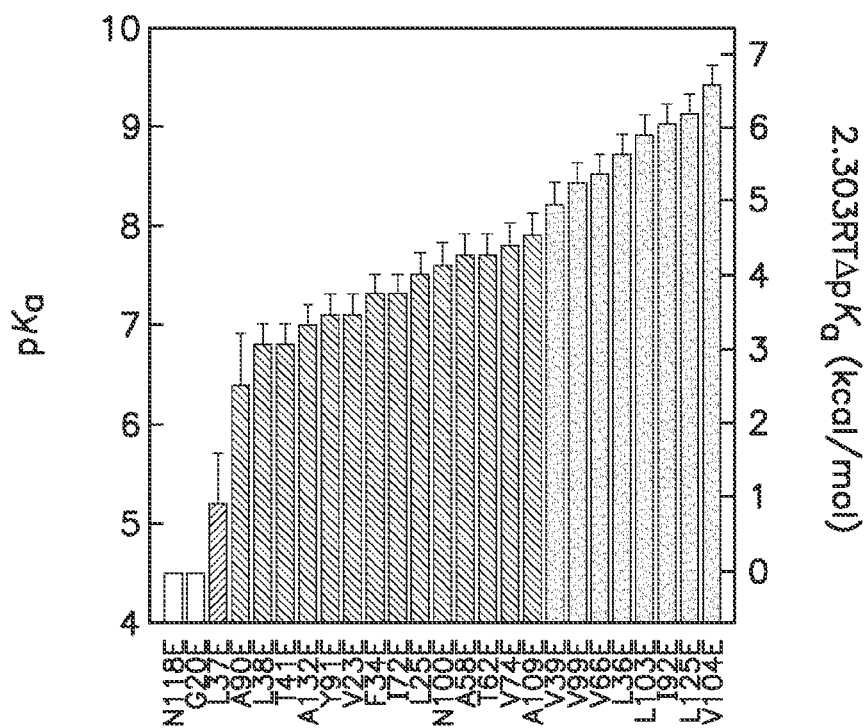
FIG. 2 shows the $pK_a$ values of Glu residues in 25 internal positions in staphylococcal nuclease, (a) Apparent $pK_a$ values. Color coding is only meant to guide the eye: white identifies groups with no measurable change in $pK_a$; green was used for groups with $pK_a$ between 4.5 to 6.5; light blue for groups with $pK_a$ between 6.5 to 8.0; dark blue for groups with $pK_a$ higher than 8.0. The right axis describes the $\Delta G°_{ion}$ values from Table 1. (b) Location of 25 internal positions coded with color according to the $pK_a$ for Glu in that position.
Figure 2B:
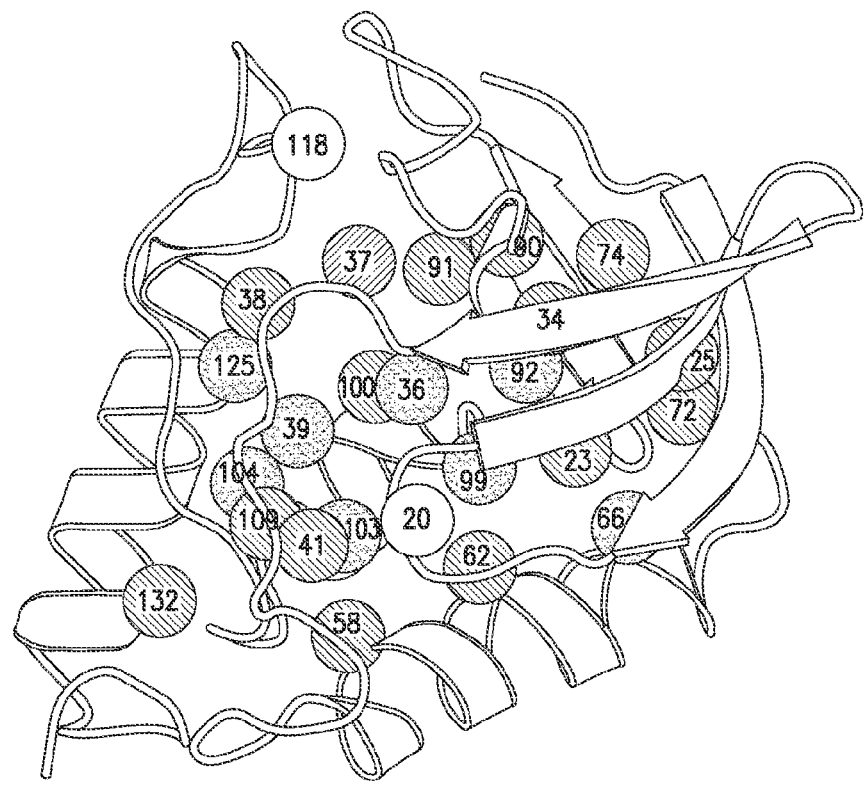

The structural and physical factors that determine the $pK_a$ values of internal groups in general are not well understood. The wide range of measured $pK_a$ values for internal Glu residues in SNase suggests that these factors differ significantly from location to location. However, no obvious correlation was observed between the magnitude of the shift in $pK_a$ and the location of the ionizable group (FIG. 2B). The $pK_a$ of Glu-118 and Glu-20 were normal or lower than normal, which was not surprising: Gly-20 is at a surface β-turn, therefore Glu-20 is probably in bulk water, and Glu-118 replaces Asn-118 so in all likelihood its microenvironment is already adapted to accept polar groups. In contrast to these two cases, the $pK_a$ values of several of the other Glu residues are shifted by almost 5 $pK_a$ units. These are among the largest shifts in $pK_a$ values measured experimentally. The shifts in most $pK_a$ values were large. The majority of the Glu residues were fully or at least partially neutral at pH 7. Most of the $pK_a$ values were in the range used by naturally occurring internal carboxylic groups to facilitate H$^+$ exchange reactions under physiological conditions.

Figure 3A:
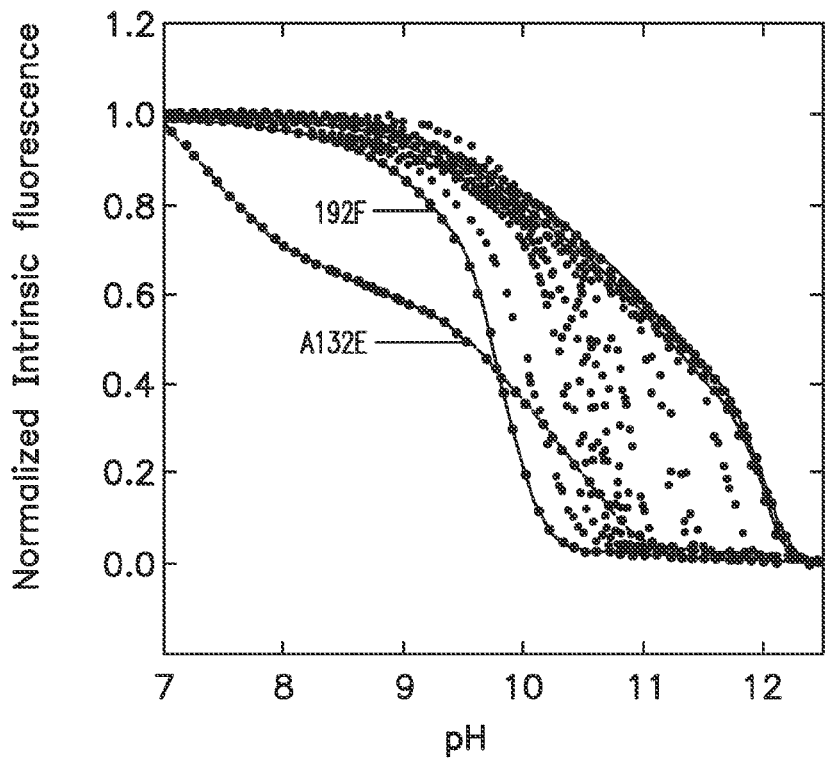
FIG. 3 shows the structural changes coupled to the ionization of internal Glu residues examined with Trp fluorescence and far-UV CD. (a) Base unfolding of variants with internal Glu monitored by Trp fluorescence, (b) Base unfolding of variants with internal Glu monitored by far UV CD measured at 222 nm. The solid black line (A) identifies the base unfolding profile of the background protein used to engineer the Glu-containing variants. The gray lines ( ) represent fits of equation 1 or 2 from Karp et al[16] to obtain the midpoints of major and minor structural transitions, described in Table 1 Blue lines identify cases where pre-denaturational transitions suggest partial structural changes coupled to the ionization of the internal Glu. Red lines identify the case where the titration of the internal group coincides with the major unfolding transition, (c) Location of Glu residues that promote partial unfolding (blue), global unfolding (red), or no conformational reorganization coupled to ionization (gray).
Figure 3B:
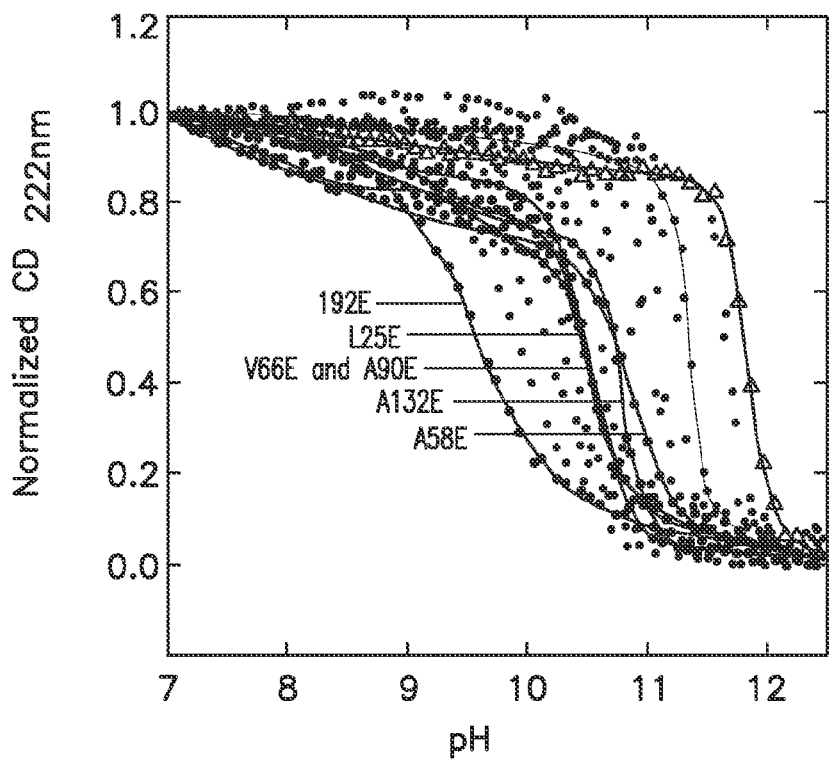

To examine the effects of ionization of internal Glu residues on the conformation of the native state of the protein, we monitored H⁺ titrations with Trp fluorescence and far UV-CD at 222 nm over the range of pH where most of the internal Glu residues titrate (FIGS. 3A and 3B). The majority of the variant proteins were fully folded and native-like at pH values as high as 9.5, which corresponds to the highest measured $pK_a$. The observation that the majority of the proteins with internal Glu residues tolerated the ionization of the internal Glu without undergoing any detectable, global conformational reorganization shows that charges can be tolerated in the interior of proteins, without the need for any specialized structural adaptations to stabilize the charge, even in a protein that did not evolve to use internal charges as part of its functional cycle. This inherent ability of proteins to withstand internal charges suggests that the relatively hydrophobic and dehydrated interior of proteins behaves as a material with high apparent polarity and polarizability. The physical and structural basis of this essential, inherent property of folded proteins is not understood and is currently under investigation. It may involve the penetration of water into the hydrophobic core[14,16,18,25], or very subtle structural rearrangement below the level of detection of optical spectroscopy[16] to stabilize the internal charges or to somehow expose them to water.

Figure 3C:
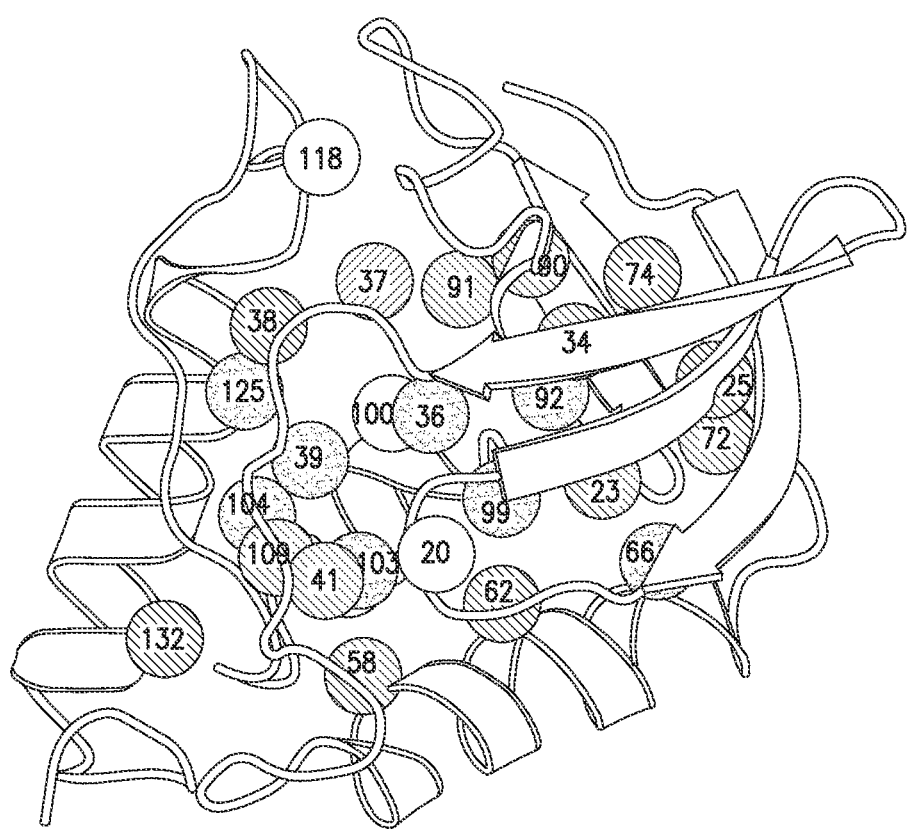

Only one variant (192E) out of the 25 that were studied was unfolded globally by the ionization of an internal Glu. The unfolding of the 192E variant is a consequence of both the high destabilization incurred by the substitution of Ile-92 with neutral Glu, and the large upwards shift in its $pK_a$. If the $pK_a$ of Glu-92 could be measured in an even more stable form of SNase, it would, in all likelihood, be even higher than the measured value of 9.0. Five other variants (L25E, A58E, V66E, A90E and, A132E) showed a modest but clear pre-denaturational transition in the range of pH where the internal Glu residues became charged (FIGS. 3A and 3B). These pH-dependent changes in the spectroscopic signals are consistent with a subtle and relatively minor conformational transition coupled to the ionization of the internal Glu. Some of the internal Glu residues that triggered local unfolding or reorganization are at the ends of elements of secondary structure, where fraying can occur (FIG. 3C). The possibility that the high apparent dielectric constants reflect local conformational reorganization of this type is being examined with NMR spectroscopy.

The $pK_a$ values show that at pH 7 most of the internal carboxylic groups were fully or at least partially neutral. At this pH the destabilization of the native state by substitution of internal hydrophobic groups with Glu is not the result of introduction of charge into a hydrophobic environment. It reflects the substitution of the hydrophobic group with neutral Glu and the attendant shift in $pK_a$. The actual cost of creating negative charge at the internal positions ($\Delta G°_{ion}$ in Table 1) was calculated from the difference between the apparent $pK_a$ and the normal $pK_a$ of 4.5 for Glu in water. The majority of the $\Delta G°_{ion}$ values range from 3.1 to 6.7 kcal/mol. These are large free energies, comparable to the net stability of most small globular proteins, but they are small compared to the free energy of dehydration of any ion or to the cost of transfer of an ion from water into a strictly hydrophobic material with a dielectric constant in the range 2 to 4[14,9,10,26]. This further demonstrates that the protein interior behaves as a material with high apparent polarizability. This high polarizability likely reflects contributions from factors that could stabilize the charged form of the internal Glu (i.e. interactions of the internal charge with surface charges, with dipoles, with the reaction field of bulk water, electronic polarization, conformational reorganization, water penetration, etc). The dielectric constant of folded proteins appears to be both sufficiently low to prevent the unnecessary burial of ionizable groups, which would destabilize the folded state and have potentially deleterious consequences, and sufficiently high to allow the presence of ionizable groups and charges in internal hydrophobic environments when necessary for function.

In enzymes and in proteins involved in H⁺ transport, the $pK_a$ values of ionizable groups that donate or accept H⁺ are tuned (e.g. depression of $pK_a$ for basic groups and elevation for acidic ones) to facilitate H⁺ transfer between them.[27] Our data suggest that the tuning of $pK_a$ values for functional purposes docs not require the evolution of dipolar cages or other specialized structural microenvironments[12]. The differences in the $pK_a$ values of the different internal Glu residues indicate there are subtle but measurable differences in the ability of different regions in the protein interior to respond to the presence of charge. However, the data in FIG. 2A show that at least in this highly stable form of SNase, simply by virtue of being internal, the $pK_a$ values of internal Glu residues are shifted into the range of $pK_a$ values used by naturally occurring carboxylic groups for H⁺ transport and other H⁺-activated biological processes. This suggests that the evolution of function in proteins that use internal ionizable groups might have been linked to the evolution of stability[28] more than to the evolution of special dynamics or structural microenvironments with high polarity or whatever other properties are necessary to tune $pK_a$ values for functional purposes. This also suggests a design strategy for the engineering of proteins with novel active sites and enzymatic functions that focuses on the enhancement of the stability of proteins to improve their ability to tolerate internal charge and internal ionizable groups with shifted $pK_a$ values.

The $pK_a$ values in Table 1 will enable unprecedented, stringent benchmarking of algorithms for structure-based calculation of $pK_a$ values and electrostatic energies in proteins. In general the calculation of $pK_a$ values of internal ionizable groups in proteins is extremely challenging. At present the calculations are not very accurate[9,26] because the molecular determinants of $pK_a$ values of internal groups are poorly understood and difficult to reproduce quantitatively with structure-based methods. From the experimental perspective the next challenge is to elucidate the physical and structural factors responsible for the high apparent polarizability of proteins. These data are necessary to guide the development of algorithms for structural analysis of the most fundamental biochemical process, such as catalysis and all processes based on H⁺-coupled e⁻ transfer.

Protein Engineering.

The Glu-containing variants of the Δ+PHS variant of SNase were prepared with QuikChange site-directed mutagenesis on a pET24A+ vector as described previously[16,20]. Purification was performed as described previously[29].

Stability Measurements.

Stability measurements were performed with guanidinium chloride titrations using an Aviv Automated Titration Fluorimeter 105 as described previously[30]. Linkage analysis of pH dependence of stability to obtain $pK_a$ values was performed as described previously[14,16,17].

Optical Spectroscopy.

pH titrations monitored with CD at 222 nm or with Trp fluorescence were performed with an Aviv Automated Titration Fluorimeter model 105 and with an Aviv circular dichroism spectrometer model 215, respectively. The experiments were performed with previously published protocols[30].

REFERENCES

Each of the following publications is incorporated herein by reference.
1. Perutz, M. F. et al., Structure of Haemoglobin: A Three-dimensional Fourier Synthesis at 5.5 A Resolution, Obtained by X-ray Analysis. Nature 185, 416 (1960).
2. Barlow, D. J. and Thornton, J. M., The distribution of charged groups in proteins. Biopolymers 25, 1717 (1986).
3. Kajander, T. et al., Buried charged surface in proteins. Structure Folding and Design 8, 1203 (2000).
4. Warshel, A, Energetics of Enzyme Catalysis. Proceedings of the National Academy of Sciences of the United States of America 75 (11), 5250 (1978).
5. Jiang, Y. et al., X-ray structure of a voltage-dependent K+ channel. Nature 423, 33 (2003).
6. Iwata, S., Ostermeier, C, Ludwig, B., and Michel, H., Structure at 2.9 A resolution of cytochrome c oxidase from *Paracoccus denitrificans*. Nature 376, 660 (2002).
7. Abrahams, J. P., Leslie, A. G. W., Lutter, R., and Walker, J. E., Structure at 2.8 A resolution of F1-ATPase from bovine heart mitochondria. Nature 370, 621 (1994).
8. Pebay-Peyroula, E., Rummel, G., Rosenbusch, J. P., and Landau, E. M., X-ray structure of bacteriorhodopsin at 2.5 A from microcrystals grown in lipidic cubic phases. Science 277 (277), 1676 (1997); Luecke, H, Richter, H. T., and Lanyi, J. K., Proton transfer pathways in bacteriorhodopsin at 2.3 angstrom resolution. Science 280, 1934 (1998).
9. Schutz, Claudia N. and Warshel, Arieh, What are the dielectric "constants" of proteins and how to validate electrostatic models? Proteins: Structure, Function, and Genetics 44, 400 (2001).
10. Parsegian, A., Energy of an ion crossing a low dielectric membrane: solutions to four relevant electrostatic problems. Nature 221, 844 (1969).
11. Perutz, M. F., Kendrew, J. C, and Watson, H. C, Structure and function of haemoglobin: II. Some relations between polypeptide chain configuration and amino acid sequence. J. Mol. biol. 13, 669 (1965).
12. Warshel, A, Aqvist, J., and Creighton, S., Enzymes Work by Solvation Substitution Rather Than by Desolvation. Proceedings of the National Academy of Sciences of the United States of America 86 (15), 5820 (1989).
13. Doyle, D. A. et al., The Structure of the Potassium Channel: Molecular Basis of K+ Conduction and Selectivity. Science 280, 69 (1998).
14. Dwyer, J J et al., High apparent dielectric constants in the interior of a protein reflect water penetration. Biophysical Journal 79(3), 1610 (2000).
15. Garcia-Moreno E., B et al., Experimental measurement of the effective dielectric in the hydrophobic core of a protein. Biophysical Chemistry 64 (1-3), 211 (1997).
16. Karp, D. A. et al., High Apparent Dielectric Constant Inside a Protein Reflects Structural Reorganization Coupled to the Ionization of an Internal Asp. Biophysical Journal 92, 2041 (2007).
17. Stites, Wesley E., Gittis, Apostolos G., Lattman, Eaton E., and Shortle, David, In a staphylococcal nuclease mutant the side-chain of a lysine replacing valine 66 is fully buried in the hydrophobic core. Journal of Molecular Biology 221, 7 (1991).
18. Nguyen, D M, Reynald, R L, Gittis, A. G., and Lattman, E. E., X-ray and thermodynamic studies of staphylococcal nuclease variants I92E and I92K: Insights into polarity of the protein interior. J. Mol. Biol. (341), 565 (2004).
19. Harms, M. J. et al., The $pK_a$ values of acidic and basic residues buried at the same internal location in a protein are governed by different factors. J. Mol. Biol. 389, 34 (2009); Harms, M. J. et al., A buried lysine that titrates with a normal $pK_a$: Role of conformational flexibility at the protein water interface as a determinant of $pK_a$ values. Protein Science 17, 833 (2008).
20. Isom, D. G. et al., High tolerance for ionizable residues in the hydrophobic interior of proteins. Proc. Natl. Acad. Sci. USA 105, 17784 (2008).
21. Fitch, C. A. et al., Experimental $pK_a$ values of buried residues: analysis with continuum methods and role of water penetration. Biophysical Journal 82, 3289 (2002).
22. Castaneda, C. A. et al., Molecular determinants of the $pK_a$ values of Asp and Glu residues in staphylococcal nuclease. Proteins: Struct. Fund. Bioinf, 1 (2009).
23. Lee, K. K., Fitch, C. A, Lecomte, J. T. J., and Garcia-Moreno E., B., Electrostatic effects in highly charged proteins: salt sensitivity of $pK_a$ values of histidines in staphylococcal nuclease. Biochemistry 41, 5656 (2002).
24. Matthew, James B. et al., pH-dependent properties in proteins. CRC Crit. Rev Biochem 18(2), 91 (1985).
25. Schlessman, J. L. et al., Crystallographic study of hydration of an internal cavity in engineered proteins with buried polar or ionizable groups. Biophys. J. 94, 3208 (2008).
26. Warshel, A, Sharma, P. K., Kato, M., and Parson, W. M., Modeling electrostatic effects in proteins. Biochimica et Biophysica Acta 1764, 1647 (2006).
27. Gunner, M R and Alexov, E, A pragmatic approach to structure based calculation of coupled proton and electron transfer in proteins. Biochimica et Biophysica Acta 1458 (1), 63 (2000).
28. Bloom, J. D., Labihavikul, S. T., Otey, C. R., and Arnold, F. H., Protein stability promotes evolvability. Proc. Natl. Acad. Sci. USA 103, 5869 (2006); Tokuriki, N., Stricher, F., Serrano, L., and Tawfik, D., How protein stability and new functions trade off. PLoS Computational Biology A, 1 (2008).
29. Shortle, D and Meeker, A K, Mutant forms of staphylococcal nuclease with altered patterns of guanidine hydrochloride and urea denaturation. Proteins: Structure, Function, and Genetics 1, 81 (1986).
30. Whitten, S. T. and Garcia-Moreno E., B, pH dependence of stability of staphylococcal nuclease: Evidence of substantial electrostatic interactions in the denatured state. Biochemistry 39 (46), 14292 (2000).

Large Shifts in $pK_a$ Values of Lysine Residues at 25 Internal Positions in a Protein Internal ionizable groups in proteins are relatively rare but essential for function. Owing to the large differences in the polarity and polarizability of water and the protein interior, they usually titrate with highly perturbed $pK_a$ values. The molecular determinants of these $pK_a$ values are poorly understood. To examine this issue we measured the $pK_a$ values of 25 internal Lys residues engineered by substitution of 25 internal positions in a highly stable form of staphylococcal nuclease. Nineteen of these Lys residues have depressed $pK_a$ values, some as low as 5.3. Only six Lys residues have normal $pK_a \geq 10$. The structural consequences of ionization of the internal Lys residues were examined with pH titrations monitored with far-UV CD and by Trp fluorescence. One variant (I92K) was unfolded by the ionization of the internal Lys. In four variants (V66K, N100K, V104K, L125K) the ionization of the internal Lys triggered local or partial unfolding. The remaining 20 variants are fully folded under conditions of pH where the internal Lys residues are charged. There is evidence that some of the internal Lys residues interact with surface charges. The magnitude of the shifts in $pK_a$ values, and the demonstration that a protein is inherently able to withstand the presence and ionization of internal basic groups without significant structural reorganization, suggest that this protein behaves as a material with relatively high apparent polarizability. At present the origins of this high polarizability are not understood. The $pK_a$ values of the internal lysines will enable benchmarking and unprecedented critical assessment of computational methods for structure-based $pK_a$ calculations.

Internal ionizable groups in proteins play important functional roles in many biochemical processes, especially in proteins used for energy transduction. They are essential for catalysis, in ion transport and water homeostasis, in many light activated processes, and in electron (e⁻) transfer and proton (H⁺) transport. Internal ionizable groups have unusual properties that, despite their importance, are still poorly understood. The $pK_a$ values of internal groups are governed by the polarity and polarizability inside a protein, which are lower than in bulk water. Because charges buried in proteins are usually not as well stabilized by protein as they are by water, the $pK_a$ values of internal groups can be much different from the normal $pK_a$ values in water (1). The trend is for the $pK_a$ of internal groups to be higher than normal for acidic groups (2-4) and lower than normal for basic groups (5-7). It is of interest to understand the molecular determinants of internal groups. Computational methods are not useful for this purpose because structure-based calculation of $pK_a$ values of internal groups cannot be performed reliably (1, 8, 9).

The $pK_a$ of Lys, Glu, and Asp at internal positions 66 (2, 4-7), 92 (10) and 38 (3, 11) in a highly stable form of staphylococcal nuclease (SNase) were described previously. In crystal structures the ionizable side chains are truly internal. At positions 66 and 92 they are buried deeply in the hydrophobic core of the protein. The $pK_a$ values of the ionizable groups at these two positions are shifted significantly relative to the normal $pK_a$ values in water. The side chain of residues at position 38 are closer to the protein-water interface. Asp-38 and Glu-38 have perturbed $pK_a$ values but Lys-38 titrates with a normal $pK_a$ even though its side chain is buried.

To examine systematically the molecular determinants of $pK_a$ values of internal ionizable groups it was first necessary to measure many $pK_a$ values and to define the range of values that are possible in the different types of microenvironments inside a protein. To this end we engineered variants of SNase with Lys, Arg, Asp and Glu at 25 internal positions (12). The substitution of internal hydrophobic positions with ionizable groups is always destabilizing, as expected. To demonstrate that the ability of SNase to withstand these substitutions is not a property unique to SNase, internal positions in ribonuclease H (RNaseH), which also has high stability but with a completely different fold, were also substituted with Glu and Lys (12). The energetic cost of substitutions in SNase and RNaseH were comparable, demonstrating that core hydrophobic residues in proteins can be substituted with ionizable ones in any protein that has a sufficiently high initial stability.

The $pK_a$ values of the 25 internal Glu residues have been measured (13). With two exceptions, the $pK_a$ values were all higher than the normal $pK_a$ of 4.5 for Glu and water. Some Glu residues had a $pK_a$ of 9 or higher. Trp fluorescence and far-UV CD at 222 nm showed that in 19 of the 25 variants the ionization of the internal Glu residues did not trigger any conformational change detectable. One variant unfolded globally when the internal Glu was ionized, and five underwent local or partial unfolding. The demonstration that SNase can withstand the ionization of internal Glu residues was surprising in light of the presumed incompatibility of charges and hydrophobic environments. The magnitude of the shifts in $pK_a$ values of the internal Glu residues in SNase is consistent with the behavior expected from a material with high apparent polarizability.

We have now examined the properties of Lys side chains at the 25 internal positions in SNase. The effects of pH on stability of the 25 variants were measured with chemical denaturation monitored by Trp fluorescence. The $pK_a$ values of the 25 internal Lys residues were measured. Acid/base titrations were monitored with Trp fluorescence and far-UV CD to detect conformational reorganization coupled to the ionization of the internal Lys residues.

If the fundamental assumptions inherent to continuum electrostatics are valid for studies of electrostatics in the protein interior, the properties of the internal Lys and Glu side chains should be comparable as the dielectric response triggered by a positive and a negative charge are comparable in the coarse-grained continuum approximation. We did not really anticipate that positive and negative charges at the same internal location in a protein would have comparable properties. The charge in Lys is centered in one atom whereas in Glu it is delocalized, therefore their hydration properties should be different. Furthermore, the hydrogen bonds of the polar moieties of the Lys and Glu side chains are not equivalent. In general the carboxylic side chain is better hydrated that the amino group, even in internal locations secluded from bulk water (14-16).

The $pK_a$ values of the internal Lys residues in SNase contribute novel insight into origins of the dielectric properties in the interior of a protein. They also enable systematic studies of molecular determinants of $pK_a$ values of internal groups. The data described here will allow unprecedented, critical evaluation of the accuracy of computational methods for structure-based calculation of electrostatic effects and $pK_a$ values in proteins (1).

All experimental studies were performed with a highly stable variant of SNase referred to as Δ+PHS after the deletion and substitutions used to engineer the protein. The high thermodynamic stability of 11.8 kcal/mol (pH 7, 298 K, 0.1 M ionic strength) was necessary to maximize the range of pH over which the protein stayed folded. The high stability was also necessary to allow measurement of energetic consequences of substitution of hydrophobic positions with internal ionizable groups (12).

Measurement of $pK_a$ Values from the pH Dependence of Stability.

The measurement of $pK_a$ values by analysis of the pH dependence of thermodynamic stability ($\Delta G°_{H2O}$) requires analysis of the difference ($\Delta\Delta G°_{H2O}$) between the stability of a background protein (Δ+PHS nuclease) and of the variant with the internal ionizable group of interest (FIG. 4). All stability measurements were performed with GdnHCl denaturation monitored with Trp fluorescence.

Figure 4A:
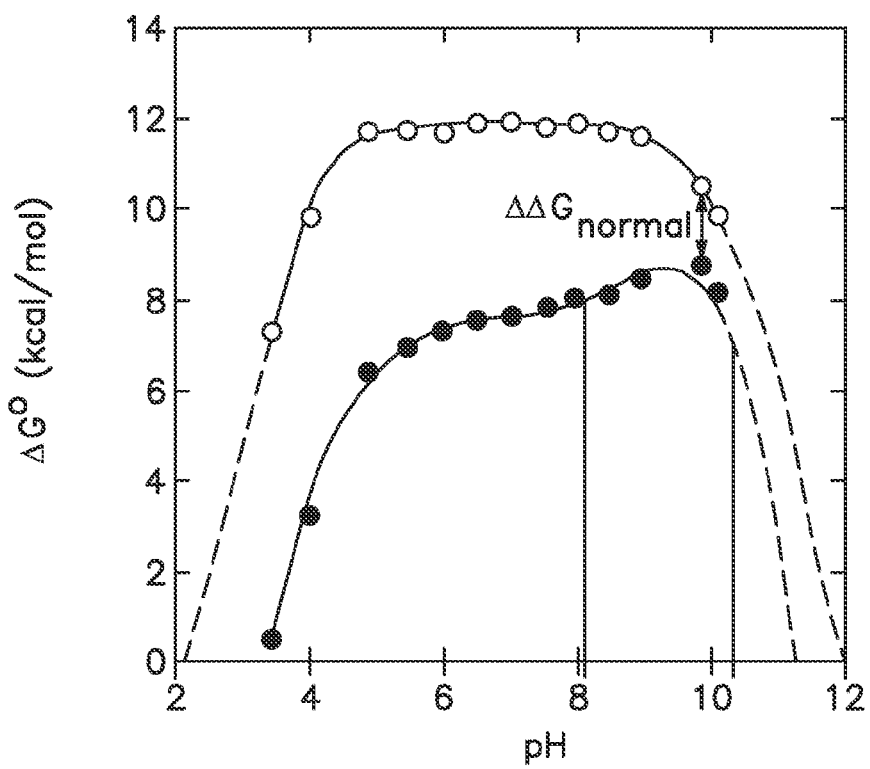
FIG. 4 shows the measurement of $pK_a$ values through linkage analysis of the pH dependence of thermodynamic stability, (A) Thermodynamic stability ($\Delta G°_{H2O}$) of background protein ($\Delta$+PHS nuclease) (○) and its L125K variant (•) measured by GdnHCl denaturation monitored by Trp fluorescence. The line is from a simulation and it is only meant to guide the eye. $\Delta\Delta G_{neutral}$ identifies the pH at which the different in $\Delta G°_{H2O}$ between the two proteins is dominated by the cost of substitution of Leu-125 with Lys in the neutral state. (B) Difference in thermodynamic stability of $\Delta$+PHS and the L125K variant (variant—background). The line describes the fit of Equation 1 to the data. $\Delta G°_c$ refers to the difference in stability that is pH independent. The $pK_a$ of Lys-125 in native ($pK_a^N$) and denatured ($pK_a^D$) states are marked on the graph. (C) Thermodynamic stability of $\Delta$+PHS nuclease (○) and of its T62K variant (•) measured by GdnHCl denaturation monitored by Trp fluorescence. The line is from a simulation and it is only meant to guide the eye. (D) Difference in thermodynamic stability of $\Delta$+PHS and the T62K variant (variant—background). The line describes the fit of Equation 2 to the data. $pK_a^N$ identifies the $pK_a$ of Lys-62.
Figure 4B:
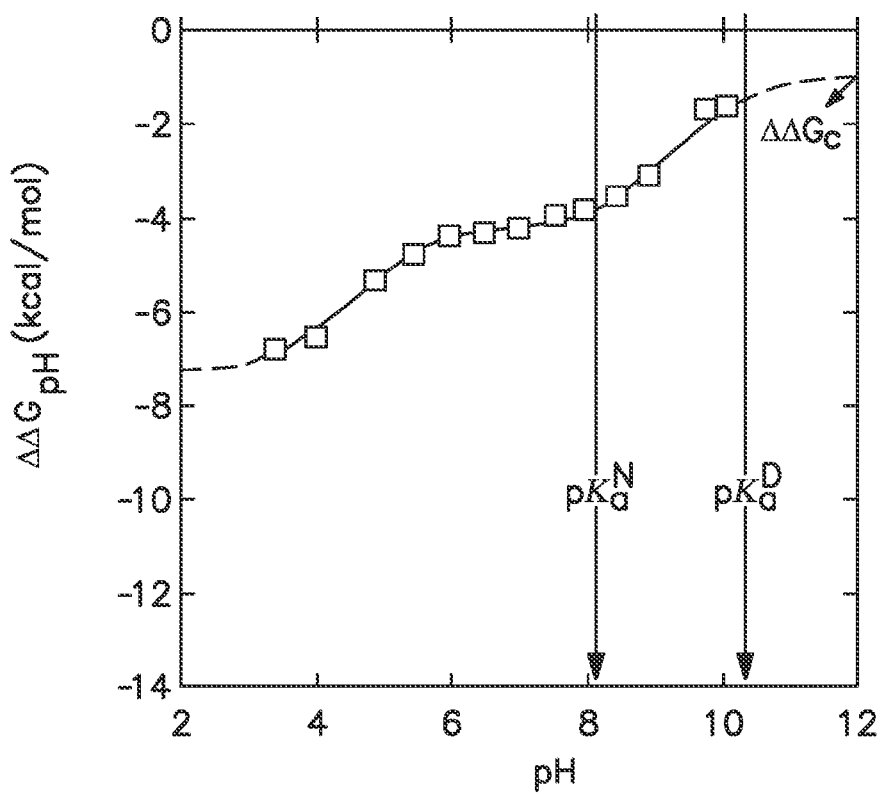

In most cases the difference stability ($\Delta\Delta G°_{H2O}$) vs. pH curve was governed by the substantial depression in the $pK_a$ of the internal Lys residues (FIGS. 4A and 4B). This is evident from the slope of the $\Delta\Delta G°_{H2O}$ vs. pH curve (FIG. 4B), which approaches 1.36 kcal/mol in the linear region. This has also been corroborated by measurement of the $pK_a$ of internal ionizable group with different equilibrium thermodynamic methods (2, 4-6), including NMR spectroscopy (3, 11), and by knowledge of the p$K_a$ of all other ionizable groups that titrate in the pH range of interest (17, 18). When the $\Delta\Delta G°_{H2O}$ vs. pH curve appeared to be determined by the shift in the p$K_a$ value of a single internal Lys, the curve was analyzed by fitting a general linkage relationship in which the pH dependence of $\Delta G°_{H2O}$ is accounted for by a shift in the p$K_a$ of a single titratable group.

Figure 4C:
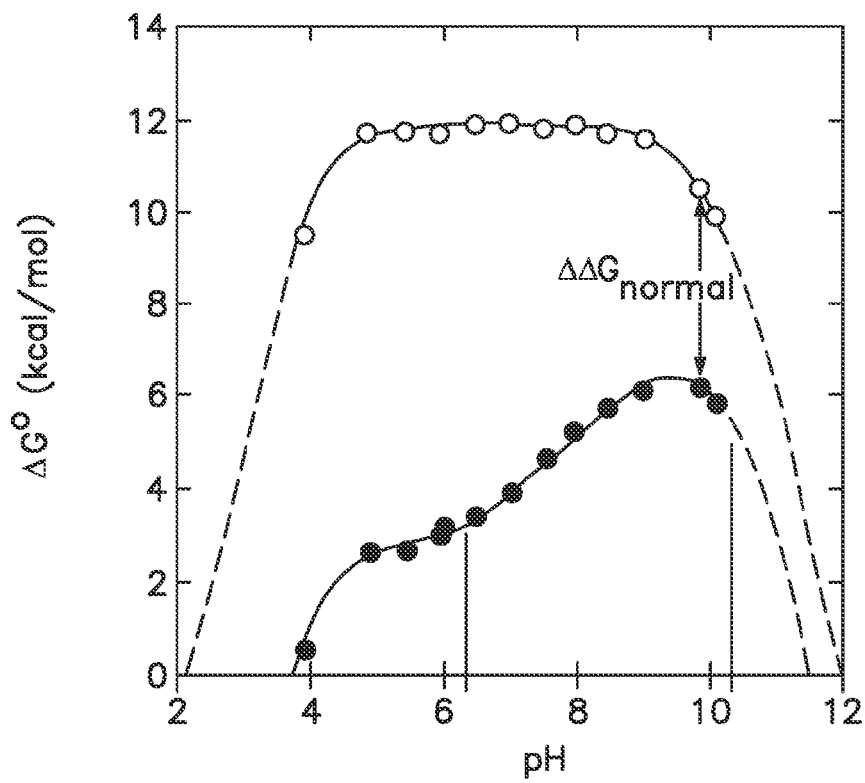
Figure 4D:
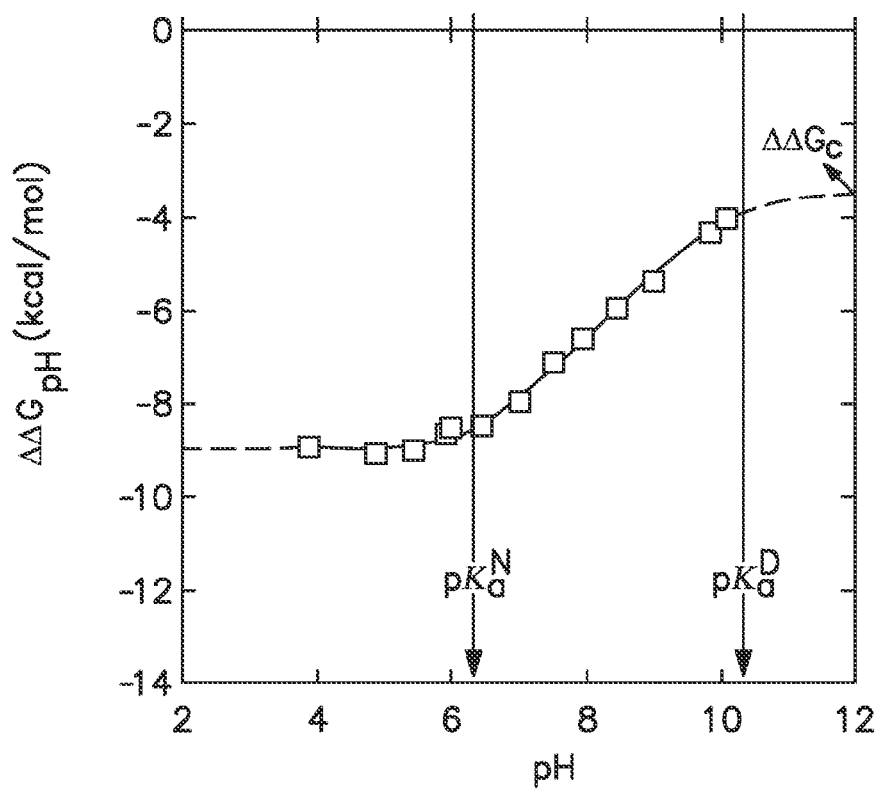

In 9 of the SNase variants with internal Lys residues the $\Delta\Delta G°_{H2O}$ vs. pH curve showed clear evidence of contributions from two or more ionizable groups whose p$K_a$ are affected by the ionization of the internal Lys (FIGS. 4C and 4D). In these cases the p$K_a$ of the internal Lys residue was obtained by analysis of $\Delta\Delta G°_{H2O}$ vs. pH curve with a more complex linkage relationship that attempted to resolve phenomenologically the contributions to the $\Delta\Delta G°_{H2O}$ vs. pH curve by shifts in the p$K_a$ of two groups. The higher of the two p$K_a$ values resolved with a two-site linkage equation was assigned to the internal Lys of interest. The validity of this interpretation has been corroborated by NMR spectroscopy experiments in our laboratory that identified the surface Asp and Glu residues whose p$K_a$ values are affected by the ionization of internal Lys residues.

p$K_a$ Values of 25 Internal Lys Residues.

Figure 5A:
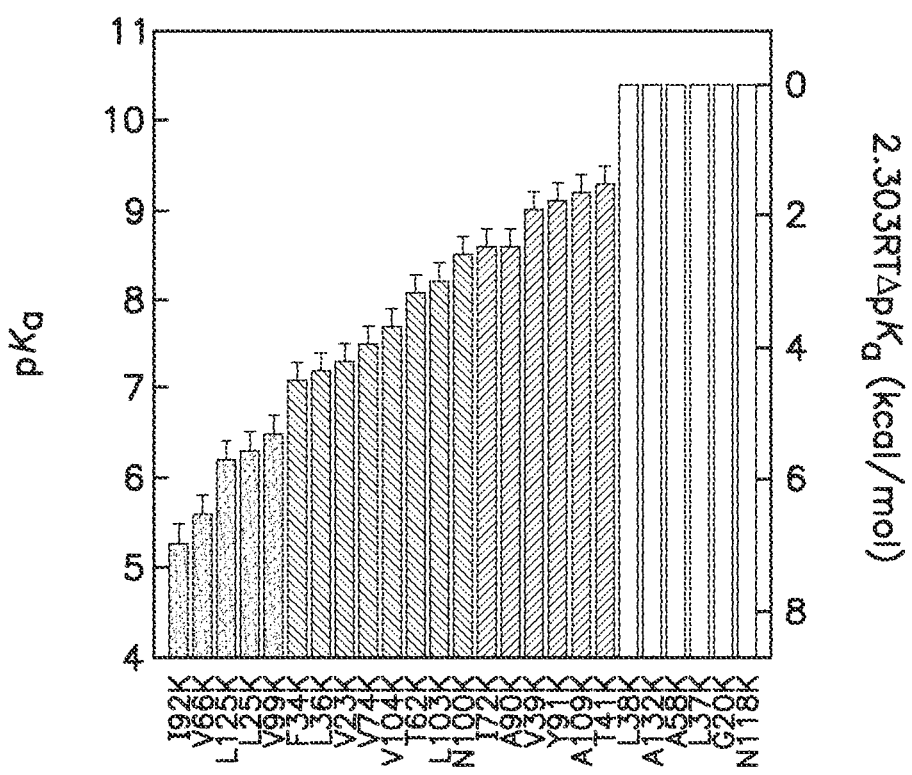
FIG. 5 shows the $pK_a$ values of Lys at 25 internal positions. (A) $pK_a$ values. White bars identify groups that do not exhibit a detectable shift in $pK_a$ value. Colors are only meant to separate the groups into those with small, medium and large shifts in $pK_a$ values. (B) Distribution of internal Lys residues in the structure of $\Delta$+PHS nuclease (PDB accession code 3bdc (17)) (REF), color coded according to the magnitude of the shift in $pK_a$ relative to the normal value of 10.4 for Lys in water, as represented in panel (A).

The p$K_a$ of 19 of the 25 internal Lys residues were depressed relative to the normal p$K_a$ of 10.4 for Lys in water (Table 2 and FIG. 5A). The p$K_a$ values of some internal Lys residues are almost as low as 5; these are among the largest shifts ever reported for Lys p$K_a$ values. The few known p$K_a$ values for naturally occurring internal Lys residues are within the range measured for the internal Lys in SNase (19).

Figure 5B:
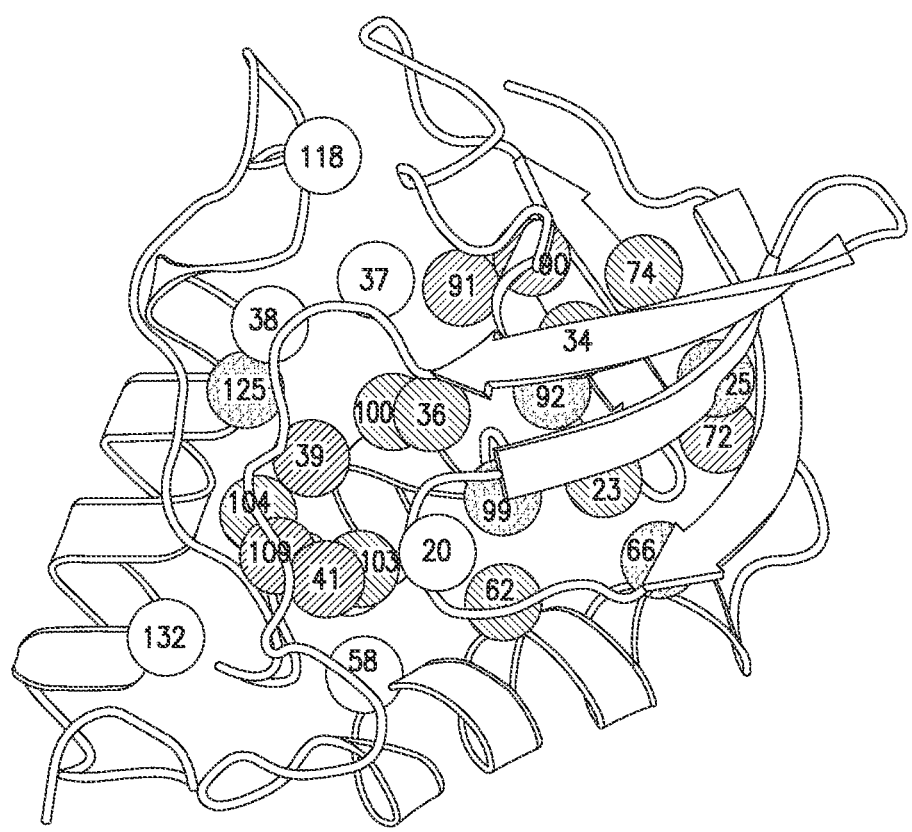

The depression of p$K_a$ values of basic residues implies that the charged form of the ionizable moiety is destabilized relative to the neutral one. This is consistent with the Lys side chains residing in the interior of the protein, in at least a partially dehydrated form, in microenvironments that are less polar and polarizable than water. The buried nature of the side chains has been corroborated by crystal structures of many of the variants. In over 25 structures of variants with either Lys, Glu or Asp at some of the 25 internal positions the ionizable side chains in the neutral state are truly internal; the ionizable moieties are not in contact with bulk water (the coordinates of these structures have been deposited in the Protein Data Bank). With the exception noted ahead, no obvious correlation has been found between the shifts in the p$K_a$ values of the internal Lys residues and their location in the structure of Δ+PHS variant of SNase (FIG. 5B). No structural metric such as solvent accessibility, density of atoms surrounding $C_\alpha$, depth of burial of $C_\alpha$, and number of nearby polar groups, correlated with the magnitude of the shifts in p$K_a$ values.

The p$K_a$ values of six Lys residues (K20, K37, K38, K58, K118 and K132) could not be measured because the $\Delta\Delta G°_{H2O}$ vs. pH data was flat in the range of pH that was sampled. This implies that these six Lys residues titrate with p$K_a \geq 10$. In contrast, only two of the internal Glu residues titrated with normal p$K_a$ values (13). The length of the Lys side chain compared to the shorter Glu side chain would suggest that these Lys residues have normal p$K_a$ values because the Lys side chain can snorkel and placed the ionizable amino group in contact with interfacial or bulk water. This interpretation might not apply to all these case. In one case that was examined in detail, the crystal structure showed that the side chain and the ionizable moiety of Lys-38 are buried and inaccessible to solvent (3, 11). According to molecular dynamics simulations and NMR spectroscopy experiments, the reason that Lys-38 titrates with a normal p$K_a$ despite being buried is that the surrounding region of the protein is locally unstable. In the long-time scale of the equilibrium thermodynamic experiments used to measure p$K_a$ values the protein samples many states and the charged moiety samples bulk water extensively. All the other Lys residues with normal p$K_a$ values are either in loops are at the ends of elements of secondary structure (FIG. 5B), where fraying and other dynamic processes might expose the putatively buried group to water.

Figure 6A:
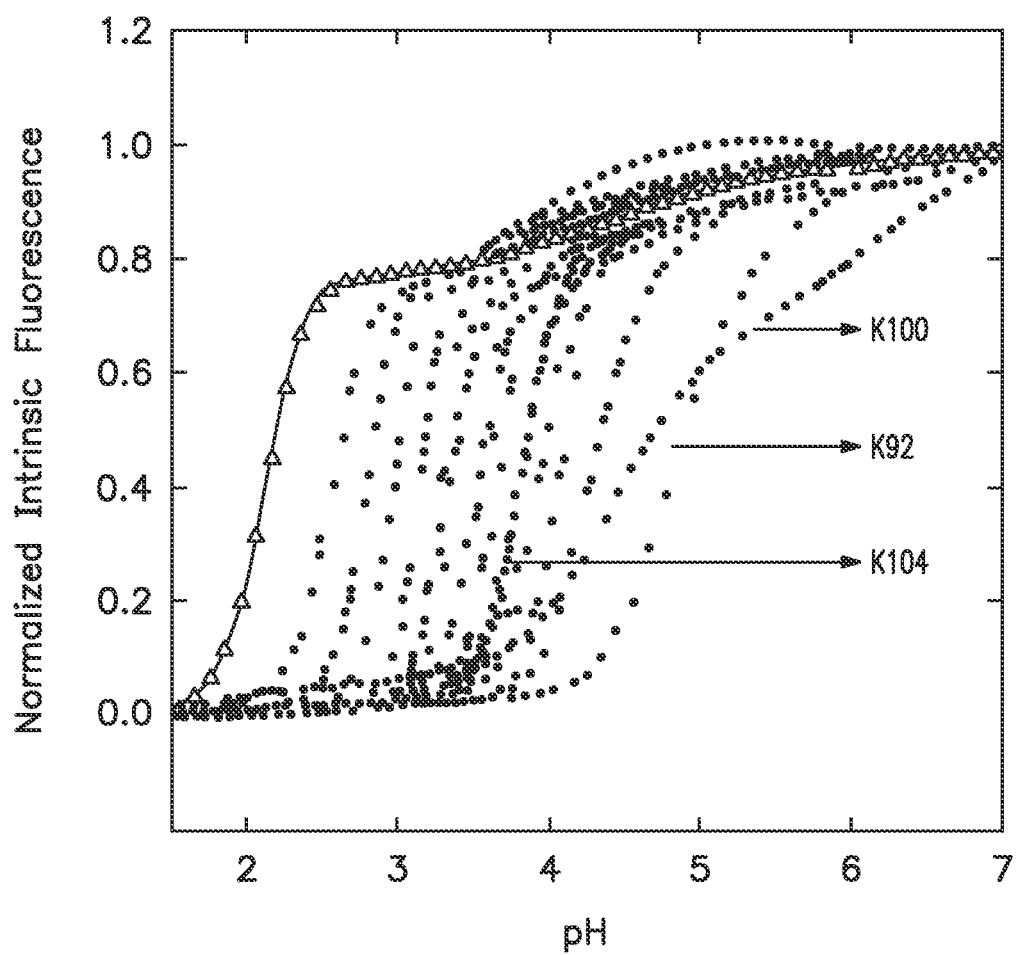
FIG. 6 shows the conformational consequences of ionization of Lys residues at 25 internal positions. (A) pH titrations of $\Delta$+PHS nuclease (▲) and of variants with internal Lys (•) residues monitored by Trp fluorescence, as described previously (REF), Variants that exhibit partial (•) or global (•) unfolding concomitant with ionization of the internal Lys are labelled. (B) pH titrations of $\Delta$+PHS nuclease (▲) and of variants with internal Lys (•) residues monitored by far-UV CD at 222 nm. Variants that exhibit partial (•) or global (•) unfolding concomitant with ionization of the internal Lys are labelled. (C) Location of Lys residues that trigger local (•) or global (•) structural changes upon ionization, mapped on the structure of $\Delta$+PHS (pdb accession code 3bdc (17)).
Figure 6B:
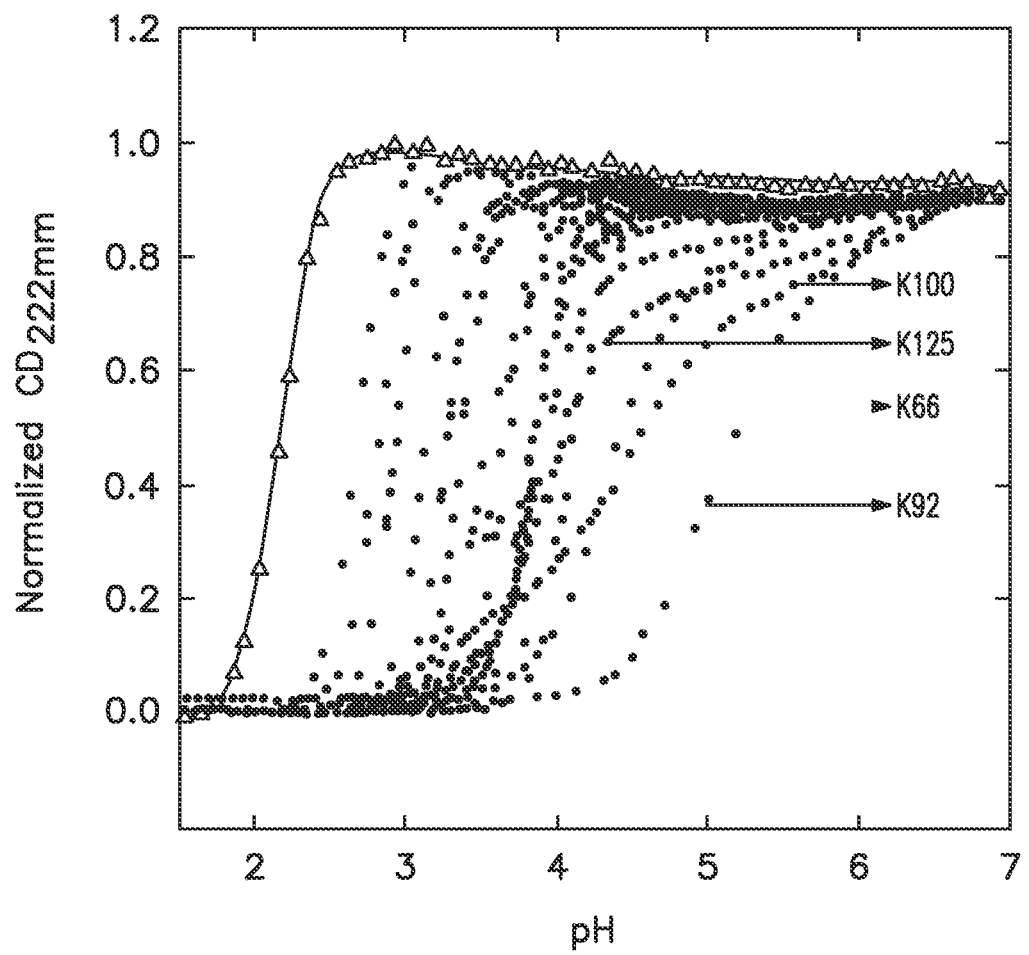

Structural Consequences of Ionization of Internal Lys Residues.

pH titrations monitored by Trp fluorescence (FIG. 6A) and far-UV CD at 222 nm (FIG. 6B) showed that most of the variant proteins with internal Lys residues are fully folded under conditions of pH where the internal Lys are charged. This suggests that the charged moieties are somehow stabilized in their buried microenvironments. Although the observations with these optical methods illustrate well the remarkable resilience of the protein towards the ionization of internal groups, these optical spectroscopy studies do not exclude the possibility that the ionization of internal Lys residues triggers slight structural reorganization that is undetectable with optical methods. NMR spectroscopy is being used in our lab to characterize in detail any conformational reorganization coupled to the ionization of these internal Lys residues.

Lys-92 has the most depressed p$K_a$ (p$K_a$=5.3). The ionization of this Lys residue unfolded the protein—the only case of global unfolding in response to the ionization of any internal Lys. The ionization of Glu-92 had the same effect (13). Position 92 is possibly the most deeply buried location in SNase. The side chains of Lys-92 and Glu-92 are buried in the main hydrophobic core of the protein (10). The highly hydrophobic microenvironments are consistent with the large shifts in the p$K_a$ of Lys-92 and Glu-92. On the other hand, despite being deeply buried, the side chain of Lys-92 can occupy two alternative positions, and the side chain of Glu-92 stabilizes a large number of internal water molecules that hydrated the carboxylic group quite effectively (10, 14-16).

Four variants (V66K, N100K, V104K and L125K) showed changes in optical properties coincident with the ionization of the internal Lys residue. The changes are subtle and in all cases the protein undergoes global acid unfolding at pH values below the p$K_a$ of the internal Lys: therefore, they were interpreted as evidence of local or partial unfolding. These cases are of special interest because they identify situations where the high apparent polarizability clearly reflects a substantial conformational reorganization coupled to the ionization of the internal group. The structural nature of the partial unfolding is not known but it is currently under study with NMR spectroscopy. In the case of residues at position 66, which have been studied previously, the ionization of the internal Lys with a p$K_a$ near 5.7 leads to the loss of approximately one turn of α-helix (4, 20). This has already being confirmed with NMR spectroscopy. These cases where the ionization of an internal group is coupled to sub-global structural reorganization will be particularly useful for calibration of structure-based electrostatics calculations designed to reproduce conformational changes coupled to changes in pH.

The probability of populating intermediates between the fully folded and the fully denatured states increases as the stability of the native state decreases. Therefore, the likelihood that the ionization of an internal Lys triggers conformational reorganization is governed by the stability of the native state near the pH where ionization occurs. The stability of the protein in the range of pH where the Lys residues ionize ($\Delta G°_{H2O}$ in Table 2) is determined by two factors. One is the loss of stability related to the substitution of the internal position with neutral Lys. This is a pH independent term that accounts for all differences in non-covalent interactions of the original side chain and the Lys side chain. The stability of the Lys-substituted proteins at high pH, near the normal $pK_a$ of Lys, provides an estimate of the cost of substituting with neutral Lys (12, 21). The second factor that destabilizes the Lys-containing variants is the shift in $pK_a$ proper. At pH values below the normal $pK_a$ of 10.4 for Lys in water, the stability of a variant with an internal Lys with depressed $pK_a$ decreases by 1.36 kcal/mol (298K) for every unit shift in the $pK_a$ (FIGS. 4A and 4B). The reason that the ionization of only some of the internal Lys residues promotes global or partial unfolding is that the stability of the variants in the range of pH where the internal Lys residues titrated differs from variant to variant (Table 2). The variants where structural reorganization is observed concomitant with ionization of the internal Lys (I92K, V66K, L125K, V104K, and N100K) have stability of 3.8 kcal/mol or less at the pH where the groups titrate. By this criterion, the L25K and V99K variants, and maybe even the F34K variant, should have also exhibit reorganization concomitant with ionization of the internal Lys. NMR spectroscopy may used to try to detect conformational reorganization in these variants.

TABLE 2

Apparent $pK_a$ values of Lys residues at 25 internal positions of SNase

| Position | $^a pK_a$ | $^b \epsilon_{app}$ | $^c \Delta G°_{ion}$: | $^d \Delta G°_{H2O}$ | $^e pH_{mid}$ FL | $^f pH_{mid}$ |
|---|---|---|---|---|---|---|
| I92K | 5.3 | 8 | 6.9 | 0.8 | 4.8 | 5.0 |
| V66K | 5.6 | 9 | 6.5 | 3.2$^s$ | 3.8 | 3.9 |
| L125K | 6.2 | 10 | 5.7 | 3.2 | 3.9 | 3.9 |
| L25K | 6.3 | 10 | 5.6 | 3.4 | 3.8 | 3.8 |
| V99K | 6.5 | 11 | 5.3 | 2.5 | 4.3 | 4.3 |
| F34K | 7.1 | 12 | 4.5 | 4.2 | 3.8 | 3.9 |
| L36K | 7.2 | 12 | 4.4 | 4.7 | 4.1 | 4.1 |
| V23K | 7.3 | 13 | 4.2 | 5.2 | 4.0 | 4.0 |
| V74K | 7.4 | 13 | 4.1 | 4.8 | 3.7 | 37 |
| V104K | 7.7 | 14 | 3.7 | 3.8 | — | 3.9 |
| T62K | 8.1 | 16 | 3.1 | 8.0 | 3.3 | 3.4 |
| L103K | 8.2 | 16 | 3.0 | 6.4 | 3.6 | 3.7 |
| I72K | 8.6 | 19 | 2.4 | 5.6 | 3.4 | 3.4 |
| A90K | 8.6 | 19 | 2.4 | 4.5 | 3.8 | 3.8 |
| N100K | 8.6 | 19 | 2.4 | 1.5 | — | — |
| V39K | 9.0 | 22 | 1.9 | 4.5 | 3.5 | 3.6 |
| Y91K | 9.0 | 22 | 1.9 | 4.9 | 3.6 | 3.5 |
| A109K | 9.2 | 24 | 1.6 | 7.6 | 3.3 | 3.3 |
| T41K | 9.3 | 26 | 1.5 | 9.5 | 3.0 | 2.9 |
| G20K | 10.4 | — | — | 7.5 | 3.2 | 3.1 |
| L37K | 10.4 | — | — | 7.9 | 2.8 | 2.7 |
| L38K | 10.4 | — | — | 7.5 | 2.8 | 2.8 |
| A58K | 10.4 | — | — | 6.6 | 3.3 | 3.3 |
| N118K | 10.4 | — | — | 8.8 | 2.6 | 2.4 |
| A132K | 10.4 | — | — | 4.6 | 3.3 | 3.4 |

$^a$Apparent $pK_a$ values. Estimated experimental error was 0.2.
$^b$Apparent dielectric constant, calculated with equation 3 in Dwyer et al(2) using $\Delta G°_{ion}$ and $r_{ion} = 2$ Å, $r_{prod} = 12$ Å.
$^c$Calculated as $1.36 * (pK_a - pK_{a\,rmod})$, assuming a $pK_{a\,rmod}$ of 10.4. Estimated uncertainty, based on the uncertainty in apparent $pK_a$ is between 0.2 and 0.3 kcal/mol.
$^d$Thermodynamic stability of the protein at the apparent $pK_a$, measured by GdnHCl titration monitored by Trp fluorescence, as described previously (23). Collectively, the experimental error of the reported free energies ranges from 0.1 and 0.4 kcal/mol.
$^e$Midpoint of the major base unfolding transition monitored by Trp fluorescence. In all cases, the experimental uncertainty is 0.1 pH units.
$^f$Midpoint of the major base unfolding transition monitored by CD. In all cases, the experimental uncertainty is 0.1 pH units.
$^s$Data from Fitch et al (5).

Evidence of Coulomb Interactions Between Internal and Surface Ionizable Groups.

Figure 7A:
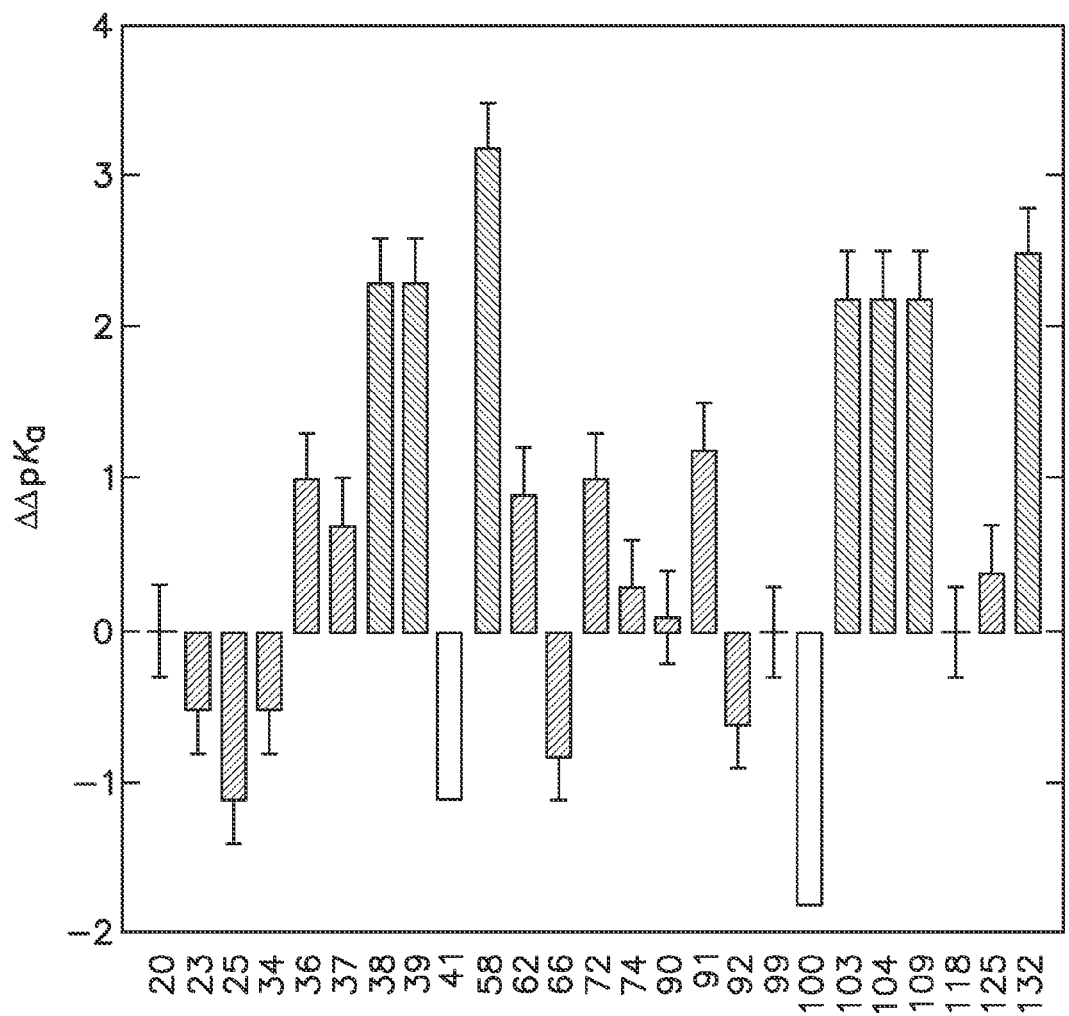
FIG. 7 shows the comparison of $pK_a$ shifts of Glu and Lys at 25 internal positions. (A) Difference in $pK_a$ values of Lys and Glu residues (Glu-Lys) at 25 internal positions in SNase. The color code is meant to distinguish groups with small (green) and large (blue) differences in $pK_a$ values. (B) Distribution of differences in the $pK_a$ values of Lys and Glu residues mapped on the structure of $\Delta$+PHS (pdb accession code 3bdc (17)).
Figure 7B:
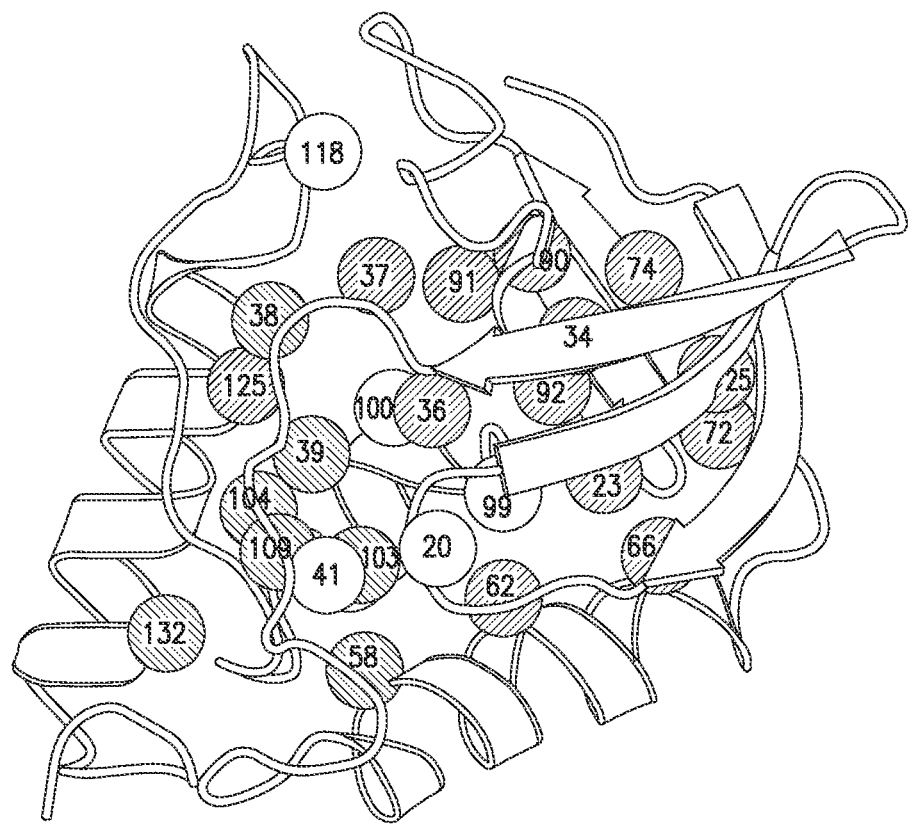

The pH dependence of stability of 9 Lys-containing variants (Lys-34, Lys-36, Lys-23, Lys-104, Lys-62, Lys-103, Lys-90, Lys-109, Lys-41) could not be interpreted in terms of shifts in the $pK_a$ of a single group (e.g. Lys-62 in FIGS. 4C and 4D). The fact that internal Lys in the charged state can affect the $pK_a$ values of surface ionizable residues suggest that internal charges can have substantial Coulomb interactions with surface charges. Further evidence of communication between internal and surface charges came from comparison of $pK_a$ values of Glu and Lys residues at the same internal positions (FIGS. 7A and 7B).

In a few cases the shifts in the $pK_a$ of a Glu or a Lys at the same location are comparable. In many cases the shifts in $pK_a$ values differ by nearly one full $pK_a$ unit. To interpret these differences in detail, in terms of differences in their microenvironments, it will be useful to have crystal structures. This will allow us to evaluate the roles of local polarity and distance to bulk solvent as determinants of $pK_a$ values. There are seven positions (38, 39, 58, 103, 104, 109, 132) where the shifts in the $pK_a$ of Glu residues were much larger than for Lys residues (FIG. 4A). In these positions the internal Lys residues in the charged state are stabilized better than the internal Glu residues in the charged state. These seven positions cluster near the active site of SNase (FIG. 7B). The most salient characteristic of the active site of SNase is a high concentration of acidic residues (Asp-19, Asp-21, Asp-40 and Glu-43, and peripherally Glu-52, Glu-101, Glu-129 and Glu-135). The clear differences in shifts in $pK_a$ values of Glu and Lys at internal positions near the active site suggest that the internal Lys residues in the charged state have favorable Coulomb interactions with the cluster of acidic residues in this region of the protein. This might be a consequence of the greater length of the Lys side chain compared to Glu, which would place them closer to the protein-water interface. On the other hand, the effect could involve a contribution of both attractive interactions of internal Lys with surface Glu or Asp, and repulsive interactions of internal Glu with the surface negative charges.

Enzymes and all proteins involved in H$^+$ transport depend on internal ionizable groups for their function. Although some internal ionizable groups can actually stabilize the folded state even when they are charged (21), in general proteins are destabilized significantly by the presence of ionizable groups in their hydrophobic interior (Table 2). Because the protein interior is not as polar nor as polarizable as water, the neutral form of internal ionizable groups is preferred over the charged form, therefore, internal ionizable groups titrate with unusual $pK_a$ values. Although the molecular determinants of $pK_a$ values of internal ionizable groups are not well understood, it is clear that simply by virtue of being internal, the internal Lys residues in SNase can achieve $pK_a$ values comparable to those of naturally occurring internal Lys involved in H$^+$-activated processes.

The Gibbs free energy required to create positive charge inside SNase varies between 1.5 and 6.9 kcal/mol ($\Delta G°_{ion}$ in Table 2) depending on the location of the internal ionizable group. These energies are comparable to the ones required to create negative charge inside SNase (12). The importance of these free energies is two fold. First, they contribute insight into the remarkable ability of proteins to stabilize charge in their hydrophobic interior. Second, these free energies describe, for the first time, the minimal amount of stability required for proteins to stay at least partially folded when internal ionizable groups become charged as part of then natural cycle of biological function. This has important implications for the evolution of enzymes and other proteins that depend on internal ionizable groups for their biological functions. It also has implications for the engineering of novel active sites in proteins where, in addition to fulfilling the requirements for the desired chemical reaction, the stability of the template protein has to be sufficiently high to tolerate the presence and ionization of the internal residues at the active site.

Although the range of $pK_a$ values and of ionization free energies for Lys and Glu residues are comparable, the large differences in the properties of Lys and Glu residues at any one internal location can be large. This is consistent with the acid/base titrations monitored by Trp fluorescence or far-UV CD, showing that the energetics of ionization are not determined solely by the ability of ionizable groups at any one site to trigger conformational reorganization. Crystal structures of many variant proteins with internal Lys and Glu will be required to assess how differences in the shifts in $pK_a$ values reflect differences in the length of the ionizable side chain or in their hydrogen bonding potential or derealization of charge in the ionizable moieties. Surprisingly, despite their inherently different physical properties, the ionizable side chains of Lys and Glu were equally well tolerated in both the neutral and the ionized states.

The $pK_a$ values of internal ionizable groups will impact on structure-based calculations of $pK_a$ values and electrostatic energies. When the shifts in $pK_a$ values in Table 1 were analyzed with a simple electrostatics continuum formalism that assumed that the dehydration experienced in the buried was solely responsible for the shifts in $pK_a$, the analysis suggested that the protein behaved as a material with a relatively high dielectric constant ranging from 8 to 26 (Table 2). The apparent dielectric constants obtained by more sophisticated analysis of some of these variants of SNase with state-of-the-art continuum electrostatics methods were equally high (4, 5). It will be difficult to reproduce this high apparent polarizability computationally. The $pK_a$ values of internal ionizable groups reflect the balance between opposing influences. On the one hand there is the total or partial dehydration of the internal ionizable groups in their buried locations, which is destabilizing. This can be compensated to varying degrees by stabilization of the charged state by electronic polarization of the surrounding atoms, interactions with protein polar groups, with internal water molecules, with surface charges and even with the reaction field in bulk water. Local or subglobal structural reorganization to maximize favorable interactions between the internal charge and the protein, or more likely, to maximize hydration of the charge, can also be reflected in these $pK_a$ values. The accurate calculation of $pK_a$ values of internal ionizable groups would require accurate estimation of all of these different factors, which is still a tall order. With the data in hand to allow critical assessment but also to guide improvements to the methods, it should be possible to improve our ability to interpret electrostatic effects in the protein interior. This will improve our ability to interpret the structural and physical basis of fundamental biochemical processes such as catalysis and $H^+$ transport.

Protein Engineering.

The Lys-containing variants of the Δ+PHS variant of SNase were prepared with QuikChange site-directed mutagenesis on a pET24A+ vector as described previously (4, 12). Purification was performed as described previously (22):

Stability Measurements.

Stability measurements were performed with guanidinium chloride titrations using an Aviv Automated Titration Fluorimeter 105 as described previously (23). Linkage analysis of pH dependence of stability to obtain $pK_a$ values was performed as described previously (2, 4, 7).

Optical Spectroscopy.

pH titrations monitored with CD at 222 nm or with Trp fluorescence were performed with an Aviv Automated Titration Fluorimeter model 105 and with an Aviv circular dichroism spectrometer model 215, respectively. The experiments were performed with previously published protocols (23).

REFERENCES

Each of the following publications is incorporated herein by reference.
1. Schutz C N & Warshel A (2001) Proteins. Structure, Function, and Genetics 44, 400-417.
2. Dwyer J, Gittis A, Karp D, Lattman E, Spencer D, Stites W, & Garcia-Moreno E. B (2000) Biophysica Journal 79, 1610-1620.
3. Harms M J, Castaneda C A, Schlessman J L, Sue G R, Isom D G, Cannon B R, & Garcia-Moreno E. B (2009) J. Mol. Biol. 389, 34-47.
4. Karp D A, Gittis A G, Stanley M R, Fitch C A, Stites W E, & Garcia-Moreno E. B (2007) Biophysica Journal 92, 2041-2053.
5. Fitch C A, Karp D A, Lee K K, Stites W E, Lattman E E, & Garcia-Moreno E. B (2002) Biophysica Journal 82, 3289-3304.
6. Garcia-Moreno E. B, Dwyer J, Gittis A, Lattman E, Spencer D, & Stites W (1997) Biophysical Chemistry 64, 211-224.
7. Stites W E, Gittis A G, Lattman E E, & Shortle D (1991) Journal of Molecular Biology 221, 7-14.
8. Ghosh N & Cui Q (2008) J. Phys. Chem. B. 112, 8387-8397.
9. Zheng L, Mengen C, & Yang W (2008) Proc Natl. Acad. Sci. USA 105, 20227-20232.
10. Nguyen D M, Reynald R L, Gittis A G, & Lattman E E (2004) J. Mol. Biol., 565-574.
11. Harms M J, Schlessman J L, Chimenti M S, Sue G R, Damjanovic A, & Garcia-Moreno E. B (2008) Protein Science 17, 833-845.
12. Isom D G, Cannon B R, Castaneda C A, Robinson A, & Garcia-Moreno E. B (2008) Proc Natl. Acad. Sci. USA 105, 17784-17788.
13. Isom D G, Castaneda C A, Cannon B R, Vclu P D, & Garcia-Moreno B (2009) Nature.
14. Damjanovic A, Garcia-Mcrenc E. B, Lattman E E, & Garcia A E (2005) Proteins: Structure Function and Bioinformatics 60, 433-449.
15. Damjanovic A, Schlessman J L, Fitch C A, Garcia A E, & Garcia-Moreno E. B (2007) Biophysical Journal (in press).
16. Schlessman J L, Abe C, Gittis A G, Karp D A, Dolan M A, & Garcia-Moreno E. B (2008) Biophys. J. 94, 3208-3216.
17. Castaneda C A, Fitch C A, Majumdar A, Khangulov V, Schlessman J L, & Garcia-Moreno E. B (2009) Proteins. Struct. Fund. Bioinfll, 570-588.
18. Lee K K, Fitch C A, Lecomte J T J, & Garcia-Moreno E. B (2002) Biochemistry 41, 5656-5667.
19. Ho M, Mcnctrct J, Tsuruta H, & Allen K N (2009) Nature 459, 393-399.
20. Karp D A, Stahley M R, & Garcia-Moreno E. B (2009) Biochemistry.
21. Thurlkill R L, Grimsley G R, Scholtz J M, & Pace C N (2006) Journal of Molecular Biology 362, 594-604.
22. Shortle D & Meeker A (1986) Proteins: Structure, Function, and Genetics 1, 81-89.

23. Whitten S T & Garcia-Moreno E. B (2000) Biochemistry 39, 14292-14304.

Conformational Consequences of Ionization of Buried Lys, Glu and Asp at Position 66 in Staphylococcal Nuclease (SNase)

The $pK_a$ values measured previously for the internal Lys-66, Asp-66 and Glu-66 in variants of a highly stable form of staphylococcal nuclease are shifted by as many as 5 $pK_a$ units relative to normal $pK_a$ values in water. These shifts cannot be reproduced with continuum electrostatics calculations with static structures unless the protein is treated with high dielectric constants near 10. These high apparent dielectric constants are inconsistent with the highly hydrophobic microenvironments of the ionizable moieties in crystal structures. To examine the origins of these high apparent dielectric constants we showed that the $pK_a$ values of these internal residues are sensitive to the global stability of the protein: the shifts are smaller in less stable forms of nuclease. This implies that the high apparent dielectric constants reflect conformational reorganization coupled to the ionization of the internal groups. To detect this directly, acid/base titrations monitored with Trp fluorescence, near-UV and far-UV CD (circular dichroism) spectroscopy were performed on variants with Lys-66, Glu-66 or Asp-66 in background proteins with different stability. Conformational reorganization coupled to the ionization of the internal groups was spectroscopically detectable, especially in the less stable background proteins. The data shows that to improve the accuracy of structure-based $pK_a$ calculations of internal groups the calculations will have to treat explicitly all structural reorganization coupled to ionization. The data also suggests a novel approach to mapping the folding free energy landscape of proteins by using internal ionizable groups to stabilize partially unfolded states.

Internal ionizable groups in proteins are central to key biochemical processes such as catalysis (1, 2), proton ($H^+$) transport (3), electron (e) transfer (4), and ion (5) and water homeostasis (6). To describe the structural basis of biological energy transduction it is necessary to understand the molecular determinants of $pK_a$ values of internal ionizable groups, and to quantify the effects of internal charges on protein stability and conformation. Here we examine these issues in staphylococcal nuclease (SNase), a small enzyme that is uniquely well suited for this purpose.

Val-66, one of the residues that constitute the main hydrophobic core of SNase, has been replaced with Lys (7-9), Asp (10), and Glu (11). The internal Lys-66, Asp-66 and Glu-66 titrate with highly perturbed $pK_a$ values shifted by as many as 5 $pK_a$ units in the direction that favors the neutral state (i.e. elevated for Asp and Glu, depressed for Lys). The direction of the shifts in $pK_a$ suggests that the interior of SNase is neither as polar nor as polarizable as water. This is consistent with the crystal structures of the variants with V66K, V66D and V66E, where the ionizable groups of Lys-66, Asp-66 or Glu-66 are internal, buried approximately 10 A from bulk solvent in a hydrophobic pocket, far from other charges or polar atoms of the protein (7-11).

Structure-based calculations with continuum electrostatics methods suggest that the $pK_a$ values of these internal groups are perturbed because the dehydration experienced by the ionizable groups in their deeply buried positions is not compensated by interactions with polar groups, surface charges, or by the buried water molecules observed in some crystal structures (10-12). To reproduce the experimental $pK_a$ values in these calculations the protein has to be treated with a dielectric constant of approximately 10. These apparent dielectric constants are not real dielectric constants. They are model dependent quantities without precise structural or physical meaning, intended to capture implicitly all factors that are not dealt with explicitly or correctly in the calculations (13). Despite their imprecise physical meaning, they are useful to gauge the magnitude of the net polarizability experienced by an internal ionizable group. The high values of the apparent dielectric constant reported by Lys-66, Asp-66 and Glu-66 suggest that the interior of SNase is highly polar or polarizable, but this is not consistent with the nonpolar microenvironments in which these ionizable moieties are found in the crystal structures. The structural origins of the high apparent dielectric constant reported by these ionizable groups are not known.

The dielectric properties of a material are determined by polarization and relaxation processes. For water at 298 K, electronic polarization is responsible for the high-frequency dielectric constant of 3 (14), whereas its overall dielectric constant of 78.5 is governed by the relaxation of water molecules in the electrostatic field. The interior of proteins is usually neither as polar nor as polarizable as water: therefore, the magnitude of the dielectric effect inside a protein is expected to be lower than that of water. The low dielectric constants of 2 to 4 measured experimentally with dry protein powders are determined primarily by electronic polarization (15-17). Contributions from dipolar relaxation processes cannot be measured experimentally with dry protein powders because water is required to activate dynamic processes, and in its presence, the dielectric properties measured are those of water, not of protein.

All the factors that affect the $pK_a$ of an internal group can, in principle, contribute towards the apparent dielectric constant reported by these groups. Chief among these factors are interactions with surface charges and with fixed permanent dipoles (18), dipole relaxation (19), the reaction field from polarization of bulk water, and water penetration (12). However, when the ionization of an internal group triggers structural reorganization, all these factors are less relevant: structural reorganization becomes the dominant contribution to the apparent dielectric effect and to the $pK_a$. For this reason, it is of interest to examine the extent to which the high apparent dielectric constant reported by Lys-66, Asp-66 and Glu-66 in SNase reflects conformational reorganization coupled to the ionization of these internal groups.

Initial evidence that the ionization of these internal groups triggers subtle structural reorganization came from the recent demonstration that the ionization of Asp-66 in a highly stable form of SNase induces a small loss of intensity in the far-UV CD signal, consistent with the loss of α-helical content (10). It was speculated that the ionization of Asp-66 triggers the unwinding of one turn of α-helix. This would be sufficient to expose the previously buried carboxylic group of Asp-66 to bulk water and to normalize its $pK_a$. This was not observed clearly with Glu-66 (11) and Lys-66 (7) in highly stable forms of SNase. Here we show that the $pK_a$ values of the ionizable groups at position 66 in SNase are affected by the global stability of the protein and that the ionization of the internal groups triggers conformational reorganization detectable with Trp fluorescence and CD spectroscopy. The approach involved comparison of the consequences of ionization of Lys-66. Asp-66 and Glu-66 in two different forms of SNase with stabilities different by 4 kcal/mol. The data demonstrate that the high apparent dielectric constants reported by Lys-66, Asp-66 and Glu-66 reflect a conformational transition coupled to the ionization of the internal groups. Besides clarifying the structural meaning of the high apparent dielectric constant reported by these internal groups, these experiments also draw attention to the limitations inherent to $pK_a$ calculations with continuum methods that use a single, static structure. Computational methods that do not treat explicitly the coupling between the ionization of internal groups and conformational reorganization are likely to yield inaccurate estimates of $pK_a$ values.

Staphylococcal Nuclease.

The Quickchange kit from Stratagene (La Jolla, Calif.) was used to make the substitutions V66K, V66D or V66E in two stable forms of staphylococcal nuclease (SNase) known as PHS after the three substitutions used to engineer it (variant of SNase with P117G, H124L, and S128A), and Δ+PHS (PHS with additional G50F and V51N substitutions and a 44-49 deletion). All mutagenesis was performed with the K pL9 plasmid. Proteins were expressed and purified by the method of Shortle and Meeker (20) as modified by Byrne et al (21). Protein concentration was determined using an extinction coefficient of $1.46 \times 10^4$ $M^{-1}$ $cm^{-1}$, determined using the method of Gill and von Hippel (22). Background and variant proteins were treated with the same extinction coefficient.

pH Titrations Monitored by Fluorescence and CD.

The acid/base titrations monitored by changes in intrinsic fluorescence were performed with an AVIV ATF-105 automated titration fluorometer (Aviv Inc, Lakeland, N.J.). The titrations that monitored changes in CD were performed with an AVIV 215 CD spectrometer (Aviv Inc, Lakeland, N.J.). All data were collected at 25° C. in 100 mM KCl following protocols that have been described previously (25). The only difference between the protocols used with wild type SNase and with the variants with internal ionizable groups is that the delay times between the delivery of consecutive doses of titrant in the automated acid/base unfolding experiments were longer for variants in both Δ+PHS and PHS backgrounds. Delay times of 2 minutes for PHS and its variants, and 5 minutes for Δ+PHS and its variants, were used to allow the system to reach equilibrium. This delay corresponds to 7 lifetimes in the decay of the fluorescence signal following a pH jump from pH 7 to the pH at the midpoint of the unfolding transitions. The experiments monitoring intrinsic fluorescence and CD at 222 nm were performed with a protein concentration of approximately 50 Experiments that monitored CD at 275 nm were performed with approximately 500 μg/mL. The buffers used in acid titrations monitored by fluorescence consisted of 5 mM MES, 5 mM HEPES and 100 mM KCl. In the base titrations the buffer was 5 mM HEPES with 100 mM KCl. The titrations monitored by CD were performed with a buffer consisting of 100 mM KCl and 5 mM each of MES, HEPES, TAPS, CHES and CAPS. Samples were titrated with 0.3 N HCl or KOH. All buffers and titrants were from Sigma (St. Louis, Mo.). The analysis of acid/base titrations to obtain the midpoints of the unfolding transitions ($pH_{mid}$) or to describe the steepness of the transition ($\Delta v_H^+$) was performed by nonlinear least squares fit of two- or three-state models of the unfolding process to the data, using the equations described previously (10).

Stability Measurements by Chemical Denaturation.

The Gibbs free energy of unfolding ($\Delta G°_{H2O}$) was measured using the intrinsic fluorescence of Trp-140 to monitor unfolding as described previously (23). GdmCl (guanidinium chloride) (UltraPure grade Invitrogen Life Technologies, CA) was used as a denaturant. All measurements were performed with ATF-105 automated fluorometer (Aviv Inc, Lakeland, N.J.). In the PHS background, in the transition region, five minutes were allowed for equilibration following the addition of titrant. In the Δ+PHS background the delay time was between forty to eight minutes. Protein concentration in these experiments was 50 μg/ml. The buffers varied according to the pH of the experiment. They consisted of 100 mM NaCl with 25 mM each of sodium acetate for pH 4 to 5.5, MES for pH 5.5 to 6.5, HEPES for pH 7 to 8, TAPS for pH 8 to 9, CHES for pH 9 to 10, and CAPS for pH 10 to 11. At the higher pH values, it is difficult to regulate the pH during the titration because GdmCl shifts the $pK_a$ of the buffer. The pH of the solutions at high pH drifted by as much as 0.1 pH units over the course of a titration. At the pH values where the GdmCl titration curve did not reach a native state baseline, the fluorescence value obtained for the native state at other pH values was used to analyze the data to obtain the thermodynamic parameters. The pH of the samples was always checked at the end of each experiment. The final concentration of GdmCl was also measured at the end of each experiment by refractometry. All data were collected at 25° C.

Potentiometric $H^+$ Titrations.

The procedure for the measurement of $H^+$ titration curves of SNase with direct potentiometric methods has been presented elsewhere (7, 11, 23). The data were obtained with protein concentrations of 3 to 4 mg/ml. The protein and water samples were titrated with HCl or KOH of approximately 0.15 N. Reversibility of the titration curves was tested routinely. All titration curves were measured in triplicate. All data were collected at 25° C. in 100 mM KCl. The data were treated by linear interpolation.

X-Ray Crystallography.

The V66K variant of PHS nuclease was crystallized by the hanging drop vapor diffusion method at 4° C. The reservoir solution consisted of 36.5-39% (vol/vol) 2-methyl-2,4-pentanediol and 15% glycerol in 25 mM potassium phosphate buffer, pH 7.0. Two milliequivalents of the inhibitor pdTp and 3 milliequivalents of $CaCl_2$ were added to 9.6 mg/ml protein solution before mixing with an equal volume of reservoir solution. pdTp was synthesized in our laboratory (10). Crystals of PHS/V66K appeared in 1-2 weeks at 4° C.

Diffraction data were collected at three conditions. Two data sets were collected at 100 K, at pH 7 and 4.7, and the third was collected at 298 K at pH 5. Data were collected from a single crystal at each condition using an R-AXIS IV image plate detector (MSC, The Woodlands, Tex.). To obtain data at pH 4.7, crystals grown at pH 7 were transferred into drops of synthetic mother liquor with successively lower pH values. Three transfers were performed to achieve a pH of 4.7. For the structure obtained at pH 5, the crystal was transferred only twice. This procedure minimized the cracking of crystals. For the low temperature structure, the crystal was mounted in a thin loop, with the crystallization buffer as cryosolvent, and flash frozen under a stream of nitrogen at 100 K. For the room temperature structure the crystal was mounted in a thin-walled glass capillary in equilibrium with the well solution. Crystals for all three data sets were found to be isomorphous to those of PHS/V66E (11) and this structure was used as an initial phasing model. Refinement for each structure was carried out using the programs CNS and 0(24, 25). For the crystal at pH 7, data were collected in the resolution range 29.0-1.95 Å. For the crystal at pH 4.7, data were collected in the resolution range 24.0-2.0 Å and the structure was refined to a final R value of 19.9% and an $R_{free}$ of 23.57%. For the structure at pH 5 data were collected in the resolution range 27.0-2.2 Å and the structure was refined to a final R value of 18.76% and a final $R_{free}$ of 23.06%. The electron density for the side chain of Lys-66 was fully visible in the electron density maps at pH 7, mostly visible at pH 5, and totally unresolvable from CP to the amino moiety at pH 4.7.

The goal of this study was to examine structural consequences of the ionization of the internal Lys-66. Asp-66 and Glu-66 in SNase, with the intent of determining if conformational reorganization coupled to their ionization was responsible for the high apparent dielectric constants necessary to reproduce the $pK_a$ of these groups with continuum electrostatics calculations. To this end, we compared the energetics of ionization of Lys-66, Asp-66 and Glu-66 in two different forms of SNase engineered to be more stable than the wild type protein. One of these proteins, referred to as Δ+PHS SNase. has a deletion from 44 to 49 and five substitutions (PI 17G, H124A, S128L, G50F, V51N) relative to the wild type protein. The stability ($\Delta G°_{H2O}$) of Δ+PHS SNase at pH 7 and 100 mM ionic strength is 11.8 kcal/mol (10). The other form of SNase used in this study is known as PHS SNase after the three substitutions (P117G, H124A, S128L) used to engineer it. PHS has a stability of 8 kcal/mol at pH 7, 298 K, 100 mM ionic strength. The $pK_a$ of Lys-66, Asp-66 and Glu-66 were reported previously (7, 8, 10, 11), but the data obtained previously did not allow comparison of the properties of the different internal ionizable groups in background proteins with different stability.

The Δ+PHS protein is being used in studies of internal ionizable residues precisely because of its high stability, to counterbalance the destabilization of the protein when core hydrophobic positions are substituted with ionizable ones, and to maximize the range of pH over which the proteins are stable (26). By using the less stable PHS background protein we hoped to unmask conformational transitions coupled to the ionization of the internal groups.

Stability Measured by Chemical Denaturation.

Figure 8A:
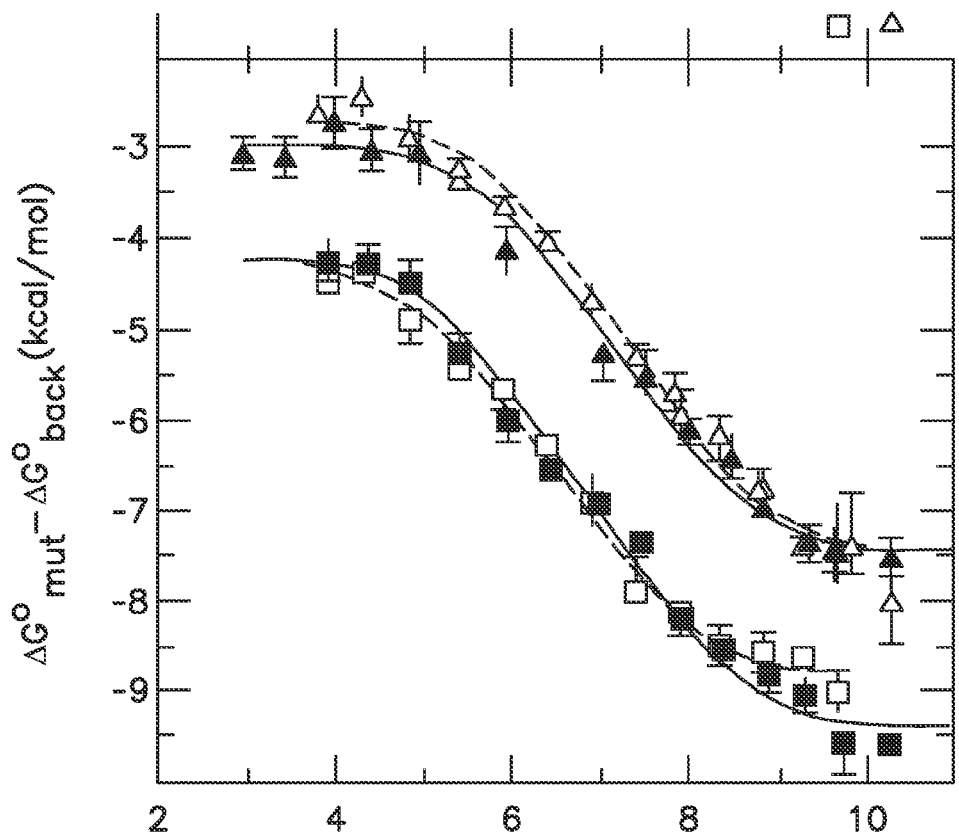
FIG. 8 shows: (A) pH dependence of thermodynamic stability ($\alpha G°_{H2O}$) measured by GdmCl denaturation monitored by changes in Trp fluorescence for PHS nuclease (○) and $\Delta$+PHS nuclease (●), and for V66D (□,■) and V66E ($\Delta$, ▲) variants of these proteins (open symbols for PHS, closed symbols for $\Delta$+PHS). All data at 298 K in 100 mM KCl. The error bars represent errors of the fit of individual denaturation experiments. The lines are meant only to guide the eye. (B) Difference in stability ($\Delta G°_{mut}-\Delta G°_{back}$) between PHS and its V66D (□) and V66E (Δ) variants, and between Δ+PHS and its V66D (■) and V66E (▲) variants. The dashed curves through the data represent fits of Equation 3 in Karp et al (10) for the PHS (- - -) and Δ+PHS (-) proteins.

The thermodynamic stabilities ($\Delta G°_{H2O}$) of PHS and Δ+PHS nuclease and of their V66D and V66E variants, measured over a range of pH values, are shown in FIG. 8A. The shape of the pH dependence of stability of the variants with Asp-66 and Glu-66 is characteristic of proteins with carboxylic groups with $pK_a$ value shifted towards values higher than the normal $pK_a$ of 4.0 and 4.5 for Asp and Glu in bulk water, respectively. The direction of the shifts in $pK_a$ is consistent with the neutral state being preferred when the groups are buried in the hydrophobic interior of the folded protein.

Figure 8B:
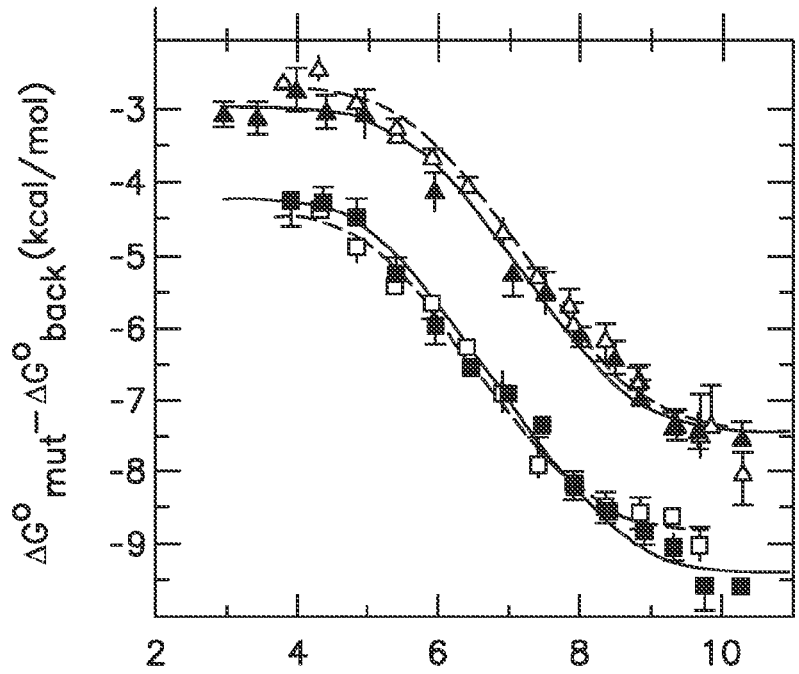

The stabilities of the PHS and Δ+PHS proteins are roughly parallel over a wide range of pH, as are the two curves for the corresponding variants with Asp-66 or Glu-66. For example, at pH 7 the difference in $\Delta G°_{H2O}$ for the V66E variant in PHS and in Δ+PHS is almost 4 kcal/mol, comparable to the difference between the PHS and Δ+PHS background proteins at this pH. The difference ($\Delta\Delta G°_{H2O}$) in $\Delta G°_{H2O}$ for variants with either V66D or V66E substitutions in the PHS and in the Δ+PHS background (i.e. ($\Delta G°_{H2O}$ of the variant minus $\Delta G°_{H2O}$ for the background) also superimpose very well (FIG. 8B). This implies that the substitutions at Val-66 have comparable impact on $\Delta G°_{H2O}$ in the two different background proteins.

$pK_a$ of Lys-66, Glu-66, and Asp-66.

Figure 9:
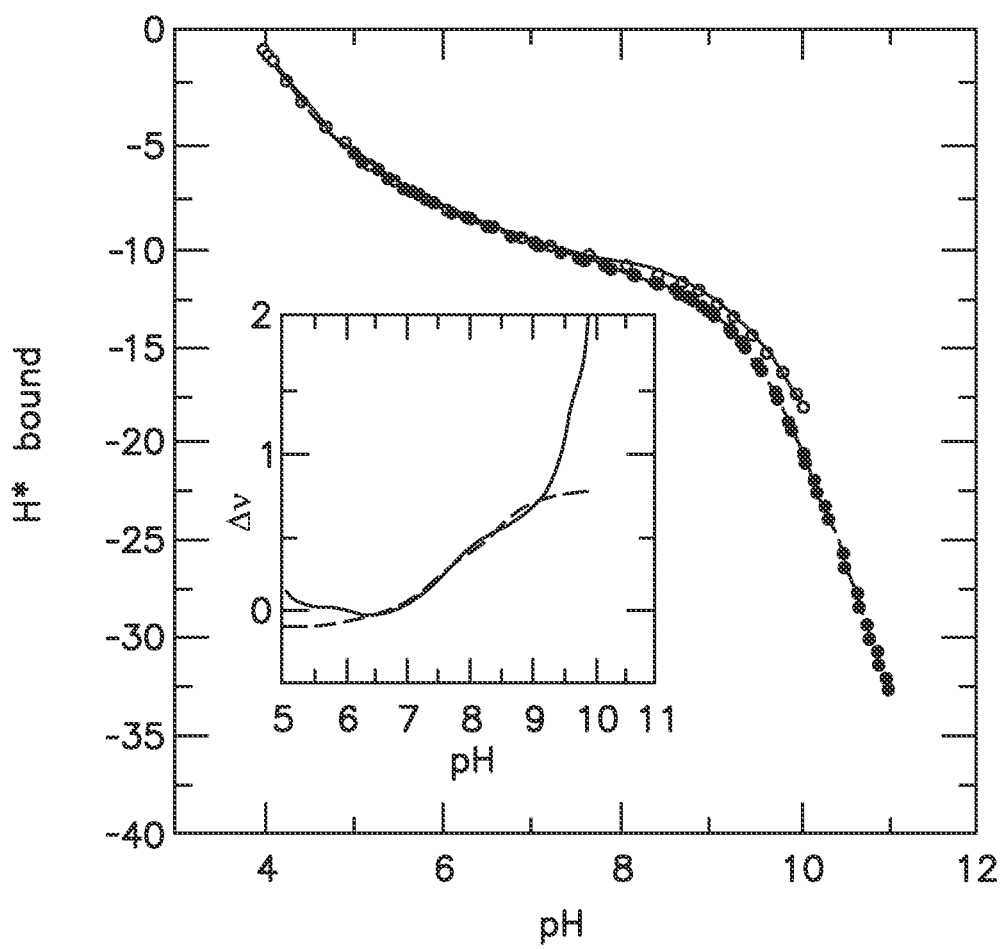
FIG. 9 shows the potentiometric H+ binding measured with PHS (○) and the PHS/V66D variant (●) at 298 K in 100 mM KCl. The solid lines represent cubic linear interpolation. The solid line in the insert shows the difference between the interpolated curves for these two proteins, and the dotted line represents the fit of Equation 4 from Karp et al. (10), with the amplitude of the titration fixed as 1.

The shape of the $\Delta\Delta G°_{H2O}$ vs. pH curves in FIG. 8B reflects differences in the $pK_a$ values of Asp-66 and Glu-66 in the native and in the denatured states. The two regions where these curves exhibit a change in curvature have information about the $pK_a$ values. The use of linkage thermodynamic relationships to obtain $pK_a$ values for the internal ionizable groups by analysis of these curves was described previously (9, 10). $pK_a$ values were also measured with direct potentiometric methods, as described previously (8). These experiments involve measurement of $H^+$ binding/release of the background protein and of the variant with the internal ionizable group, as illustrated for the PHS/V66D variant in FIG. 9. This approach works only if the shift in the $pK_a$ of the internal group is significant, and if the substitution does not affect the $pK_a$ values of other groups, as is the case with the variants of interest to this study. The $H^+$ titration curves of PHS and of its V66D variant (insert, FIG. 9) show that at high pH values more $H^+$ are released by the PHS protein than by the PHS/V66D variant, consistent with the ionization of Asp-66 with an apparent $pK_a$ value near 8.

The $pK_a$ values measured with the two different equilibrium thermodynamic methods (linkage of $\Delta\Delta G°_{H2O}$ vs. pH or potentiometric measurements) are comparable (Table I). The differences between the $pK_a$ of Asp-66 and Lys-66 in the different background proteins are noteworthy. The shift in the $pK_a$ of Asp-66 and Lys-66 is smaller by almost a full $pK_a$ unit in the less stable PHS form of SNase than in the Δ+PHS background. This dependence of the $pK_a$ values on the stability of the background protein is consistent with the ionization of these groups being coupled to local or global unfolding. In the case of Glu-66 the $pK_a$ values measured in the two different background proteins were comparable (Table 3).

TABLE 3

Summary of $pK_a$ values of Asp-66, Glu-66, and Lys-66 in SNase

| Residue | Background protein | $pK_a$ by potentiometry | $pK_a$ from chemical denaturation chemical denaturation |
|---|---|---|---|
| Asp-66 | [1]PHS | 7.97 (7.85, 8.07) | 8.05 (7.86, 8.25) |
| Asp-66 | [2]Δ + PHS | [5]8.95 (8.92, 8.99) | [5]8.73 (8.45, 9.03) |
| Glu-66 | PHS | [6]8.80 (8.70, 8.90) | 8.99 (8.73, 9.28) |
| Glu-66 | Δ + PHS | 9.07 (9.00, 9.10) | 8.80 (8.48, 9.14) |
| Lys-66 | PHS | [7]6.35 (6.25, 6.45) | — |
| Lys-66 | Δ + PHS | [8]5.63 (5.60, 5.64) | [8]5.83 (5.61, 6.05) |
| Lys-66 | [3]wild type | — | [9]6.38 (6.01, 6.75) |

[1]Stable form of nuclease engineered with three substitutions: PI 17G, H124A, and S128L
[2]Stable form of nuclease engineered from PHS with G50F, V51N and a 44-49 deletion,
[3]Measured with the V66K variant of the wild type protein,
[4]In the fits the amplitude of the difference $H^+$ binding curves (insert FIG. 9) was fixed at 1.0.
[5]From Karpetal (V0).
[6]From Dwyeretal (77).
[7]From Garcia-Moreno et al (8).
[8]From Fitch et al (7).
[9]From Stites et al (9).

This does not necessarily exclude coupling between the ionization of Glu-66 and structural reorganization, but it does imply that the magnitude of the shift in the $pK_a$ of this group was not limited by the local or global stability of the protein.

Detection of Conformational Changes With Trp Fluorescence and CD Spectroscopy-Acid/base Titrations Monitored With Fluorescence and CD Spectroscopy. Three different types of spectroscopic signals were used to attempt to detect conformational reorganization coupled to the ionization of internal groups. Acid-base titrations were monitored by: (1) intrinsic fluorescence of Trp-140, which is known to be an excellent reporter of global unfolding of SNase (20, 27, 28); (2) far-UV CD at 222 nm, which reports primarily on the α-helical contents of the protein, with some contribution from β-sheets; and (3) near-UV CD at 275 nm, which reports primarily on the microenvironments of the aromatic residues, which are abundant in SNase.

Figure 10A:
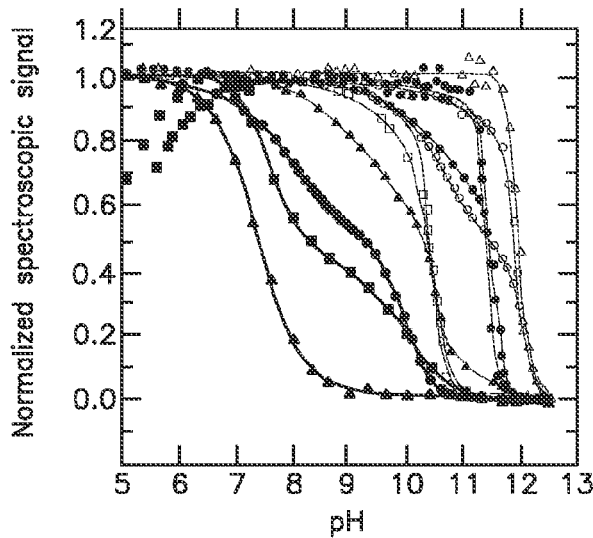
FIG. 10 shows the acid/base titrations monitored by intrinsic fluorescence (0, ●), far UV-CD at 222 nm (Δ, ▲), and near UV-CD at 275 nm (□,■) for variants of PHS of Δ+PHS nuclease. The line represents nonlinear square fits of two state (Eq. 1 from Karp et al (10)) or three state (Eq. 2 from Karp et al (10)) models to the data. (A) Base titration of Δ+PHS nuclease (black), PHS nuclease (red), Δ+PHS/V66D (green) and PHS/V66D (blue). (B) Base titration of Δ+PHSnuclease (black), PHS nuclease (red), Δ+PHS/V66E (green) and PHS/V66E (blue). (C) Acid titration of Δ+PHS nuclease (black), PHS nuclease (red), Δ+PHS/V66K (green) and PHS/V66K (blue).
Figure 10B:
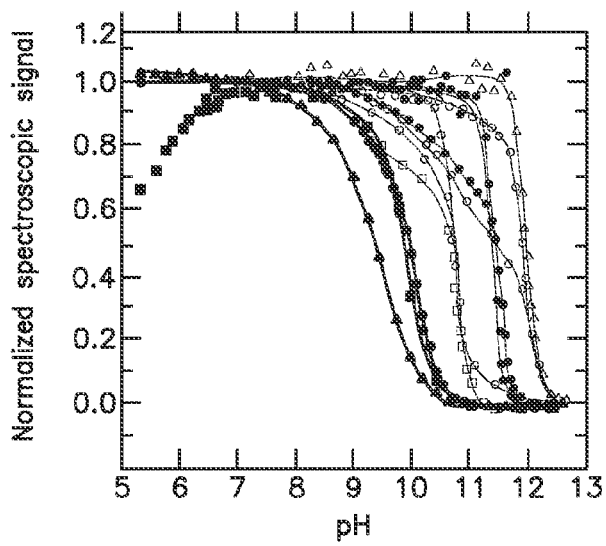

Large differences were observed in the pH titrations of the PHS and Δ+PHS background proteins monitored with the different spectroscopic probes (FIG. 10). A broad predenaturational transition was observed for the two proteins at pH values above 9 by both fluorescence and near-UV CD (FIGS. 10A and 10B). In the titrations monitored by Trp fluorescence (black open circles) this likely reflects contributions from tyrosinate, which begins to be formed in this pH range and which is fluorescent (7). In the near-UV CD this predenaturational transition at high pH might also be related to changes in the conformational state of tyrosine residues. The steep cooperative transition reported for both proteins by all three probes at high pH corresponds to the base-unfolding transition; the midpoint of this transition reported by the different probes is the same (Table 4).

Figure 10C:
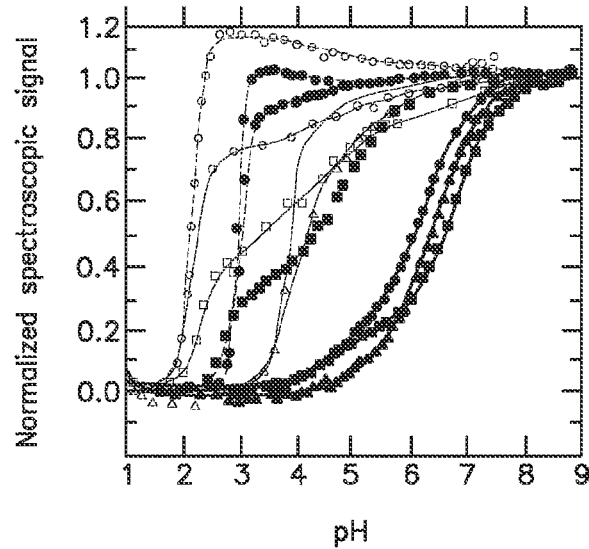

The conformational changes coupled to the ionization of the internal ionizable groups were amplified and more obvious when the titrations were monitored in the variants engineered using the less stable PHS background protein (FIG. 10A-C, blue curves). This was particularly clear in the pH titrations of the PHS/V66K and PHS/V66D proteins. In the case of PHS/V66K (FIG. 10C, blue curves), the three spectroscopic signals report a somewhat biphasic, non-cooperative unfolding, with one transition centered near the $pK_a$ values of 6.4 measured for Lys-66 in PHS nuclease, and a second acid unfolding transition at lower pH that reports on acid unfolding (Table 2). The intensity of the three spectroscopic signals decreased significantly with decreasing pH, suggesting that the ionization of Lys-66 in the PHS background disrupts the native state. The case for a conformational transition coupled to the ionization of Asp-66 in PHS/V66D (FIG. 10A, blue curves) is equally clear. The

TABLE 4

Equilibrium thermodynamic parameters for acid/base unfolding.

| Variant | Background | Signal | $pH_{mid}^1$ | $pH_{mid}^2$ |
|---|---|---|---|---|
| V66K | Δ + PHS | CD (λ = 111 nm) | [5]4.8 (4.2, 5.6) | [5]3.86 (3.83, 3.88) |
| | | CD (λ = 275 nm) | — | 3.95 (3.82, 4.01) |
| | | Fluorescence | [5]4.92 (4.84, 4.99) | [5]3.83 (3.82, 3.83) |
| | PHS | CD (λ = 222 nm) | 6.38 (6.31, 6.47) | — |
| | | CD (λ = 275 nm) | 6.72 (6.68, 6.76) | 4.47 (4.32, 4.63) |
| | | Fluorescence | [3]6.25 (6.24, 6.26) | [3]4.53 (4.49, 4.57) |
| V66D | Δ + PHS | CD (λ = 222 nm) | [6]9.51 (9.26, 9.74) | [6]10.42 (10.39, 10.45) |
| | | CD (λ = 275 nm) | — | [6]10.40 (10.37, 10.45) |
| | | Fluorescence | [6]9.68 (9.63, 9.72) | [6]10.41 (10.40, 10.42) |
| | PHS | CD (λ = 222 nm) | 7.40 (7.34, 7.47) | — |
| | | CD (λ = 275 nm) | 7.55 (7.50, 7.60) | 9.89 (9.81, 9.97) |
| | | Fluorescence | 8.10 (8.04, 8.16) | 9.97 (9.95, 9.99) |
| V66E | Δ + PHS | CD (λ= 111 nm) | 9.5 (9.2, 9.8) | 10.7 (10.67, 10.73) |
| | | CD (λ = 275 nm) | — | 10.73 (10.66, 10.80) |
| | | Fluorescence | 10.18 (10.12, 10.24) | 10.67 (10.66, 10.69) |
| | PHS | CD (λ = 222 nm) | — | 9.59 (9.49, 9.70) |
| | | CD (λ = 275 nm) | — | 9.88 (9.72, 10.03) |
| | | Fluorescence | [4]9.44 (9.41, 9.47) | [4]10.07 (10.06, 10.08) |

[1]Midpoint of the minor transition.
[2]Midpoint of the cooperative transition corresponding to acid or base unfolding.
[3]Data comparable to these were presented previously (8).
[4]Data comparable to these were presented previously (11).
[5]Data comparable to these were presented previously (7).
[6]Data comparable to these were presented previously (10).

The acid-base titrations of the V66K, V66D and V66E variants in the Δ+PHS background (FIG. 10A-C, green curves) showed evidence of conformational reorganization coincident with the ionization of the internal ionizable groups. This was observed originally with the Δ+PHSN66D variant by far-UV CD at 222 nm (10). This is what prompted the reexamination of the behavior of variants with Glu-66 and Lys-66, for which the effect had gone unnoticed in previous studies with Trp fluorescence. The titration of Δ+PHS/V66E monitored by fluorescence and by near UV CD spectra showed no evidence of a conformational transition in the range of pH 8 to 10 where Glu-66 with a $pK_a$ of 9.1 becomes charged. In contrast, titration monitored by far-UV CD showed evidence for the disruption of α-helix and perhaps even β-sheet concomitant with the ionization of Glu-66. In the Δ+PHS/V66K protein, the coincidence between the pH titration monitored by intrinsic fluorescence and by far-UV CD, and their similarity with the titration of the Δ+PHS protein monitored by Trp fluorescence, obscured the conformational transition. The conformational change coupled to the ionization of Lys-66 with a $pK_a$ of 5.6 was more obvious when the titrations of Δ+PHS/V66K and Δ+PHS were compared in the far-UV and near-UV CD.

far-UV CD signal monitored a monotonic titration in the range coincident with the titration of Asp-66 with a $pK_a$ value of 8 (Table II). The near-UV CD and the intrinsic fluorescence signals exhibited a biphasic response, with a first titration event at pH 8, coincident with the $pK_a$ of Asp-66, and a second, well-defined titration centered near pH 10. This second titration, corresponding to global unfolding by base, was also observed in the PHS/V66E variant.

Effects of Osmolytes on $pK_a$ Values.

To further establish a dependence between the measured $pK_a$ values of internal groups and the stability of the parent protein, some measurements were repeated in the presence of glycerol, which is known to stabilize the native state of SNase (29). In general, stabilizing osmolytes such as sucrose, glycerol and TMAO promote the native states of proteins because unfavorable interactions between backbone and osmolytes are minimized in this state (29).

Figure 11:
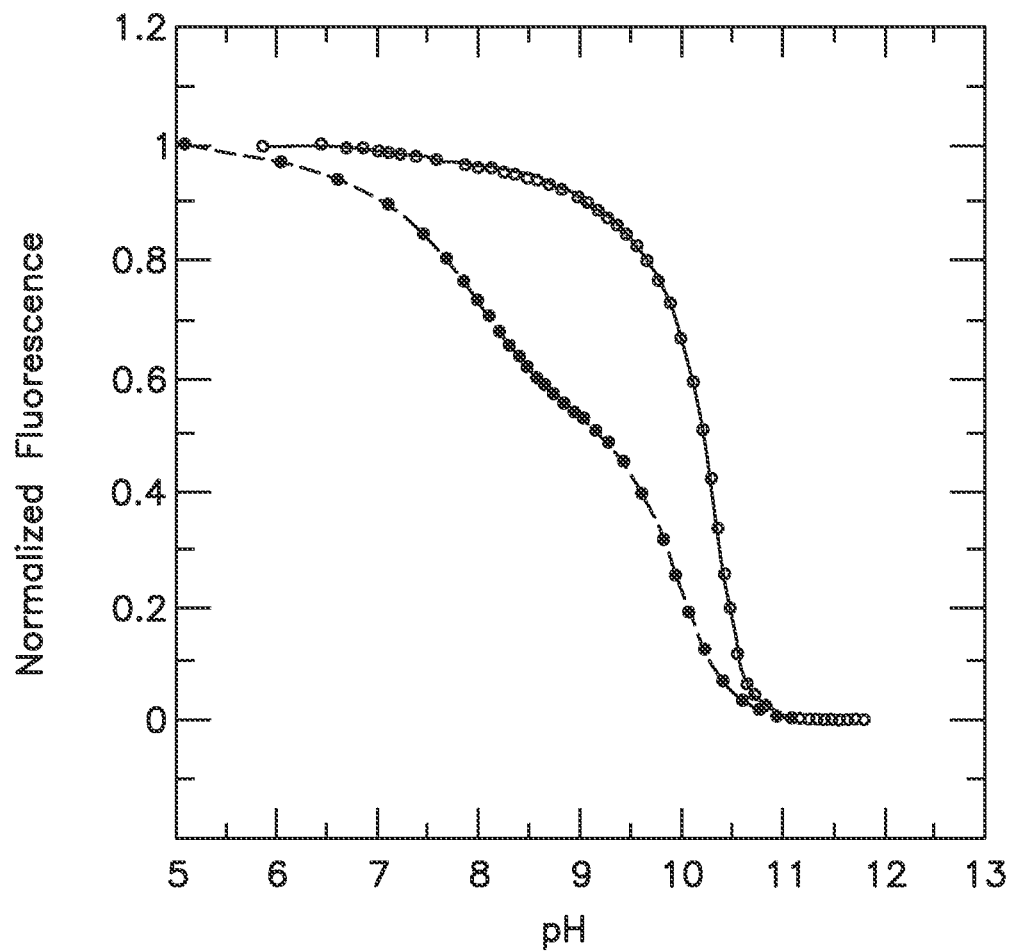
FIG. 11 shows the acid/base titration of PHS/V66D in the absence (•) and in the presence (○) of 4 M glycerol, monitored by Trp fluorescence at 298 K.

Attempts were made to measure the $pK_a$ of Lys-66 in Δ+PHSN66K and of Asp-66 in PHS/V66D by potentiometry in the presence of 4 M glycerol. The stabilizing effects of glycerol were clearly evident in the wider range of pH over which the proteins remained folded (FIG. 11). Because glycerol stabilized the protein, the $pK_a$ value of Lys-66 measured in its presence was expected to be lower than in its absence: conversely, the $pK_a$ value of Asp-66 was expected to be higher. The data were not of the same high quality as those measured in water owing to the difficulties inherent to measurements in viscous solutions in high glycerol concentrations. For this reason we did not obtain $pK_a$ values. However, the trends that were observed are fully consistent with the notion that an agent that stabilizes the native state and which suppresses local and global unfolding leads to even greater shifts in the $pK_a$ values. The biphasic pH titration monitored by fluorescence with the PHS/V66D protein becomes nearly sigmoidal in the presence of 4 M glycerol (FIG. 11), showing clearly that the conformational reorganization coupled to the ionization of Asp-66 was suppressed in the presence of a stabilizing agent. The effects of osmolytes on the $pK_a$ of Lys-66 and Asp-66 were fully consistent with the notion that the $pK_a$ values are governed by the local stability of their microenvironments and by the probability of populating locally or partially unfolded states.

X-ray Crystallography.

Crystal structures have been obtained previously for variants with Lys-66 (7, 9). Asp-66 (10), or Glu-66 (11), but only under conditions of pH where these internal ionizable groups are neutral. We have been unable to grow crystals of any of these variants under conditions of pH where the groups are presumably charged. However, crystals of PHS/V66K grown at pH 7 tolerated transfer to pH≤5, where Lys-66 is likely to be charged. The transfer from high to low pH often led to the cracking of crystals, but by trial and error it eventually became possible to lower the pH of crystals without damaging them.

Figure 12:
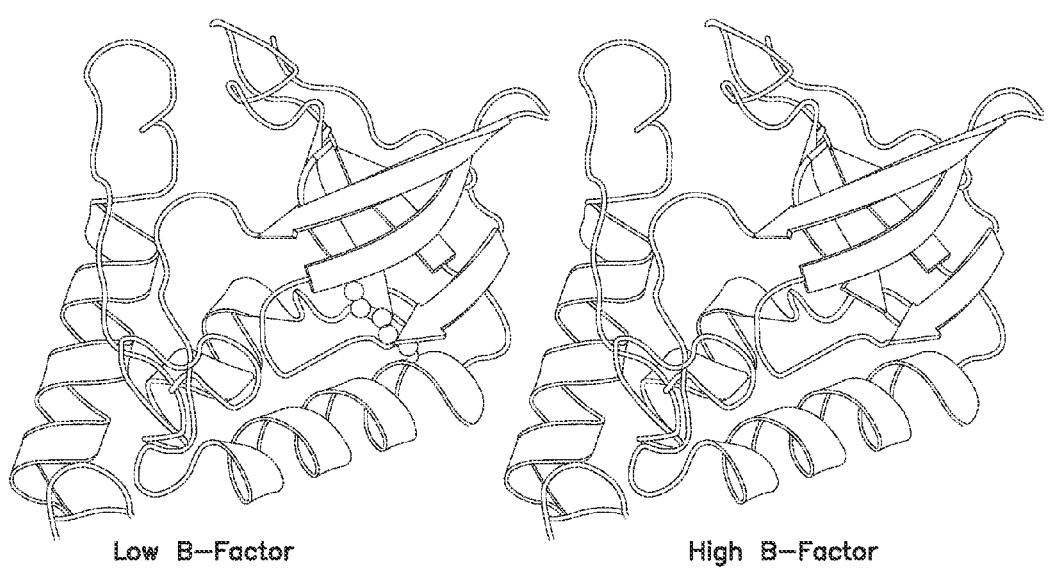
FIG. 12 shows the B factors in the structures of PHS/V66K at pH 7 (left) and pH 4.7 (right). The side chain of Lys-66 is shown as grey spheres in the pH 7 structure. The color bar identifies high and low B factors.

The structures of the V66K variant that were previously available were obtained in the wild type background (9) and in the Δ+PHS background (8) at pH 8 under cryogenic conditions. We obtained the structure of the V66K variant of PHS protein in three conditions: (1) at pH 7 under cryogenic conditions: (2) at pH 5 at room temperature: and (3) at pH 4.7 under cryogenic conditions. The conformation of the backbone of all V66K variants was nearly identical regardless of the conditions or of the background used. The only relevant observation in the structures of the V66K variant at lower pH values was that the electron density for the side chain of the internal Lys-66, which is clearly visible in maps at pH 7, could not be resolved at the lower pH values. At pH 4.75. where in solution Lys-66 is presumably fully charged, there was no density for the side chain, not even for Cβ. The absence of density for Cβ suggested that the backbone in this region of the protein was disordered. Additional evidence for disorder in the backbone came from comparison of the B factors for Cα atoms in the structures obtained under cryogenic conditions at pH 7 and 4.7. In the structure at low pH, where Lys-66 is charged, B factors were significantly higher for the region in the α-helix in the vicinity of residues 66, as well as being somewhat higher in the adjacent β-1 strand (FIG. 12). The more substantial loss of α-helix measured by far UV-CD (FIG. 10C) was not evident in the crystals. Other cases where conformational relaxation induced by the formation of a buried charge is evident in optical spectroscopic methods but not in crystal structures have been reported (30). In the case of the structure with ionized Lys-66, three factors could have stabilized the fully folded state in the crystal and obscured the conformational relaxation observed spectroscopically. First, lattice forces in the crystal can influence the conformation of the protein. Second, the osmotic properties of the solution used to grow crystals must stabilize the native state. Crystals were grown with MPD (2-methyl-2,4-pentanediol), which probably destabilizes SNase, but glycerol was included in the drops, which enhances the stability of SNase. Third, the crystals were grown in the presence of $Ca^{2+}$ and the inhibitor pdTp, which bind at the active site with high affinity and stabilize the native state significantly.

The very large shifts in the $pK_a$ values of Lys-66, Glu-66 and Asp-66 in SNase relative to the normal values in water, and in the direction that favors the neutral state, imply that the microenvironment of the ionizable moieties inside the protein are not as polarizable as water. What is noteworthy is that, although the shifts in $pK_a$ values of these residues are very large, they are actually consistent with high apparent polarizability in the protein interior (7, 10, 11), comparable to that of a material with a dielectric constants of 10. A dielectric constant of 10 is very high relative to the value of 2 to 4 measured with dry protein powders (15-17). It is in the range of dielectric constants expected from highly polar and polarizable materials. Similarly high apparent dielectric constants are reported by naturally occurring internal ionizable groups in active sites of enzymes and in many other types of proteins (1, 2, 8, 31).

The spectroscopic data demonstrate unequivocally that the ionization of Lys-66, Asp-66 and Glu-66 in SNase triggers structural reorganization. Because the probability of structural transitions is determined by the free energy difference between the ground state and the alternative conformational state achieved when the internal ionizable groups are charged, the $pK_a$ values of the internal ionizable groups are sensitive to the global stability of the protein. Structural reorganization was made more readily apparent by lowering modestly the stability of the background protein used to study the ionization of the internal groups. The structural changes coupled to the ionization of the internal groups appear to be subtle, leaving most of the native structure of the protein intact, especially in the more stable Δ+PHS protein. This is consistent with the interpretation given to magnetic relaxation dispersion studies of the V66E and V66K variants of Δ+PHS nuclease (32).

The demonstration that the ionization of an internal group is coupled to a conformational transition and dependent on the global stability of the protein used for the measurements is significant. It implies that the $pK_a$ values of internal groups need not report on the true polarizability of their microenvironment. At least in the case of Lys-66, Asp-66 and Glu-66, their $pK_a$ values report on local or global stability of the protein. The apparent dielectric constants obtained from these $pK_a$ values are not interpretable in terms of dielectric permittivity proper-they reflect the dielectric breakdown of the protein.

Details of the nature of the conformational reorganization coupled to the ionization of Lys, Asp or Glu at position 66 in SNase are not known at this time. NMR spectroscopy studies are underway to examine these conformational transitions in depth. It is likely that in the conformational state stabilized by the ionization of the internal group the previously buried charged moieties are well hydrated. Based on the location of position 66 at the C terminal end of an α-helix (FIG. 11) and on the characteristic loss of intensity in the far-UV CD at 222 nm where α-helices contribute, we speculated (10) that the ionization of Asp-66 triggers the partial unwinding of helix-1. The structural change coupled to the ionization of Lys-66 and Glu-66 is probably similar. The spectroscopic data measured with the variants made with the Δ+PHS background protein suggest that the conformational transition involves subtle local or sub-global rearrangement. In all cases the structural transition triggered by the ionization of the internal groups precedes a steep cooperative transition corresponding to the global acid or base unfolding. This further shows that substantial native-like structure is still present after the internal groups are charged.

The conformational transitions coupled to the ionization of internal groups observed with SNase and with other model proteins (33) is probably similar to the conformational reorganization coupled to the ionization of naturally occurring internal ionizable groups. Conformational transitions coupled to the ionization of naturally occurring internal groups are usually functionally relevant, and an important recurring motif central to energy transduction. For example, the kinetic mechanism of $H^+$ transport in bacteriorhodopsin depends on the modulation of $pK_a$ values through reorganization of main chain and side chain atoms inside the protein (34-36). In ATPase (37) key catalytic events are governed by the coupling between conformational reorganization, the change in the $pK_a$ value of a critical carboxylic group, and a change in its charged state. The photoactive yellow protein undergoes a substantial conformational change in response to the formation of a buried charge during its cycle of biological function (38-40). The partially unfolded state promoted by the ionization of an internal group is the form of this protein that is active in signaling. In all of these cases, the ultimate goal of dissection of structure-function relationships involve understanding the nature of the conformational transition triggered by the ionization of an internal groups.

Demonstration that the $pK_a$ of Lys-66, Asp-66 and Glu-66 in SNase are governed by the stability and conformational reorganization of the protein has significant implications for structure-based $pK_a$ calculations. It is well known that structure-based electrostatic calculations with continuum models overestimate the magnitude of electrostatic effects in proteins (13, 41-44). The properties of internal ionizable groups are notoriously difficult to reproduce with these methods (7, 10, 13, 18, 19). At least in the case of the internal Lys-66, Asp-66 and Glu-66 in SNase, the problems stem from the inability of computational models to account for the energetic consequences of coupling between ionization of an internal residue and conformational reorganization.

The demonstration that the $pK_a$ values of some internal ionizable groups are linked to global and local stability underscores inherent limitations of continuum electrostatics calculations with static structures. The problems can be addressed through the empirical use of high dielectric constants (7, 10, 13, 18, 19), but this is a poor solution to a complex problem. More rigorous methods that employ Monte Carlo side chain repacking (45, 46) or molecular dynamics simulations (47, 48) are available. Spectroscopic evidence showing that the conformation of the backbone changes during the titration of internal ionizable groups suggests that methods capable of sampling alternate conformations of the backbone will be necessary to study biologically important processes governed by the ionization of internal groups. A variety of novel computational methods have been proposed for these purposes (49-53). These methods attempt to calculate $pK_a$ values of internal ionizable groups by reproducing conformational transitions coupled to their ionization, as proposed originally by Warshel and co-workers in their PDLD/S-LRA algorithm (36). Doing this accurately will require calculation of the thermodynamic stability of proteins, which is still a challenging undertaking. At the very least, it will be necessary to drive the protein across a free energy landscape, pushing it out of local minima, with self-consistent evaluation of free energy along the way (54).

Finally, we note that substitution of internal hydrophobic residues with ionizable ones turns out to be a useful strategy for mapping the folding free energy landscapes of proteins. Because folding is usually highly cooperative, folding intermediates are suppressed, presently only transiently, and difficult to study. Our results suggest that by charging an internal group it is possible to stabilize the partially unfolded state that can then be studied with equilibrium thermodynamic methods. We speculate that the driving force behind the partial or local unfolding promoted by the ionization of an internal group is the need for the internal charge to be hydrated. Sometimes this will be achieved by the penetration of water into the protein. Clearly, in other cases, when partially folded states in which the internal charge is hydrated are accessible, the ionization of the internal group will promote these alternative, partially folded states. Although it will be difficult to establish that these partially folded states are relevant to the protein folding reaction proper, the possibility of measuring the free energy distance between the fully folded state and many such partially unfolded states would give truly novel insight into the properties of the folding free energy landscape of proteins.

REFERENCES

Each of the following publications is incorporated herein by reference.
1. Li, Y., Kuliopulos, A., Mildvan, A. S., and TalaJay, P. (1993) Environments and Mechanistic Roles of the Tyrosine Residues of A5-3-Ketosteroid Isomerase, Biochemistry 32, 1816-1824.
2. Czerwinski, R. M., Harris, T. K., Massiah, M. A., Mildvan, A. S., and Whitman, C. W. (2001) The structural basis for the perturbed $pK_a$ of the catalytic base in 4-oxalocrotonate tautomerase: Kinetic and structural effects of mutations of Phe-50, Biochemistry 40, 1984-1995.
3. Luecke, H., and Lanyi, J. K. (2003) Structural Clues to the Mechanism of Ion Pumping in Bacteriorhodopsin, Advances in Protein Chemistry 63, 115-130.
4. Parson, W. W., Chu, Z. T., and Warshel, A. (1990) Electrostatic control of charge separation in bacterial photosynthesis, Biochim. Biophys. Acta 1017, 251-272.
5. Doyle, D. A., Cabral, J. M., Pfuetzner, R. A., Kuo, A., Gulbis, J M., Cohen, S. L., Chait, B. T., and MacKinnon, R. (1998) The Structure of the Potassium Channel: Molecular Basis of $K^+$ Conduction and Selectivity, Science 280, 69-11.
6. Burykin, A., and Warshel, A. (2003) What Really Prevents Proton Transport through Aquoporin? Charge Self-Energy versus Proton Wire Proposals, Biophysical J. 85, 3696-3706.
7. Fitch, C. A., Karp, D. A., Lee, K. K., Stites, W. E., Lattman, E. E., and Garcia-Moreno E., B. (2002) Experimental $pK_a$ values of buried residues: analysis with continuum methods and role of water penetration. Biophysical Journal 82, 3289-3304.
8. Garcia-Moreno E., B., Dwyer, J., Gittis, A., Lattman, E., Spencer. D., and Stites, W. (1997) Experimental measurement of the effective dielectric in the hydrophobic core of a protein. Biophysical Chemistry 64, 211-224.
9. Stites. W. E., Gittis, A. G., Lattman, E. E., and Shortle, D. (1991) In a staphylococcal nuclease mutant the side-chain of a lysine replacing valine 66 is fully buried in the hydrophobic core, Journal of Molecular Biology 221, 7-14.
10. Karp, D. A., Gittis, A. G., Stahley, M. R., Fitch, C. A., Stites, W. E., and Garcia-Moreno E., B. (2007) High Apparent Dielectric Constant Inside a Protein Reflects Structural Reorganization Coupled to the Ionization of an Internal Asp, Biophysical Journal 92, 2041-2053.
11. Dwyer, J., Gittis, A., Karp, D., Lattman, E., Spencer, D., Stites, W., and Garcia-Moreno E., B. (2000) High apparent dielectric constants in the interior of a protein reflect water penetration. Biophysical Journal 79, 1610-1620.
12. Schlessman, J. L., Abe, C, Gittis, A. G., Karp, D. A., Dolan, M. A., and Garcia-Moreno E., B. (2008) Crystallographic study of hydration of an internal cavity in engineered proteins with buried polar or ionizable groups, Biophys. J. 94, 3208-3216.
13. Schutz, C. N., and Warshel, A. (2001) What are the dielectric "constants" of proteins and how to validate electrostatic models?. Proteins. Structure, Function, and Genetics 44, 400-417.
14. Pethig, R. (1979) Dielectric and Electronic Properties of Biological Materials, John Wiley and Sons, Chichester.
15. Harvey, S. C, and Hoekstra, P. (1972) Dielectric relaxation spectra of water adsorbed on lysozyme, Journal of Physical Chemistry 76, 1987-2994.
16. Bone, S., and Pethig, R. (1985) Dielectric studies of protein hydration and hydration-induced flexibility. Journal of Molecular Biology 181, 323-326.
17. Bone, S., and Pethig, R. (1982) Dielectric studies of the binding of water to lysozyme. Journal of Molecular Biology 157, 571-575.
18. Harms, M. J. Castaneda, C. A., Schlessman, J. L., Suc, G. R., Isom, D. G., Cannon, B. R., and Garcia-Moreno E., B. (2009) The $pK_a$ values of acidic and basic residues buried at the same internal location in a protein are governed by different factors, J. Mol. Biol. 389, 34-41.
19. Harms, M. J., Schlessman. J. L., Chimenti, M. S., Sue, G R., Damjanovic, A., and Garcia-Moreno E., B. (2008) A buried lysine that titrates with a normal $pK_a$: Role of conformational flexibility at the protein water interface as a determinant of $pK_a$ values, Protein Science 17, 833-845.
20. Shortle, D., and Meeker, A. (1986) Mutant forms of staphylococcal nuclease with altered patterns of guanidine hydrochloride and urea denaturation, Proteins: Structure, Function, and Genetics 1, 81-89.
21. Byrne, M., Manuel, R., Lowe, L., and Stites, W. (1995) Energetic contribution of side chain hydrogen bonding to the stability of staphylococcal nuclease. Biochemistry 34, 13949-13960.
22. Gill, S. C., and Von Hippel, P. H. (1989) Calculation of protein extinction coefficients from amino acid sequences, Analytical Biochemistry 182, 319-326.
23. Whitten, S. T., and Garcia-Moreno E., B. (2000) pH dependence of stability of staphylococcal nuclease: Evidence of substantial electrostatic interactions in the denatured state. Biochemistry 39, 14292-14304.
24. Jones, T. A., Zhou, J.-Y., Cowan, S. W., and Kjddgaard, M. (1991) Improved methods fur building protein models into electron density maps and the location of errors in these models, Acta Crystallographica A. 47, 110-119.
25. Briinger, A., Adams, P., Clore, G., DeLanu, W., Grus, P., Grossc-Kunstlevc, R., Jiang, J., Kuszewski, J., Nilges, M., Pannu, N., Read, R., Rice, L., Simonson, T., and Warren, G. (1998) Crystallography & NMR system: A new software suite for macromolecular structure determination, Acta Crystallographica, Section D: Biological Crystallography 54 (Pt 5), 905-921.
26. Isom, D. G., Cannon, B. R., Castaneda, C. A., Robinson, A., and Garcia-Moreno E., B. (2008) High tolerance for ionizable residues in the hydrophobic interior of proteins, Proc. Natl. Acad. Sci. USA 105, 17784-17788.
27. Su, Z., Wu, J., Fang, H., Tsong, T., and Chen, H. (2005) Local stability identification and the role of a key aromatic amino acid residue in staphylococcal nuclease, FEBS Journal 272, 3960-3966.
28. Hirano, S., Kamikubo, H., Yamazaki, Y., and Kataoka, M. (2005) Elucidation of information encoded in tryptophan 140 of staphylococcal nuclease, Proteins: Structure, Function, and Bioinformatics 58, 271-277.
29. Baskakov, I. V., and Bolen, D. W (1998) Monitoring the sizes of denatured ensembles of staphlococcal nuclease proteins, implications regarding m values, intermediates, and thermodynamics, Biochemistry 37, 18010-18017.
30. Van Aaltcn, D. M. F., Crielaard, W., Hellingwerf, K. J., and Joshua-Tor, L. (2000) Conformational substrates in different crystal forms of the photoactive yellow protein—Correlation with theoretical and experimental flexibility, Protein Science 9, 64-72.
31. Ho, M., Mcnetrct, J., Tsuruta, H., and Allen, K. N. (2009) The origin of the electrostatic perturbation in acetoacetate decarboxylase, Nature 459, 393-399.
32. Denisov, V. P., Schlessman, J. L., Garcia-Moreno E., B., and Halle, B. (2004) Stabilization of Internal Charges in a Protein: Water Penetration or Conformational Change?, Biophysical J. 87, 3982-3994.
33. Dao-pin, S., Anderson, D. E., Baasc, W. A., Dahlquist, F W., and Matthews, B. W. (1991) Structural and thermodynamic consequences of burying a charged residue within the hydrophobic core of T4 lysozyme, Biochemistry 30, 11521-11529.
34. Brown, L. S., Kamikubo, H., Zimanyi, L., Kataoka, M., Tokunaga, F., Verdegem, P., Lugtcnburg, J., and Lanyi, J. K. (1997) A local electrostatic change is the cause of the large-scale protein conformation shift in bacteriorhodopsin, Proceedings of the National Academy of Sciences USA 944, 5040-5044.
35. Lanyi, J. K. (2000) Crystallographic studies of the conformational changes that drive directional transmembrane ion movement in bacteriorhodopsin, Biochimica et Biophysica Acta 1459, 339-345.
36. Song, Y., Mao, J., and Gunner, M. R. (2003) Calculation of Proton Transfers in Bacteriorhodopsin bR and M Intermediates, Biochemistry 42, 9875-9888.
37. Rastogi, V. K., and Girvin, M. E. (1999) Structural changes linked to proton translocation by subunit c of the ATPase synthase, Nature 402, 263-268.
38. Xic, A., Kclemen, L., Hendriks, J., White, B. J., Hellingwerf, K. J., and Hoff, W. D. (2001) Formation of a New Buried Charge Drives a Large-Amplitude Protein Quake in Photoreceptor Activation, Biochemistry 40, 1510-1517.
39. Lee, B., Croonquist, P A., Sosnick, T. R., and Hoff, W. D. (2001) PAS Domain Receptor Photoactive Yellow Protein Is Converted to a Molten Globule State upon Activation. J. Biol. Chem. 276, 20821-20823.
40. Hoff, W. D., Xic, A., Van Stokkum, I. H. M., Tang, X., Gural, J., Kroon, A. R, and Kellingwerf, K. J. (1999) Global Conformational Changes upon Receptor Stimulation in Photoactive Yellow Protein, Biochemistry 38.
41. Castaneda, C. A., Fitch, C. A., Majumdar, A., Khangulov, V., Schlessman, J. L., and Garcia-Moreno E., B. (2009) Molecular determinants of the $pK_a$ values of Asp 42. Forsyth, W. R., Gilson, M. K., Antosicwicz, J., Jaren, O. R., and Robertson, A. D. (1998) Theoretical and experimental analysis of ionization equilibria in ovomucoid third domain, Biochemistry 37, 8643-8652.
43. Antosicwicz, J., Mc Cammon, A. J., and Gilson, M. K. (1996) The determinants of $pK_{a's}$ in proteins, Biochemistry 35, 7819-7833.
44. Antosicwicz, J., McCammon, J. A., and Gilson, M. K. (1994) Prediction of pH-dependent properties of proteins, Journal of Molecular Biology 238, 415-436.
45. Georgescu, R. E., Alexov, E. G., and Gunner, M. R. (2002) Combining conformational flexibility and continuum electrostaics for calculating $pK_{a's}$ in proteins. Biophysical Journal 83, 1731-1748.
46. Alexov, E. (2003) Role of the protein side-chain fluctuations on the strength of pair-wise electrostatic interactions comparing experimental with computed $pK_{a's}$, Proteins: Structure, Function, and Genetics 50, 94-103.
47. Kuhn, B., Kollman, P. A., and Stahl, M. (2004) Prediction of $pK_a$ shifts in proteins using a combination of molecular mechanical and continuum solvent calculations, Journal of Computational Chemistry 25, 1865-1872.
48. van Vlijmen, H. W. T., Schaefer, M., and Karplus, M. (1998) Improving the accuracy of protein $pK_a$ calculations: Conformational averaging versus the average structure. Proteins. Structure, Function, and Genetics 33, 145-158.
49. Ghosh, N., and Cui, Q. (2008) $pK_a$ of residue 66 in staphylococcal nuclease. I. Insights from QM/MM simulations with conventional sampling, Phys. Chem. B. 112, 8387-8397.
50. Zheng, L., Mengen, C, and Yang, W. (2008) Random walk in orthogonal space to achieve efficient free-energy simulation of complex systems, Proc. Natl. Acad. Sci. USA 105, 20221-20232.
51. Kato, M., and Warshel, A. (2006) Using a charging coordinate in studies of ionization induced partial unfolding, J. Phys. Chem. B. 110, 11566-11579.
52. Khandogin, J., and Brooks, C. L. (2005) Constant pH molecular dynamics with proton tautomerism, Biophysical J. 89, 141-157.
53. Khandogin, J., and Brooks, C. L. I. (2006) Towards the accurate first-principles prediction of ionization equilibria in proteins. Biochemistry 45, 9363-9373.

Large shifts in $pK_a$ values of lysine residues buried inside a protein.

Internal ionizable groups in proteins are relatively rare but they are essential for catalysis and energy transduction. To examine molecular determinants of their unusual and functionally important properties, we engineered 25 variants of staphylococcal nuclease with lysine residues at internal positions. 19 of the Lys residues have depressed $pK_a$ values, some as low as 5.3, and 20 titrate without triggering any detectable conformational reorganization. Apparently, simply by being buried in the protein interior these Lys residues acquired $pK_a$ values comparable to those of naturally occurring internal ionizable groups involved in catalysis and biological $H^+$ transport. The $pK_a$ values of some of the internal Lys residues were affected by interactions with surface carboxylic groups. The apparent polarizability reported by the $pK_a$ values varied significantly from location to location inside the protein. These data will enable an unprecedented examination of the positional dependence of the dielectric response of a protein. This study shows that the ability of proteins to withstand the presence of internal charges in their hydrophobic interior is a fundamental property inherent to all stable proteins, not a specialized adaptation unique to proteins that evolved to depend on internal charges for function.

Internal ionizable groups in proteins are essential for catalysis and for most forms of biological energy transduction. During a cycle of function these internal ionizable groups can experience different microenvironments and their $pK_a$ values and charged states adjust accordingly (1). In highly polar or polarizable microenvironments the charged form of an ionizable group will predominate. In less polar or polarizable microenvironments the neutral form will be favored and the $pK_a$ values will be shifted relative to the normal values in water (for acidic groups the $pK_a$ values will tend to be higher than the normal $pK_a$ values (2-4); for basic groups the $pK_a$ values will tend to be lower than the normal values (5-7)). For proteins that depend on internal ionizable groups for function, the structural basis of function cannot be established without knowing the $pK_a$ values of the internal groups and understanding the factors that determine them. This remains extremely challenging; the $pK_a$ values of internal groups are notoriously difficult to measure and structure-based electrostatics calculations cannot yet be used reliably for calculations with internal groups (8-10).

To examine determinants of the unusual properties of internal ionizable groups in proteins, we measured $pK_a$ values systematically with a family of engineered variants of SNase with Lys at 25 internal positions (11). Although some internal ionizable groups can actually stabilize the folded state, even when they are charged (12), in general proteins are destabilized significantly by the presence of ionizable groups in their hydrophobic interior. The stability of most of these Lys-containing variants was highly dependent on pH, indicating that the $pK_a$ values of the introduced side chains were shifted relative to their normal $pK_a$ values in water (11). Previous studies of internal Glu residues showed that their $pK_a$ values can be much higher than the normal $pK_a$ of a 4.5 for Glu in water, and that the ionization of internal Glu need not affect the conformation of the protein (13). Because the apparent dielectric response to different types of ionizable groups at the same internal location of a protein need not be equivalent, it was of great interest to study the properties of internal Lys residues systematically.

The Glu and Lys side chains differ in their size, flexibility, hydrophobicity, hydration, polarity, hydrogen bonding potential and charge density. Carboxylic side chains are not ideal for examining polarity and polarizability in internal locations in proteins because their charge is delocalized and distributed over a large volume, which in turn affects the hydration free energy of the charged moiety and also its ability to polarize its microenvironment. The carboxylic group also has a higher hydrogen bonding potential than the primary amino group in Lys residues, and in general it is also better hydrated than the amino group, even in internal locations secluded from bulk water (14-16). Because the charge in a Lys side chain is concentrated on a single atom and because it is rarely buried in a hydrated state, Lys residues are likely to be more useful than Glu side chains to probe the dielectric response inside a protein (16).

By measuring $pK_a$ values for many internal Lys residues it was possible to describe, on a site-by-site basis, the ability of a protein to accommodate positive charge throughout its interior. The results of this study will enable detailed examination of molecular determinants of the dielectric properties of proteins at an unprecedented level of detail. This systematic study of $pK_a$ values of internal groups will promote critical evaluation of computational methods for structure-based calculation of electrostatic effects in proteins (9). It also contributes insight into structural and physical origins of the biologically essential ability of proteins to withstand the presence of internal charges, which is a property fundamental for energy transduction processes.

Measurement of $pK_a$ Values from the pH Dependence of Thermodynamic Stability.

The $pK_a$ values of internal ionizable groups are usually highly sensitive to protein conformation. In the unfolded ensemble (U), the side chains of all ionizable groups are hydrated and the $pK_a$ values are mostly normal. In the folded state (F), the $pK_a$ values of internal groups will vary depending on their location and on the polarity and polarizability of their microenvironments. In highly polar or polarizable internal microenvironments, the $pK_a$ values will tend to be like those in water but in microenvironments that are less polar or polarizable, the $pK_a$ values will shift in the direction that favors the neutral state. In general, the $pK_a$ values of internal groups in proteins will be shifted relative to the normal $pK_a$ values in water. This coupling between $pK_a$ and protein conformation is responsible for the pH dependence of thermodynamic stability ($\Delta G°_{H2O}$):

$$\Delta G_i^o = RT \ln \frac{1 + e^{z2.3(pH - pK_a^U)}}{1 + e^{z2.3(pH - pK_a^F)}} \quad (1)$$

$\Delta G°_i$ is the contribution of a single ionizable group to stability, z is the charge of the ionizable side chain, and $pK_a^F$ and $pK_a^U$ are $pK_a$ values of the ionizable group in the F and U ensembles. Equation 1 shows that $pK_a^F$ and $pK_a^U$ must be different if ionizable group i is to make a net contribution to protein stability at any pH value, and it shows that the stability of a protein changes by 1.36 kcal/mol (298 K) for every unit $pK_a$ difference between $pK_a^F$ and $pK_a^U$.

Figure 13A:
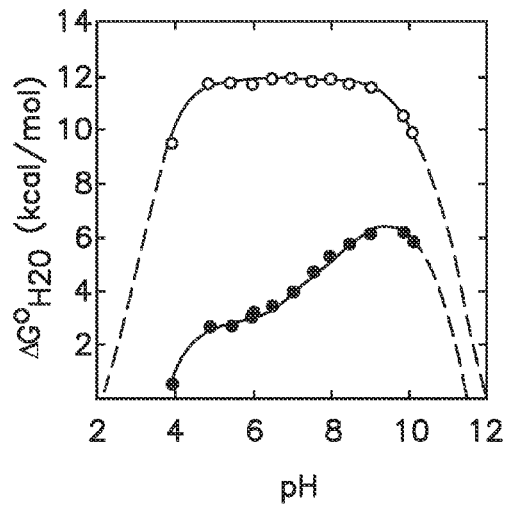
FIG. 13. Measurement of $pK_a$ values through linkage analysis of the pH dependence of thermodynamic stability. (A) Thermodynamic stability ($\Delta G°_{H2O}$) of reference protein (Δ+PHS nuclease) (○) and its L125K variant (●) measured by GdnHCl denaturation monitored by Trp fluorescence. The line is from a simulation and it is only meant to guide the eye. (B) Difference in thermodynamic stability of Δ+PHS and the L125K variant (variant—reference). The line describes the fit of Equation 2 to the data. The $pK_a$ of Lys-125 in folded ($pK_a^F$) and denatured ($pK_a^U$) states are indicated. (C) Thermodynamic stability of Δ+PHS nuclease (○) and of its T62K variant (●) measured by GdnHCl denaturation monitored by Trp fluorescence. The line is from a simulation and it is only meant to guide the eye. (D) Difference in thermodynamic stability of Δ+PHS and the T62K variant (variant—reference). The line describes the fit of Equation 3 to the data. The $pK_a$ values relevant to Lys-62 ($pK_a^F$ and $pK_a^U$) and the phenomenological $pK_a$ values ($pK_a^A$ and $pK_a^B$) of other ionizable side chain (s) affected by Lys-62 are indicated.
Figure 13C:
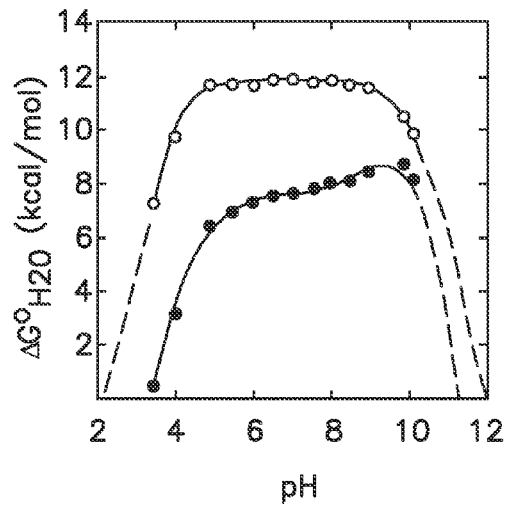
Figure 13B:
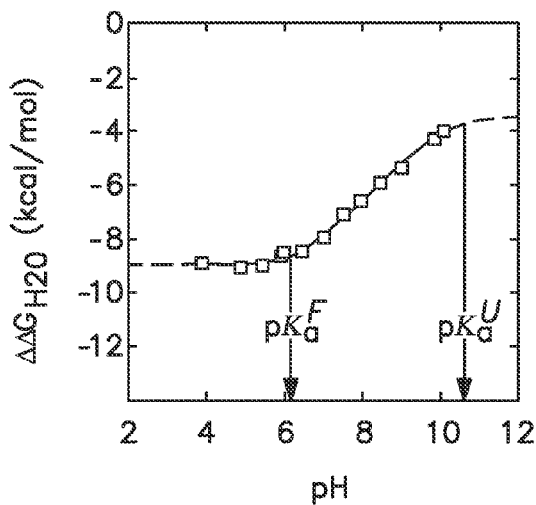

The thermodynamic stability of the Δ+PHS variant of SNase (Δ+PHS is the stabilized form of SNase used as the reference protein in these studies) used for these studies is relatively invariant between pH 5 and 10 and declines rapidly in the acidic and basic limits (FIGS. 13A and 13C). The introduction of a buried Lys with a depressed $pK_a$ leads to a steep dependence of stability between pH 5 and 10 (FIGS. 13A and 13C). If the Lys side chain does not alter the $pK_a$ values of any of the other ionizable side chains of the protein, the difference in the pH dependence of stability ($\Delta\Delta G°_{H2O}$) between the reference and variant protein can be attributed to the shift in the $pK_a$ of the introduced Lys residue (FIG. 13B). This $pK_a$ value can be determined by fitting the $\Delta\Delta G°_{H2O}$ vs pH profile with this relationship (2, 4, 7).

$$\Delta\Delta G^o_{H2O}(pH) = \Delta\Delta G^o_{H2O,mut} - RT \ln \frac{1 + e^{z2.3(pH - pK_a^U)}}{1 + e^{z2.3(pH - pK_a^F)}} \quad (2)$$

$\Delta\Delta G°_{H2O}$ is the pH-dependent difference in stability between a reference protein and a variant with one internal Lys. $\Delta\Delta G°_{H2O,mut}$ is the free energy difference between the reference protein and the variant under conditions of pH where the internal Lys is neutral. The validity of measurement of $pK_a$ values of internal groups by analysis of $\Delta\Delta G°_{H2O}$ vs pH profiles has been corroborated previously by independent measurements with other equilibrium thermodynamic methods (2, 4-6), including NMR spectroscopy (3, 17).

Figure 13D:
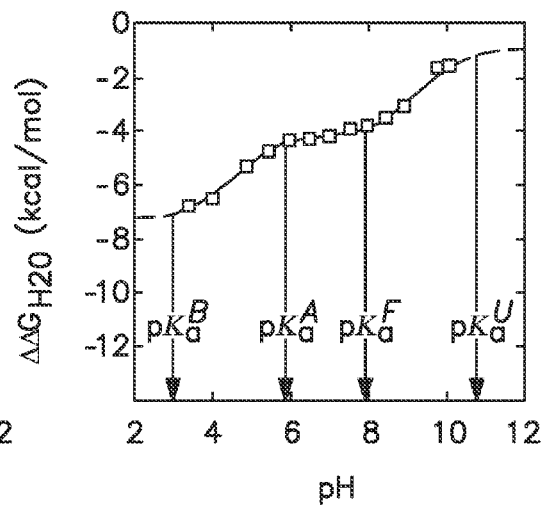

When the internal Lys residue affects the $pK_a$ of one or more ionizable groups, either directly through Coulomb interactions or indirectly by affecting the protein's conformation, the $\Delta\Delta G°_{H2O}$ vs pH profile is more complex and may exhibit more than one distinct region of pH dependence (FIG. 13D). In this case, the observed pH dependence of relative stability can be described phenomenologically with this relationship, $$\Delta\Delta G^o_{H2O}(pH) = \quad (3)$$

$$\Delta\Delta G^o_{H2O,mut} - RT \ln \frac{1 + e^{z2.3(pH - pK_a^U)}}{1 + e^{z2.3(pH - pK_a^F)}} - RT \ln \frac{1 + e^{z2.3(pH - pK_a^{U*})}}{1 + e^{z2.3(pH - pK_a^{F*})}}$$

$pK_a^F$ and $pK_a^U$ represent the $pK_a$ of the internal Lys residue and $pK_a^{F*}$ and $pK_a^{U*}$ represent the apparent $pK_a$ of an ionizable group, or more than one, that are perturbed by the presence of the internal Lys.

In 16 of the 25 Lys-containing variants the $\Delta\Delta G°_{H2O}$ vs pH curve was governed by the substantial depression in the $pK_a$ of the internal Lys without any apparent contributions from shifts in the $pK_a$ of other ionizable groups (FIGS. 13A and 13B). These cases were analyzed with Equation 2. For ten variants (Lys-23, Lys-34, Lys-36, Lys-41, Lys-62, Lys-90, Lys-103, Lys-72, Lys-104, Lys-109) the $\Delta\Delta G°_{H2O}$ vs pH profiles showed clear evidence of contributions from one or more ionizable group whose $pK_a$ was affected by the ionization of the internal Lys (FIGS. 13C and 13D). These cases were analyzed using Equation 3 and the higher of the two $pK_a$ values resolved with Equation 3 was assumed to represent the $pK_a$ of the internal Lys.

Figure 14A:
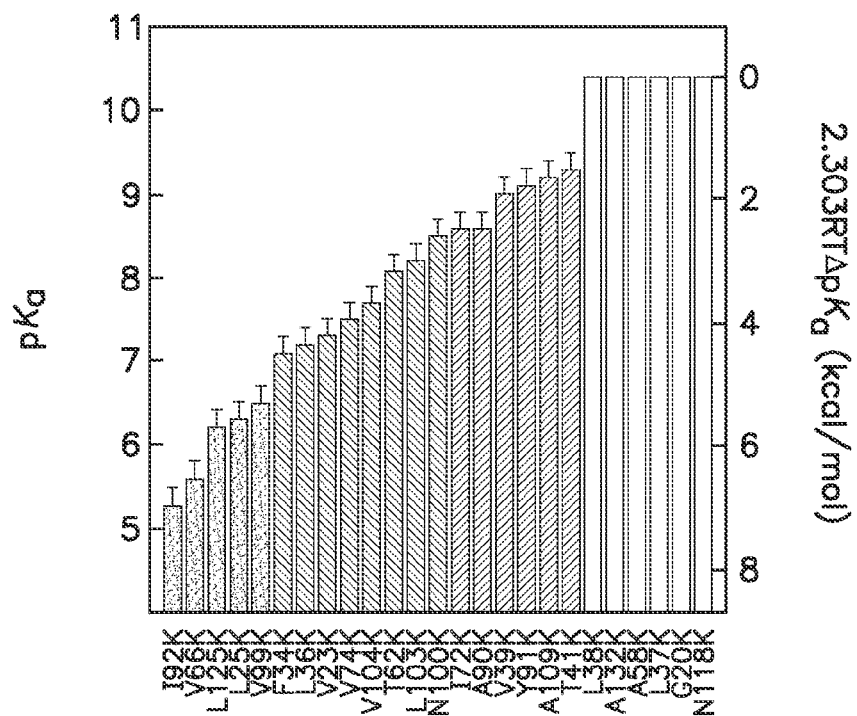
FIG. 14. $pK_a$ values of Lys at 25 internal positions. (A) $pK_a$ values. White bars identify groups that do not exhibit a detectable shift in $pK_a$ value. Colors are only meant to separate arbitrarily small, medium and large shifts in $pK_a$ values (B) Distribution of internal Lys residues in the structure of Δ+PHS nuclease (PDB accession code 3bdc (34)), color-coded according to the magnitude of the shift in $pK_a$ relative to the normal value of 10.4 for Lys in water, as represented in panel (A).
Figure 14B:
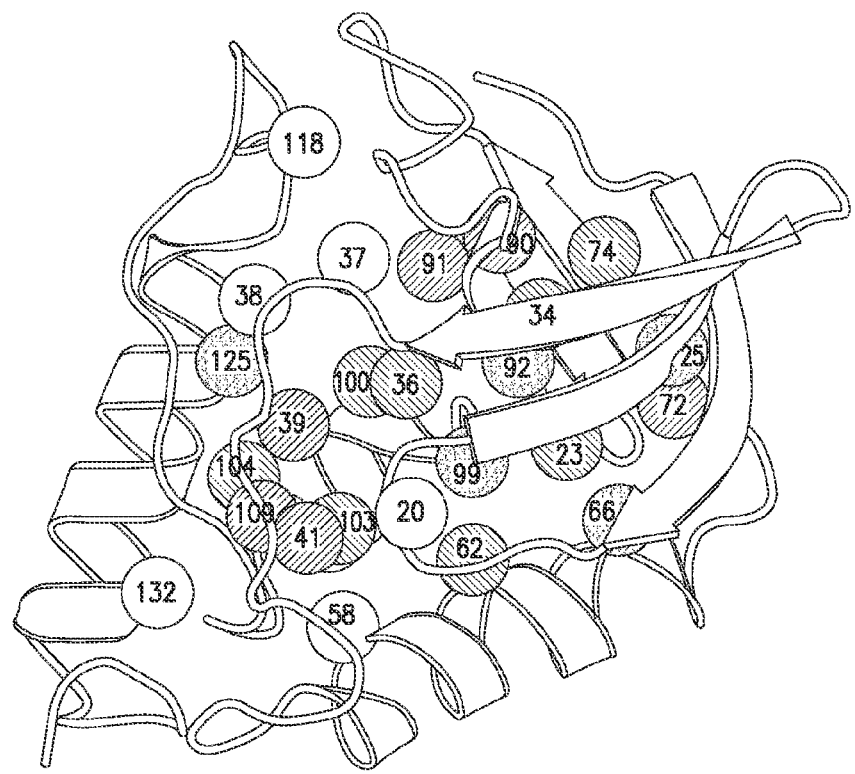

$pK_a$ values of 25 internal Lys residues. Only 6 of the 25 variants with internal Lys residues (Lys-20, Lys-37, Lys-38, Lys-58, Lys-118 and Lys-132) had $\Delta\Delta G°_{H2O}$ vs pH profiles that were independent of pH, implying that the internal Lys residues had near normal pKa≥10 (Table 5, FIG. 14). Most of these Lys residues are in loops and at the ends of elements of secondary structure (FIG. 14B), where fraying might lead to the exposure of the putatively buried group to water. Alternatively, the Lys residues with normal $pK_a$ values are buried but sampling highly dynamic, polar or hydrated microenvironments, as has been shown previously for Lys-38 (3, 17).

TABLE 5

Apparent $pK_a$ values of Lys residues at 25 internal positions of SNase

| Position | $^a pK_a$ | $^b\square_{app}$ | $^c\square G°_{ion}$ | $^d\square G°_{H2O}$ | $^e pH_{mid}$ FL | $^e pH_{mid}$ CD |
|---|---|---|---|---|---|---|
| I92K | 5.3 | 8 | 6.9 | 0.8 | 4.8 | 5.0 |
| V66K | 5.6 | 9 | 6.5 | 3.2$^g$ | 3.8 | 3.9 |
| L125K | 6.2 | 10 | 5.7 | 3.2 | 3.9 | 3.9 |
| L25K | 6.3 | 10 | 5.6 | 3.4 | 3.8 | 3.8 |
| V99K | 6.5 | 11 | 5.3 | 2.5 | 4.3 | 4.3 |
| F34K$^h$ | 7.1 | 12 | 4.5 | 4.2 | 3.8 | 3.9 |
| L36K$^h$ | 7.2 | 12 | 4.4 | 4.7 | 4.1 | 4.1 |
| V23K$^h$ | 7.3 | 13 | 4.2 | 5.2 | 4.0 | 4.0 |
| V74K | 7.4 | 13 | 4.1 | 4.8 | 3.7 | 3.7 |
| V104K$^h$ | 7.7 | 14 | 3.7 | 3.8 | 3.9 | 3.9 |
| T62K$^h$ | 8.1 | 16 | 3.1 | 8.0 | 3.3 | 3.4 |
| L103K$^h$ | 8.2 | 16 | 3.0 | 6.4 | 3.6 | 3.7 |
| I72K$^h$ | 8.6 | 19 | 2.4 | 5.6 | 3.4 | 3.4 |
| A90K$^h$ | 8.6 | 19 | 2.4 | 4.5 | 3.8 | 3.8 |
| N100K | 8.6 | 19 | 2.4 | 1.5 | 4.5 | 4.5 |

TABLE 5-continued

Apparent $pK_a$ values of Lys residues at 25 internal positions of SNase

| Position | [a]$pK_a$ | [b]$\epsilon_{app}$ | [c]$\Delta G°_{ion}$ | [d]$\Delta G°_{H2O}$ | [e]$pH_{mid}$ FL | [f]$pH_{mid}$ CD |
|---|---|---|---|---|---|---|
| V39K | 9.0 | 22 | 1.9 | 4.5 | 3.5 | 3.6 |
| Y91K | 9.0 | 22 | 1.9 | 4.9 | 3.6 | 3.5 |
| A109K[h] | 9.2 | 24 | 1.6 | 7.6 | 3.3 | 3.3 |
| T41K[h] | 9.3 | 26 | 1.5 | 9.5 | 3.0 | 2.9 |
| G20K | 10.4 | — | — | 7.5 | 3.2 | 3.1 |
| L37K | 10.4 | — | — | 7.9 | 2.8 | 2.7 |
| L38K | 10.4 | — | — | 7.5 | 2.8 | 2.8 |
| A58K | 10.4 | — | — | 6.6 | 3.3 | 3.3 |
| N118K | 10.4 | — | — | 8.8 | 2.6 | 2.4 |
| A132K | 10.4 | — | — | 4.6 | 3.3 | 3.4 |

[a]Apparent $pK_a$ values. Estimated experimental error was 0.2.
[b]Apparent dielectric constant(2), calculated with Equation 4 using $\Delta G°_{ion}$ on the left side of the equation, $r_{ion} = 2$ Å, $r_{prot} = 12$ Å(2).
[c]Calculated as 1.36 * ($pK_a - pK_{a,mod}$), assuming a $pK_{a,mod}$ of 10.4. Estimated uncertainty, based on the uncertainty in apparent $pK_a$, is between 0.2 and 0.3 kcal/mol.
[d]Thermodynamic stability of the protein at the apparent $pK_a$, measured by GdnHCl titration monitored by Trp fluorescence, as described previously (31). The experimental error of the reported free energies ranges from 0.1 and 0.4 kcal/mol.
[e]Midpoint of the major acid unfolding transition monitored by Trp fluorescence. In all cases, the experimental uncertainty is 0.1 pH units.
[f]Midpoint of the major acid unfolding transition monitored by CD. In all cases, the experimental uncertainty is 0.1 pH units.
[g]Data from Fitch et al (5).
[h]$pK_a$ values were obtained using Eq. 3. All other $pK_a$ values were obtained using Eq. 2.

$pK_a$ values of 25 internal Lys residues. Only 6 of the 25 variants with internal Lys residues (Lys-20, Lys-37, Lys-38, Lys-58, Lys-118 and Lys-132) had $\Delta\Delta G°_{H2O}$ vs pH profiles that were independent of pH, implying that the internal Lys residues had near normal $pK_a \geq 10$ (Table 5, FIG. 14). Most of these Lys residues are in loops and at the ends of elements of secondary structure (FIG. 14B), where fraying might lead to the exposure of the putatively buried group to water. Alternatively, the Lys residues with normal $pK_a$ values are buried but sampling highly dynamic, polar or hydrated microenvironments. Nineteen of the 25 internal Lys residues exhibited shifted $pK_a$ values depressed below the normal $pK_a$ of 10.4 for Lys in water (Table 5 and FIG. 14A). These $pK_a$ shifts are consistent with the few known $pK_a$ values measured for naturally occurring internal Lys residues (18). In fact, the data show that simply by virtue of being internal, the internal Lys residues in SNase achieved $pK_a$ values comparable to those of naturally occurring internal Lys involved in H[+]-activated processes (18). Some of the $pK_a$ values for Lys in SNase were depressed by more than 5 units and constitute some of the largest shifts in $pK_a$ ever measured. The depression of $pK_a$ values of basic residues implies that the neutral form of the side chain is favored, consistent with the Lys side chains being buried in at least a partially dehydrated form, and in microenvironments that are less polar and polarizable than water. The buried nature of some of the ionizable side chains engineered to be internal is being corroborated by crystal structures of many of the variants. Thus far, in over 25 structures of variants of SNase with Lys, Glu or Asp at some of the 25 internal positions (the coordinates of these structures have been deposited in the Protein Data Bank and released in advance of publication), criteria of solvent-accessible surface area and depth of burial have shown that the ionizable side chains in the neutral state are internal and sequestered from contact with bulk water.

The Gibbs free energy required to create positive charge inside SNase varied between 1.5 and 6.9 kcal/mol ($\Delta G°_{ion}$ in Table 5) depending on the location of the internal ionizable group. These energies are comparable to the energies required to create negative charge inside SNase (11). The importance of these free energies is two-fold. First, they demonstrate the remarkable ability of proteins to stabilize charge in their hydrophobic interior. Second, they describe for the first time the range of the minimum thermodynamic stability required for proteins to stay at least partially folded when internal basic groups become charged as part of their natural cycle of biological function. This has important implications for the evolution of enzymes and of other proteins that depend on internal ionizable groups for their biological function. It suggests that enzymes might have evolved by the random introduction of ionizable groups in the core of highly stable proteins, without the need of specialized microenvironments to stabilize the internal ionizable groups. Similarly, it has implications for the engineering of novel active sites in proteins where, in addition to fulfilling the requirements for the desired chemical reaction, the stability of the protein scaffold has to be sufficiently high to tolerate the presence and ionization of the internal residues at the active site. In fact, the combined observations that internal ionizable groups in highly stable proteins are well tolerated when they are charged, and that their $pK_a$ values fall naturally into the range required for function simply by virtue of being internal, suggests that the engineering of artificial enzymes might be simpler than currently thought.

Apparent dielectric constants in the protein interior. Shifts in the $pK_a$ values of internal groups relative to the normal $pK_a$ values of ionizable groups in water are proportional to the Gibbs free energy required to create charge inside a protein. The magnitude of these free energies are determined by the ability of the protein to respond to the presence of charge, which is precisely the property of proteins that determines the energetics of all biological processes governed by internal ionizable groups, and the property that needs to be understood in molecular detail. To gain preliminary insight into these properties the shifts in $pK_a$ values (Table 5) were analyzed using a simple Born formalism that assumes that the $\Delta pK_a$ is determined exclusively by the difference in the self-energy of the charged Lys in water and in an environment with apparent dielectric constant ($\epsilon_{app}$):

$$1.36z(pK_{a,ref} - pK_a) = \frac{332 \cdot Z^2}{2 r_{cav}}\left(\frac{1}{\varepsilon_{app}} - \frac{1}{\varepsilon_{H_2O} e^{\kappa r_{cav}}}\right) + \frac{332 \cdot Z^2}{2 r_{prot}}\left(\frac{1}{\varepsilon_{H_2O} e^{\kappa r_{prot}}} - \frac{1}{\varepsilon_{app}}\right) \quad (4)$$

In this expression $pK_{a,ref}$ is the reference $pK_a=10.4$ for Lys in water, $r_{cav}=2$ Å describes the cavity radius of the ionizable moiety of Lys, $r_{prot}=12$ Å is the radius of the sphere that crudely approximates the size of SNase, and κ is the Debye-Heckel parameter. $\epsilon_{H_2O}=78.5$ was used to describe the dielectric properties of water. The apparent dielectric constants ($\epsilon_{app}$) determined with this expression are not true dielectric constants. They represent a parameter that captures contributions to the $pK_a$ value that are not treated explicitly in the simple model represented by Equation 4. A variety of continuum and microscopic methods are being used in other laboratories to examine the character of the dielectric processes reflected in the $pK_a$ values we have measured. The analysis with equation 4 is simply meant to demonstrate that throughout the protein, the internal Lys residues report high apparent polarizabilities comparable to those of materials with dielectric constants of 8 and higher (Table 5), which are considerably higher than the values of 2 to 4 measured with dry protein powders (19, 20). It has been suggested that this type of analysis invariably leads to high apparent dielectric constants because it ignores dielectric saturation for the ionizable group in water (21); however, we are not aware of any microscopic treatments of ion hydration or experimental data suggesting that dielectric saturation is a problem for these large and asymmetric ions. The general conclusions of the analysis with equation 4, demonstrating that the internal Lys residues report high apparent dielectric constants, are robust and fully consistent with the conclusions from more sophisticated continuum electrostatics methods that take factors other than self-energies into account (2-6).

Structural consequences of ionization of internal Lys residues. A protein can respond to the ionization of an internal group in a variety of ways. If the buried side chain is located in a polar or polarizable microenvironment, its charge can be stabilized without the protein undergoing any significant structural reorganization. If the protein can access an alternative folded conformation in which the charge is stabilized better, perhaps through interaction with internal water molecules or with bulk water, the ionization of the protein will trigger subglobal structural changes. In an extreme case the ionization of the internal group will unfold the protein globally.

To examine the possibility of structural changes coupled to the ionization of internal Lys residues, pH titrations monitored by intrinsic Trp fluorescence (FIG. 15A) and far-UV CD at 222 nm (FIG. 15B) were performed in the range of pH where the internal Lys residues become ionized. The titrations showed that most of the variants were fully folded under conditions of pH where the internal Lys are charged. The small protein appears to be remarkably resilient towards the ionization of internal Lys residues. NMR spectroscopy is currently being used to try to detect conformational reorganization below the level of detection of optical spectroscopic methods.

The $pK_a$ of 5.3 for Lys-92 is within the actual global, acid unfolding titration monitored by Trp-fluorescence or CD spectroscopy, which have pH midpoints of 5.0 and 4.8, respectively (Table 5). This is the only protein for which this is true; the 192K variant is the only one that is globally unfolded by the ionization of the internal Lys. Lys-92 is also the Lys with the most depressed $pK_a$ of all the internal lysines ($pK_a$=5.3). The ionization of Glu-92 also triggered global unfolding (13). The large shifts in the $pK_a$ of Glu-92 and Lys-92 suggest that the polarity and polarizability of the region of the protein where these side chains are embedded is relatively low. This is consistent with crystal structures showing that their side chains are buried deeply in the main hydrophobic core (22). Interestingly, despite being buried deeply, in the crystal structure of the 192K variant (PDB accession code 1TT2.pdb) obtained with crystals grown under conditions of pH where Lys-92 should be neutral, the side chain of Lys-92 occupies two alternative conformations. The side chain of Glu-92 (PDB accession code 1TQ0.pdb) is hydrated by internal water molecules (14-16, 22). Conformational heterogeneity and water penetration are two factors that could help stabilize the internal groups in their charged state, but apparently in the case of the 192K variant the stabilization gained is not enough to prevent global unfolding when Lys-92 is charged.

Figure 15A:
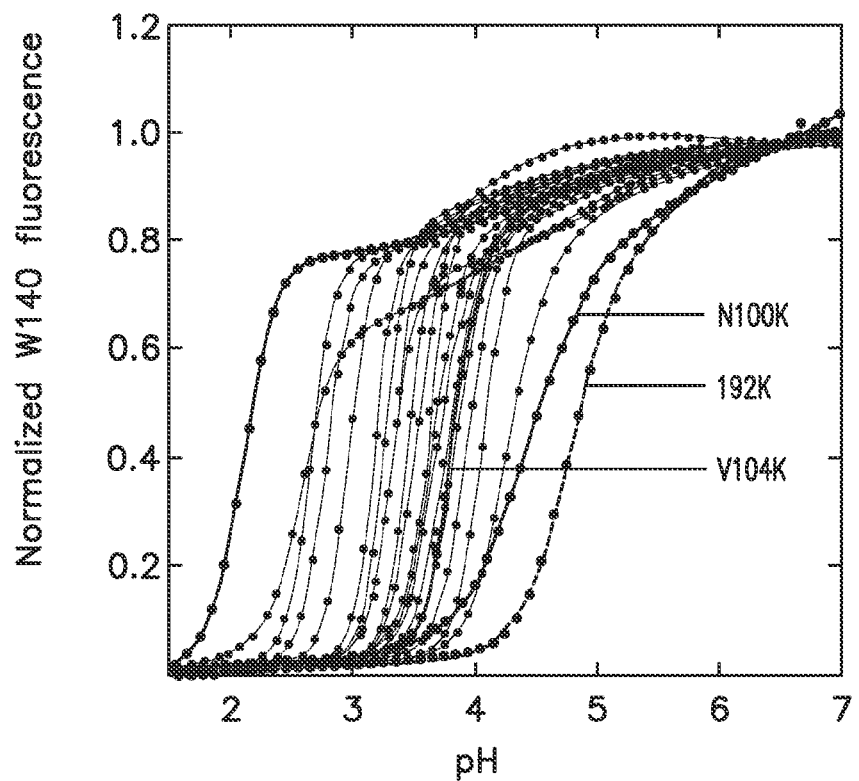
FIG. 15. Conformational consequences of ionization of Lys residues at 25 internal positions. (A) pH titrations of Δ+PHS nuclease (●) and of variants with internal Lys (●) residues monitored by Trp fluorescence, as described previously (11). Variants that exhibit partial (●) or global (●) unfolding concomitant with ionization of the internal Lys are labelled. (B) pH titrations of Δ+PHS nuclease (A) and of variants with internal Lys (●) residues monitored by far-UV CD at 222 nm. Variants that exhibit partial (●) or global (●) unfolding concomitant with ionization of the internal Lys are labelled. (C) Location of Lys residues that trigger local (●) or global (●) structural changes upon ionization, mapped on the structure of Δ+PHS (pdb accession code 3bdc (34)).
Figure 15B:
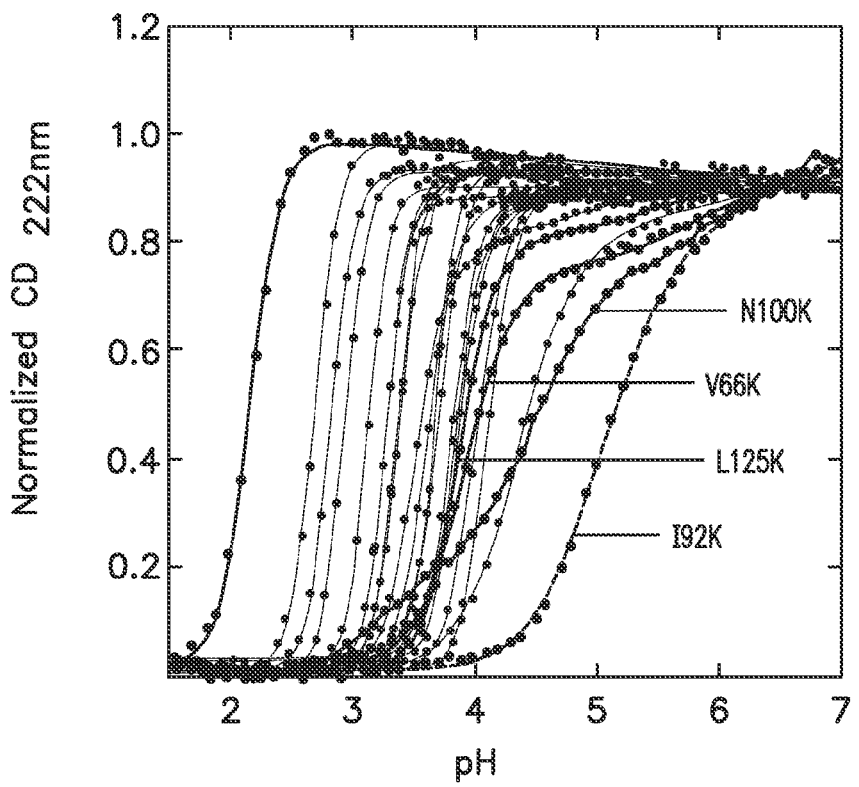
Figure 15C:
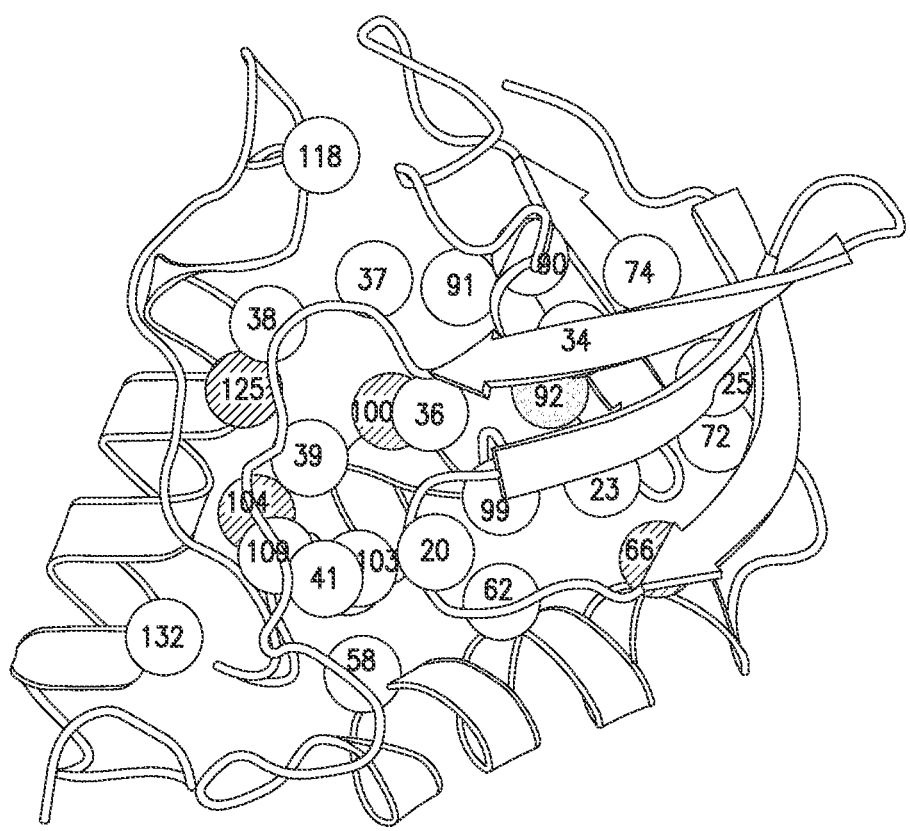

Four variants (V66K, N100K, V104K and L125K) showed pH-dependent changes in optical properties coincident with the ionization of the internal Lys residue (FIG. 15A-B). These are considered cases where the ionization of the internal Lys led to partial or subglobal unfolding because the $pK_a$ values fall within the predenaturational transition, far from the main, global acid unfolding transition. These instances of partial unfolding are subtle and are thus defined only because they seem to be independent of the main, global acid unfolding transition, which can be observed at pH values below the $pK_a$ of the internal Lys. These cases are of special interest because they identify situations where the high apparent polarizability clearly reflects conformational reorganization coupled to the ionization of the internal group. The structural nature of the partial unfolding is not known but it is currently under study with NMR spectroscopy. In the case of ionizable residues at position 66, which have been studied in detail, CD spectroscopy measurements show that the ionization of the internal Lys with a $pK_a$ near 5.7 leads to the apparent loss of approximately one turn of α-helix (4, 23). NMR spectroscopy experiments show that the structural changes are localized to the region of the protein where the side chain of residue 66 is found; the rest of the protein is intact (24). Cases where the ionization of an internal group is coupled to sub-global structural reorganization will be particularly useful for calibration of structure-based electrostatics calculations designed to reproduce conformational changes coupled to changes in pH, and also to examine excited states in the folding energy landscape of proteins (23, 25).

The probability of populating intermediates between the fully folded and the fully denatured states increases as the stability of the native state decreases. Therefore, the likelihood that the ionization of an internal Lys triggers conformational reorganization is governed by the stability of the native state near the pH where ionization occurs. The stability of the protein in the range of pH where the Lys residues ionize ($\Delta G°_{H2O}$ in Table 5) is determined by two factors. One is the loss of stability related to the substitution of the internal position with neutral Lys. This is a pH independent term that accounts for all differences in non-covalent interactions of the original side chain and the Lys side chain. The stability of the Lys-substituted proteins at high pH, near the normal $pK_a$ of Lys, provides an estimate of the cost of substituting with neutral Lys (11, 12). The second factor that destabilizes the Lys-containing variants is the shift in $pK_a$ proper. At pH values below the normal $pK_a$ of Lys in water, the stability of a variant containing a lysine with a highly depressed $pK_a$ value decreases by 1.36 kcal/mol (298K) for every unit shift in the $pK_a$ (FIGS. 13A and 13B). Consequently, larger shifts in $pK_a$ act to decrease protein stability and promote global or partial unfolding in the range of pH where the internal lysine becomes charged. The variants where structural reorganization was observed concomitant with ionization of the internal Lys (V66K, 192K, N100K, V104K L125K) had global stabilities of 3.8 kcal/mol or less at the pH where the groups titrate (Table 5). By this criterion, the L25K and V99K variants, and maybe even the F34K variant, should have also exhibited reorganization concomitant with ionization of the internal Lys, but this was not evident in the titrations monitored with CD or Trp fluorescence spectroscopy.

Coulomb interactions between internal and surface ionizable groups. The stability profiles of 10 Lys-containing variants (Lys-23, Lys-34, Lys-36, Lys-41, Lys-62, Lys-72, Lys-90, Lys-103, Lys-104, Lys-109) were analyzed with Equation 3, which assumes that the $pK_a$ of at least one other ionizable group was affected by the ionization of the internal Lys (e.g. Lys-62 in FIGS. 13C and 13D). In these cases the pH dependence of $\Delta\Delta G°_{H2O}$ above pH 6 was attributed solely to the titration of the introduced Lys side chain. The pH dependence and the sign of the slope of $\Delta\Delta G°_{H2O}$ below pH ~6 implies that the $pK_a$ of one or more carboxylic groups is coupled to the titration of the internal Lys either through Coulomb interactions or by the effect of the substitution with Lys on conformation or dynamics of the protein. Given that the conformation of most Lys-containing variants is unaffected by the titration of the internal Lys, it is reasonable to propose that the apparent interactions between internal Lys residues and surface carboxylic groups are governed by Coulomb effects.

Figures 16A, 16B:
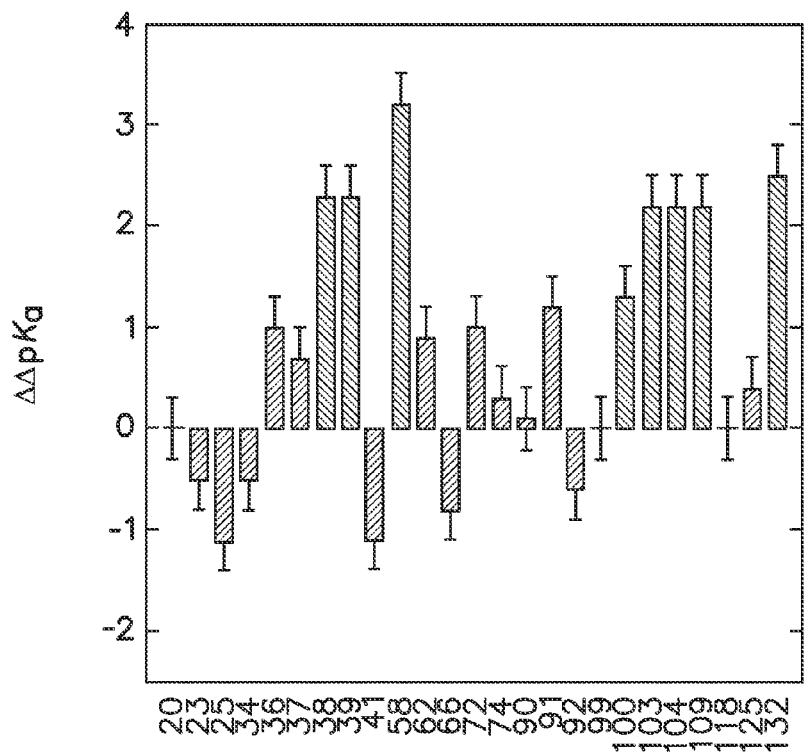
FIG. 16. Comparison of $pK_a$ shifts of Glu and Lys at 25 internal positions. (A) Difference in absolute values of shifts in $pK_a$ of Lys and Glu residues at 25 internal positions in SNase, calculated as ($|(pK_a,Glu-4.5)|-|(pK_a,Lys-10.4)|$). This assumes values of 4.5 and 10.4 for the normal $pK_a$ of Glu and Lys in water, respectively. Positive values identify cases where the shifts in the $pK_a$ of a Glu residue at a given position is greater than the shift in the $pK_a$ of a Lys residue. The color code is meant to distinguish groups with small (green) and large (blue) differences in $pK_a$ values. (B) Distribution of the differences in the $pK_a$ values of Lys and Glu residues mapped on the structure of Δ+PHS (pdb accession code 3bdc (34)).

Further evidence of Coulomb interactions between internal and surface charges comes from comparison of $pK_a$ values of Glu and Lys residues at the same internal positions (FIGS. 16A and 16B). At seven positions (38, 39, 58, 103, 104, 109, 132) the shifts in the $pK_a$ of Glu residues relative to the normal $pK_a$ of 4.5 for Glu in water are greater by nearly one full $pK_a$ unit than the shifts in $pK_a$ values of Lys residues in SNase relative to the normal $pK_a$ of 10.4 of Lys in water (FIG. 16A). These seven positions cluster near the active site of SNase (FIG. 16B), which has a high concentration of acidic residues (Asp-19, Asp-21, Asp-40 and Glu-43, and peripherally Glu-52, Glu-101, Glu-129 and Glu-135). This suggests there are favourable Coulomb interactions between internal Lys residues in the charged state and the cluster of surface acidic residues in this region of the protein, or repulsive interactions between the internal Glu residues and surface negative charges. The observation that with the exception of these residues clustered near the active site, the shifts in $pK_a$ values of Lys or Glu residues at a given position, relative to normal $pK_a$ values of Lys or Glu in water, are within 1 $pK_a$ unit of each other suggests that polarizability is an important determinant of $pK_a$ values of internal ionizable groups in SNase. The extent to which this polarizability involves conformational reorganization remains to be established with NMR spectroscopy. The fact that in the majority of cases no large conformational reorganization concomitant with ionization of Lys or Glu residues was observed by CD or Trp fluorescence suggests that the reorganization is subtle, beyond the level of detection with optical spectroscopy.

Implications for structure-based energy calculations. The preliminary analysis of $pK_a$ shifts with simple continuum models, and strictly in terms of dehydration processes (Eq. 4), suggested that the protein behaves as a material with a relatively high dielectric constant ranging from 8 to 26 (Table 5). The apparent dielectric constants obtained by more sophisticated analysis of some of these variants of SNase with state-of-the-art continuum electrostatics methods were equally high (4, 5), and fully consistent with MD simulations showing that the protein interior can behave as a material with a high dielectric constant (27-29). The magnitudes of the shifts in $pK_a$ values in SNase are consistent with the magnitude of the effects of internal ionizable residues on reduction potentials of myoglobin (30,31), suggesting that the properties probed by the internal ionizable groups in SNase are general properties of proteins. It remains to be seen if structure-based calculations with microscopic methods or with parameterized macroscopic methods can reproduce the properties of internal ionizable groups. This is difficult because these $pK_a$ values reflect a balance between strong and opposing influences (dehydration vs electronic polarization, Coulomb interactions with permanent dipoles or surface charges, and interactions with internal water or reaction field of bulk water) each of which is difficult to calculate. Local or subglobal structural reorganization to maximize favourable interactions between the internal charge and the protein, or more likely, to maximize hydration of the charge, can also be reflected in these $pK_a$ values. The fact that a simple analysis of shifts in $pK_a$ values with the primitive equation 4 or with sophisticated structure-based methods both show that the internal Lys residues report high apparent dielectric constants suggests that polarizability related to conformational reorganization is one of the most important determinants of the $pK_a$ values of these internal ionizable groups. This implies that accurate calculation of $pK_a$ values of internal ionizable groups in proteins might require prediction of conformational rearrangement and alternative conformations, which is still a daunting challenge (8-10). Our data will allow rigorous and unprecedented benchmarking of computational methods for calculation of electrostatic effects in dehydrated environments such as the interior of proteins and interfaces between proteins.

Materials and Methods

Protein Engineering.

All experimental studies were performed with the highly stable z+PHS variant of SNase (4, 11). Lys-containing variants of the Δ+PHS variant of SNase were prepared with QuikChange site-directed mutagenesis on a pET24A+ vector as described previously (4, 11). Purification was performed as described previously (32).

Stability Measurements.

Stability measurements were performed with guanidinium chloride titrations using an Aviv Automated Titration Fluorimeter 105 as described previously (33). Linkage analysis of pH dependence of stability to obtain $pK_a$ values was performed as described previously (2, 4, 7).

Optical Spectroscopy.

pH titrations monitored with CD at 222 nm or with intrinsic Trp fluorescence were performed with an Aviv Automated Titration Fluorimeter model 105 and with an Aviv circular dichroism spectrometer model 215, respectively. The experiments were performed following protocols published previously (33).

REFERENCES

1. Rastogi V K & Girvin M E (1999) Structural changes linked to proton translocation by subunit c of the ATPase synthase. *Nature* 402: 263-268.
2. Dwyer J, et al. (2000) High apparent dielectric constants in the interior of a protein reflect water penetration. *Biophysical Journal* 79: 1610-1620.
3. Harms M J, et al. (2009) The pKa values of acidic and basic residues buried at the same internal location in a protein are governed by different factors. *J. Mol. Biol.* 389: 34-47.
4. Karp D A, et al. (2007) High Apparent Dielectric Constant Inside a Protein Reflects Structural Reorganization Coupled to the Ionization of an Internal Asp. *Biophysical Journal* 92: 2041-2053.
5. Fitch C A, et al. (2002) Experimental pKa values of buried residues: analysis with continuum methods and role of water penetration. *Biophysical Journal* 82: 3289-3304.
6. García-Moreno E. B, et al. (1997) Experimental measurement of the effective dielectric in the hydrophobic core of a protein. *Biophysical Chemistry* 64: 211-224.
7. Stites W E, Gittis A G, La man E E, & Shortle D (1991) In a staphylococcal nuclease mutant the side-chain of a lysine replacing valine 66 is fully buried in the hydrophobic core. *Journal of Molecular Biology* 221: 7-14.
8. Ghosh N & Cui Q (2008) pKa of residue 66 in staphylococcal nuclease. I. Insights from QM/MM simulations with conventional sampling. *J. Phys. Chem. B.* 112: 8387-8397.

9. Schutz C N & Warshel A (2001) What are the dielectric "constants" of proteins and how to validate electrostatic models? *Proteins: Structure, Function, and Genetics* 44: 400-417.
10. Zheng L, Mengen C, & Yang W (2008) Random walk in orthogonal space to achieve efficient free-energy simulation of complex systems. *Proc. Natl. Acad. Sci. USA* 105: 20227-20232.
11. Isom D G, et al. (2008) High tolerance for ionizable residues in the hydrophobic interior of proteins. *Proc. Natl. Acad. Sci. USA* 105: 17784-17788.
12. Thurlkill R L, Grimsley G R, Scholtz J M, & Pace C N (2006) Hydrogen Bonding Markedly Reduces the pK of Buried Carboxyl Groups in Proteins. *Journal of Molecular Biology* 362: 594-604.
13. Isom D G, et al. (2010) Charges in the hydrophobic interior of a protein. *Proc. Natl. Acad. Sci. USA* (in press).
14. Damjanovic A, Garcia-Moreno E. B, Lattman E E, & Garcia A E (2005) Molecular Dynamics Study of Water Penetration in Staphylococcal Nuclease. *Proteins: Structure Function and Bioinformatics* 60: 433-449.
15. Damjanovic A, et al. (2007) Role of flexibility and polarity as determinants of the hydration of internal cavities and pockets in proteins. *Biophysical Journal* 93: 2791-2804.
16. Schlessman J L, et al. (2008) Crystallographic study of hydration of an internal cavity in engineered proteins with buried polar or ionizable groups. *Biophys. J.* 94: 3208-3216.
17. Harms M J, et al. (2008) A buried lysine that titrates with a normal pKa: Role of conformational flexibility at the protein water interface as a determinant of pKa values. *Protein Science* 17: 833-845.
18. Ho M, Menetret J, Tsuruta H, & Allen K N (2009) The origin of the electrostatic perturbation in acetoacetate decarboxylase. *Nature* 459: 393-399.
19. Bone S & Pethig R (1982) Dielectric studies of the binding of water to lysozyme. *Journal of Molecular Biology* 157: 571-575.
20. Bone S & Pethig R (1985) Dielectric studies of protein hydration and hydration-induced flexibility. *Journal of Molecular Biology* 181: 323-326.
21. Gong H, Hocky G, & Freed K F (2008) Influence of nonlinear electrostatics on transfer energies between liquid phases: charge burial is far less expensive than Born Model. *Proc. Natl. Acad. Sci. USA* 105: 11146-11151.
22. Nguyen D M, Reynald R L, Gittis A G, & Lattman E E (2004) X-ray and thermodynamic studies of staphylococcal nuclease variants 192E and 192K: Insights into polarity of the protein interior. *J. Mol. Biol.*: 565-574.
23. Karp D A, Stahley M R, & García-Moreno E. B (2010) Conformational consequences of ionization of Lys, Asp, and Glu buried at position 66 in staphylococcal nuclease. *Biochemistry* 49: 4138-4146.
24. Chimenti M S, Castaneda C A, Majumdar A, & Garcia-Moreno E. B (2010) Structural origins of high apparent dielectric constants experienced by ionizable groups in the hydrophobic core of a protein. *J. Mol. Biol.* (in press).
25. Zheng Z & Sosnick T R (2010) Protein vivisection reveals elusive intermediates in folding. *J. Mol. Biol.* 397: 777-788.
26. Pey A L, et al. (2010) Modulation of buried ionizable groups in proteins with engineered surface charge. *J. Am. Chem. Soc.* 132: 1218-1219.
27. Simonson T & Perahia D (1995) Internal and Interfacial Dielectric Properties of Cytochrome c from Molecular Dynamics in Aqueous Solution. *Proceedings of the National Academy of Sciences of the United States of America* 92: 1082-1086.
28. Smith P E, Brunne R M, Mark A E, & van Gunsteren W F (1993) Dielectric properties of trypsin inhibitor and lysozyme calculated from molecular dynamics simulations. *Journal of Physical Chemistry* 97: 2009-2014.
29. Simonson T & Brooks III C L (1996) Charge screening and the dielectric constant of proteins: Insights from molecular dynamics. *Journal of the American Chemical Society* 118: 8452-8458.
30. Varadarajan R, Zewert T E, Gray H B & Boxer S G (1989) Effects of Buried Ionizable Amino Acids on the Reduction Potential of Recombinant Myoglobin. *Science* 243: 69-72.
31. Varadajaran R, Lambright D G, Boxer S G (1989) Electrostatic Interactions in Wild-Type and Mutant Recombinant Human Myoglobins. *Biochemistry* 28: 3771-3781.
32. Shortle D & Meeker A (1986) Mutant forms of staphylococcal nuclease with altered patterns of guanidine hydrochloride and urea denaturation. *Proteins: Structure, Function, and Genetics* 1: 81-89.
33. Whitten S T & García-Moreno E. B (2000) pH dependence of stability of staphylococcal nuclease: Evidence of substantial electrostatic interactions in the denatured state. *Biochemistry* 39: 14292-14304.
34. Castañeda C A, et al. (2009) Molecular determinants of the pKa values of Asp and Glu residues in staphylococcal nuclease. *Proteins: Struct. Funct. Bioinf* 77: 570-588.

What is claimed is:

1. A method of engineering a pH sensitive conformational switch in a protein that is not a staphylococcal nuclease, the method comprising:
   i) selecting a protein that has a minimum initial thermodynamic stability of 12 kcal/mol per pH unit at 298 K to tolerate the energetic cost of substituting one or more amino acid residues in the interior of a protein with a destabilizing ionizable group;
   ii) selecting one or more amino acid residues in the interior of the protein whose substitution with one or more ionizable amino acid residues would cause the protein to switch conformation in response to small changes in pH; and
   iii) substituting the selected one or more amino acid residues in the interior of the protein with one or more ionizable amino acid residues to form a pH sensitive conformational switch in the protein in which the one or more ionizable amino acid residues titrate with a pKa value shifted relative to the normal pKa value in water for the one or more ionizable amino acid residues, the protein is fully folded under conditions of pH in which the internal ionizable amino acid residues are charged, and the protein switches conformation in response to small changes in pH.

2. The method of claim 1, wherein the one or more ionizable amino acid residues is basic and the shift in pKa value depresses the pKa relative to the normal pKa value in water for the one or more ionizable amino acid residues.

3. The method of claim 1, wherein the one or more ionizable amino acid residues is acidic and the shift in pKa value raises the pKa relative to the normal pKa value in water for the one or more ionizable amino acid residues.

4. The method of claim 1, wherein the one or more ionizable amino acid residues is selected from the group consisting of Lys, Arg, His, Asp, and Glu.

5. The method of claim 1, wherein the one or more amino acid residues in the interior of the protein are selected from the group consisting of Ala, Ile, Leu, Met, Phe, Trp, Tyr, Val, Asn, Gln, Cys, Gly, Pro, Thr, and Ser.

6. The method of claim 1, further comprising determining that the protein is fully folded under conditions of pH in which the internal ionizable amino acid residues are charged.

* * * * *

UNITED STATES PATENT AND TRADEMARK OFFICE
CERTIFICATE OF CORRECTION

PATENT NO.         : 9,499,580 B2
APPLICATION NO.    : 13/513259
DATED              : November 22, 2016
INVENTOR(S)        : Bertrand E. Garcia-Moreno and Daniel G. Isom Page 1 of 1

It is certified that error appears in the above-identified patent and that said Letters Patent is hereby corrected as shown below:

In the Specification

Column 1, Line 4, immediately after the title, please add the following paragraph:

STATEMENT OF GOVERNMENTAL INTEREST
This invention was made with government support under grant number GM061597, awarded by the National Institutes of Health, and grant number MCB-0743422, awarded by the National Science Foundation. The government has certain rights in the invention.

Signed and Sealed this
Twentieth Day of February, 2018

Andrei Iancu
*Director of the United States Patent and Trademark Office*